US012617863B2

(12) United States Patent
Ni

(10) Patent No.: US 12,617,863 B2
(45) Date of Patent: May 5, 2026

(54) HUMANIZED ANTI-GLYCOPROTEIN IB ALPHA (GPIBALPHA) ANTIBODIES

(71) Applicant: CCOA THERAPEUTICS INC., Toronto (CA)

(72) Inventor: Heyu Ni, North York (CA)

(73) Assignee: CCOA THERAPEUTICS INC., Toronto (CA)

( * ) Notice: Subject to any disclaimer, the term of this patent is extended or adjusted under 35 U.S.C. 154(b) by 963 days.

(21) Appl. No.: 17/783,198

(22) PCT Filed: Dec. 10, 2020

(86) PCT No.: PCT/CA2020/051699
§ 371 (c)(1),
(2) Date: Jun. 7, 2022

(87) PCT Pub. No.: WO2021/113974
PCT Pub. Date: Jun. 17, 2021

(65) Prior Publication Data
US 2023/0022143 A1 Jan. 26, 2023

Related U.S. Application Data

(60) Provisional application No. 62/946,086, filed on Dec. 10, 2019.

(51) Int. Cl.
*C07K 16/28* (2006.01)
*A61P 7/02* (2006.01)
*A61K 39/00* (2006.01)

(52) U.S. Cl.
CPC ............ *C07K 16/2896* (2013.01); *A61P 7/02* (2018.01); *A61K 2039/505* (2013.01); *C07K 2317/24* (2013.01); *C07K 2317/54* (2013.01); *C07K 2317/55* (2013.01); *C07K 2317/622* (2013.01); *C07K 2319/31* (2013.01)

(58) Field of Classification Search
None
See application file for complete search history.

(56) References Cited

U.S. PATENT DOCUMENTS

| | | | | |
|---|---|---|---|---|
| 6,180,370 B1 * | 1/2001 | Queen | ..................... | A61P 19/02 |
| | | | | 435/69.6 |
| 7,112,661 B1 | 9/2006 | Miller | | |
| 7,332,162 B1 | 2/2008 | Deckmyn et al. | | |
| 8,323,652 B2 * | 12/2012 | Ni | ............................ | A61P 9/00 |
| | | | | 424/153.1 |
| 2009/0010934 A1 | 1/2009 | Deckmyn et al. | | |
| 2010/0150837 A1 | 6/2010 | Ni et al. | | |

FOREIGN PATENT DOCUMENTS

| | | |
|---|---|---|
| CN | 102988983 A | 3/2013 |
| CN | 107082809 A | 8/2017 |

OTHER PUBLICATIONS

Balogh EP. Committee on Diagnostic Error in Health Care; Board on Health Care Services; Institute of Medicine; The National Academies of Sciences, Engineering, and Medicine; Improving Diagnosis in Health Care. Washington (DC): National Academies Press (US) (Year: 2025).*
Berdine, Gilbert et al. "Clinical entities, phenotypes, causation, and endotypes based on selected asthma publications." Proceedings (Baylor University. Medical Center) vol. 33,4 580-585. Jul. 27, 2020, doi: 10.1080/08998280.2020.1793444 (Year: 2020).*
Sela-Culang et al. Frontiers in immunology 4 (2013): 302 (Year: 2013).*
Monnier, Philippe P., Robin J. Vigouroux, and Nardos G. Tassew Antibodies 2.2 (2013): 193-208 (Year: 2013).*
De Meyer, Simon F et al. "Platelet glycoprotein Ibα is an important mediator of ischemic stroke in mice." Experimental & translational stroke medicine vol. 3 9. Sep. 13, 2011, doi: 10.1186/2040-7378-3-9 (Year: 2011).*
Piche-Nicholas, Nicole M., et al. "Changes in complementarity-determining regions significantly alter IgG binding to the neonatal Fc receptor (FcRn) and pharmacokinetics." MAbs. vol. 10. No. 1. Taylor & Francis, 2018 (Year: 2018).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
PCT, Written Opinion and International Search Report of International Application No. PCT/CA2020/051699, mailing date Mar. 15, 2021.
Qi, Y. et al. "Novel antibodies against GPIba inhibit pulmonary metastasis by affecting vWF-GPIba interaction", J. Hematol. Oncol. Sep. 17, 2018 (Sep. 17, 2018), vol. 11, no. 1, Article No. 117, ISSN 1756-8722. *entire document*.

* cited by examiner

Primary Examiner — Michael Szperka
Assistant Examiner — Lia E Taylor
(74) Attorney, Agent, or Firm — Li & Cai Intellectual Property Office

(57) ABSTRACT

Multivalent anti-platelet glycoprotein I(b)alpha antibodies can cause severe side effects. The present disclosure provides humanized antibodies specifically recognizing glycoprotein I(b)alpha and lacking a Fc portion, therefore Bleeding Time do not interact with Fc receptor. The humanized antibodies are capable of preventing platelet activation and aggregation, and reducing thrombus size/growth and prevent vessel occlusion. They can be also very useful to decrease platelet-tumor cell interaction and decrease tumor metastasis. At therapeutic doses, the humanized antibodies lack the ability to induce platelet activation, induce thrombocytopenia; and/or prolong bleeding time.

26 Claims, 22 Drawing Sheets
Specification includes a Sequence Listing.

A

B

C

D

E

A

B

D

A

B

A          H001 binds to mouse platelets in vivo

B          P-selectin expression on mouse platelets

A

B

*: Compare to Control
: Compare to H001 10 µg

A

B

C

A

B

C

A

B

C

C100-scFv (µg/mL)

D

C100-scFv-HSA (µg/mL)

HUMANIZED ANTI-GLYCOPROTEIN IB ALPHA (GPIBALPHA) ANTIBODIES

CROSS-REFERENCE TO RELATED APPLICATIONS AND SEQUENCE LISTING STATEMENT

This application claims priority from U.S. provisional application Ser. No. 62/946,086 filed on Dec. 10, 2019 and incorporated herewith in its entirety. The sequence listing associated with this application is provided in text format and is hereby incorporated by reference into the specification. The name of the text file containing the sequence listing is PCT_-_Sequence_listing_as_filed. The text file is 81.2 Ko, was created on Dec. 9, 2020 and is being submitted electronically.

TECHNOLOGICAL FIELD

The present disclosure concerns humanized antibodies which specifically recognize and bind to the platelet glycoprotein I(b)α (GPIbα) as well as protein construct comprising same, and therapeutic uses associated thereto.

BACKGROUND

Platelet adhesion and aggregation at sites of atherosclerotic rupture in coronary or cerebral arteries are usually the critical events in acute thrombosis. Therefore, anti-platelet therapy represents one of the key treatment regimens in reducing cardiovascular deaths, including (i) cyclooxygenase inhibitors such as aspirin; (ii) platelet P2Y12 receptor antagonists such as clopidogrel, prasugrel and ticagrelor; (iii) αIIbβ3 antagonists such as abciximab, eptifibatide and tirofiban; and (iv) PAR1 antagonists such as vorapaxar, etc. However, limitations of current anti-platelet therapies, such as a slow onset/weak/poor inhibition of platelet function, excessive bleeding complications, thrombocytopenia and unexpected platelet activation are major concerns that drive therapeutic advances. Notably, concerning acute ischemic stroke, since the risk for intracranial hemorrhage and/or potential neurotoxicity (e.g. recombinant tissue plasminogen activator (tPA)) of current anti-thrombotic/thrombolytic drugs, as well as for patients who have passed the window for intravenous thrombolysis, treatments are very limited if it is not available.

Platelet GPIb-IX-V complex has emerged as a promising anti-platelet target. GPIb-IX-V complex is a key platelet receptor in initiating platelet adhesion and translocation to the injured vessel wall, particularly at high shear. Platelet adhesion/translocation onto the subendothelium is mediated by the binding of GPIbα subunit to von Willebrand Factor (VWF) that anchored/immobilized on the injured vessel wall. VWF is a multimeric adhesive blood protein secreted from activated endothelial cells and platelets. GPIbα-VWF binding can then trigger a signal transduction process that leads to the release of platelet agonists, such as thromboxane A2 and ADP, and the activation of platelet αIIbβ3 integrin that results in platelet aggregation mediated by αIIbβ3 binding to fibrinogen, VWF, etc. Under high shear conditions, the GPIbα-VWF interaction are required for pathologic growth of occlusive thrombi (both platelet adhesion and platelet aggregation/agglutination) at sites of arterial stenosis where blood flows with wall shear rates that may exceed $10,000\text{-}40,000 \text{ s}^{-1}$, while under low shear conditions (such as in the most cases of hemostasis), platelet adhesion can be directly mediated by αIIbβ3-fibrinogen/fibrin and α2β1/GPVI-collagen interactions, etc. Therefore, pharmacological inhibition of GPIbα may result in a lower risk of systemic bleeding and improved safety compared to other antiplatelet drugs that are not specifically target thrombosis at high shear. It has also been shown that GPIbα is important for leukocyte recruitment under thrombo-inflammatory conditions, such as in acute ischemic stroke. Moreover, ischemia—reperfusion (e.g. by thrombolysis or thrombectomy) of the previously hypoxic brain areas can increase the pro-inflammatory function of platelets via GPIbα, which may further promote thrombo-inflammatory neuronal damage and infarct growth. Furthermore, GPIbα has been considered exclusively expressed on platelets and megakaryocytes. Thus, direct platelet GPIbα antagonists have a great potential to be developed as effective and safer anti-platelet drugs for the treatment of acute thrombotic events, such as heart attack and stroke.

Notably, novel anti-platelet strategies targeting GPIbα-VWF interaction has been demonstrated as an effective therapy to treat acquired thrombotic thrombocytopenic purpura (aTTP), a thrombotic microangiopathy and a life-threatening condition with a high mortality rate if untreated. Autoantibodies against ADAMTS13 (a disintegrin and metalloproteinase with thrombospondin type 1 motif, member 13), the VWF-cleaving protease that cleaves/reduces the multimeric size of VWF, results in the severe deficiency of ADAMTS13 activity. These ultra-large VWF are hyper-adhesive that cause the formation of platelet (GPIbα)-VWF microthrombi in blood vessels, leading to the end-organ ischemia and infarction, low platelet counts and destruction of red blood cells. Therefore, blocking the interaction between VWF and platelet GPIbα can prevent the development of acute TTP by achieving faster normalization of platelet counts and reducing the thromboembolic events.

The nanobody caplacizumab targeting the VWF A1 domain has been approved for the treatment of adults experiencing an acute episode of aTTP, in conjunction with plasma exchange (PEX) and immunosuppression for a minimum of 30 days after stopping daily PEX. However, bleeding-related adverse events were more common with caplacizumab (65% vs. 48%), as were serious bleeding events (11% vs. 1%). Another barrier of caplacizumab has been the huge cost of the drug. Current pricing of caplacizumab in 2020 was more than US$8,000 per dose with treatment regimens recommending daily dosing for 30 days following the last plasma exchange with the possibility of extended treatment pending the recovery of ADAMTS13 activity. Due to that VWF is consistently released from the activated endothelium, the relative stable levels of GPIbα on platelets, which have a short lifespan of 7-10 days in humans, appears to be a more attractive/potent target for TTP therapy.

Patent CN103263662 describes a GPIbα-binding snake C-type lectin (snaclec) anti-platelet thrombolysin which is purified from the venom of the snake *Deinagkistrodon acutus*. Anti-platelet thrombolysin inhibited ristocetin-induced human platelet aggregation and thrombosis through blocking GPIb-VWF interactions without significantly altering bleeding time or coagulation. Anti-platelet thrombolysin is currently evaluated in the phase II clinical trials in patients with acquired thrombotic thrombocytopenic purpura and ST segment elevation myocardial infarction. However, it is known that foreign snake proteins may induce an immune response that generates anti-drug antibodies which can neutralized the drug and eliminate the therapeutic efficacy. Further, these antibodies may cause allergic reactions or immune complex formation that may damage kidney or joints (arthritis). Furthermore, the need for re-administration may stimulate the memory immune cells and boost such immune responses and immune reactions.

U.S. Pat. No. 7,049,128 describes recombinant GPG-290 or GPIb-290/2V-Immunogloblin (Ig) fusion polypeptides, which is a soluble chimeric protein containing the mutant GPIbα N-terminal extracellular 290 amino acids (G233V and M239V) linked via a proline to the Fc fragment of human IgG1. GPG-290 competed with platelet GPIbα for binding VWF, with a fourteen-fold affinity for VWF compared with the wild-type GPIbα. In animal models, GPG-290 dose-dependently prolonged the time to coronary artery occlusion, and inhibited platelet aggregation, thrombosis and recurrent coronary cyclic flow reduction without prolonging the bleeding time at doses ranging from 50-100 µg/kg. However, the higher dose tested (500 µg/kg) induced three to fourfold increase of the bleeding time, likely due to that GPG-290 binding to alpha-thrombin with an high affinity which makes the alpha-thrombin is not available for hemostasis.

U.S. Pat. No. 7,727,535 further describes a GPIb-290/2V/FFF-Ig variant fusion protein (Y276F, Y278F, and/or Y279F), which exhibited a limited/lower affinity binding to alpha-thrombin, and had a 50% decrease in potency in inhibiting repetitive coronary artery thrombosis (i.e. inhibiting recurrent coronary cyclic flow reduction), and in prolonging tail bleeding times and increasing ADP closure times as assessed by a Platelet Function Analyzer-100 (PFA-100) as compared to GPG-290. However, these GPIb-Ig fusion proteins are high molecular weight chimeric protein (~130 kDa), which mainly targets the subendothelium immobilized VWF or plasma VWF under high shear rates. Therefore, the amount and accessibility of these fusion proteins are less well predictable and the high amount of the products to be injected could be a potential limitation. Another limitation could be the risk of anti-drug antibody generation. The GPIb-Ig fusion proteins are bioengineered chimera proteins. Although both GPIbα polypeptides and Fc fragment are derived from human genes, which may minimize their antigenicity, the GPIbα variant mutations and the joint regions between GPIbα and Fc portion may generate neoepitopes that may induce an immune response. In addition, the fusion protein may generate some conformational neoepitopes that induce anti-drug antibody production.

Neutralizing monoclonal antibodies directed against human GPIbα (anti-GPIbα mAbs) were also described in the art. However, the majority anti-GPIbα mAbs available to-date are of murine origin, and therefore can elicit a human anti-mouse response in clinical use. In addition, the intact anti-GPIbα mAbs often lead to platelet activation, likely due to that the binding of intact mAbs induced platelet GPIbα-mediated signaling transduction, which can unexpectedly aggravate platelet aggregation and thrombosis. Furthermore, the intact anti-GPIbαmAbs binding to platelets can trigger both Fc-dependent and Fc-independent platelet clearance, leading to thrombocytopenia (i.e. low platelet counts). Therefore, the intact anti-GPIbα mAbs present a very limited therapeutic potential.

CN102988983 describes a Fab fragment of chimeric antibody chSZ2, a chimeric mAb against human GPIbα, that inhibits ristocetin-induced platelet aggregation in vitro in a dose-dependent manner. However, since it is a chimeric antibody which retains the variable regions of mouse antibody and the constant regions are replaced by those of human, the immunogenicity is still a major concern. Importantly, the in vivo function of chSZ2 for preventing/treating thrombotic diseases have never been demonstrated, due to shortage of animal models since it may not recognize GPIbα from other animal species as well recognized in the field.

U.S. Pat. No. 7,332,162 describes another Fab fragment of the humanized 6B4 (h6B4-Fab), a murine mAb which was raised against purified human GPIbα. h6B4-Fab reduced or completely abolished cyclic flow reductions of a stenosed femoral artery in baboons. However, the antithrombotic effect of h6B4-Fab was accompanied by a prolongation of the bleeding time. Moreover, these anti-GPIbα antibodies, as well as their corresponding Fab fragments, were generated in wild-type mice using conventional techniques (i.e. immunized by human GPIbα) which cannot recognize the mouse GPIbα (because mouse and human GPIbα possess an important degree of homology), and the repertoire of the antibodies produced to epitopes present on the human GPIbα and absent on the mouse GPIbα is limited. Therefore, these mAbs cannot be characterized and evaluated in rodents or other animal species for the important preclinical pharmacology, toxicology and pharmacokinetics studies. Whether h6B4-Fab may cause platelet activation is also of concern since its precursor mAb 6B4 can clearly cause platelet activation and severe thrombocytopenia.

There is thus a need for an improved therapeutic agent targeting the platelet GPIb-IX-V complex which would not cause platelet activation, platelet destruction, thrombocytopenia, nor significant bleeding complications.

BRIEF SUMMARY

The present disclosure concern a humanized and antibody specifically recognizing glycoprotein I(b)α (GPIbα) and protein construct comprising same as well as therapeutic uses associated thereto. The humanized antibody is capable of preventing platelet activation, aggregation, thrombus growth (particularly at high shear), lacks the ability to activate platelets (e.g., does not activate platelets), lacks the ability to induce thrombocytopenia; and/or at a therapeutic dose, lacks the ability to prolong bleeding time.

In a first aspect, the present disclosure provides a humanized antibody specifically recognizing glycoprotein I(b)α (GPIbα). The humanized antibody lacks a Fc receptor moiety. The humanized antibody is capable of preventing platelet activation, aggregation, and/or thrombus growth; lacks the ability to activate platelets; lacks the ability to induce thrombocytopenia; and/or at a therapeutic dose, lacks the ability to prolong bleeding time. In an embodiment, the humanized antibody is capable of recognizing a human GPIbα, a mouse GPIbα, a dog GPIbα, a rat GPIbα, a rabbit GPIbα and/or a monkey GPIbα. In another embodiment, the humanized antibody is an antibody fragment. In an example, the antibody can be a $F(ab)_2$ fragment. For example, the antibody fragment can be a Fab antibody fragment. In another embodiment, the antibody fragment can be a single chain variable fragment (scFv). In an embodiment, the humanized antibody of has a heavy chain. In some embodiments, the heavy chain comprises: a first CDR having an amino acid sequence of GFTFSSFAMS (SEQ ID NO: 37), a variant thereof or a fragment thereof; a second CDR having an amino acid sequence of SITSAGTPYYPDSVLG (SEQ ID NO: 38), a variant thereof or a fragment thereof; and/or a third CDR having an amino acid sequence of SRGYEDYFDY (SEQ ID NO: 39), a variant thereof or a fragment thereof. In still a further embodiment, the heavy chain further comprises a CH1 region of a human IgG1 antibody. For example, the CH1 region of the human $IgG_1$ antibody has the amino acid sequence of SEQ ID NO: 40, 47, 54 or 61, a variant thereof or a fragment thereof. In an embodiment, the heavy chain has the amino acid sequence of SEQ ID NO: 36, 43, 50 or 57, a variant thereof or a fragment thereof. In another embodiment, the humanized and monoclonal antibody has a light chain. In some embodiments, the light chain comprises: a first CDR having an amino acid sequence of KSSQSLLNSRNQKNYLA (SEQ ID NO: 65), a variant thereof or a fragment thereof; a second CDR having an amino acid sequence of FTSTRES (SEQ ID NO: 66), a variant thereof or a fragment thereof; and/or a third CDR having an amino acid sequence of QQHYSSPWT (SEQ ID NO: 67), a variant thereof or a fragment thereof. In some embodiments, the light chain further comprises a kappa chain C region of a human IgG₁ antibody. In some additional embodiments, the kappa chain C region has the amino acid sequence of SEQ ID NO: 68, 75, 82, or 89, a variant thereof or a fragment thereof. In a further embodiment, the light chain has the amino acid sequence of SEQ ID NO: 64, 71, 78 or 85, a variant thereof or a fragment thereof. In some embodiments, the humanized antibody has the heavy chain of SEQ ID NO: 36, a variant thereof or a fragment thereof and the light chain of SEQ ID NO: 64, a variant thereof or a fragment thereof; the heavy chain of SEQ ID NO: 36, a variant thereof or a fragment thereof and the light chain of SEQ ID NO: 71, a variant thereof or a fragment thereof; the heavy chain of SEQ ID NO: 36, a variant thereof or a fragment thereof and the light chain of SEQ ID NO: 78, a variant thereof or a fragment thereof; the heavy chain of SEQ ID NO: 36, a variant thereof or a fragment thereof and the light chain of SEQ ID NO: 85, a variant thereof or a fragment thereof; the heavy chain of SEQ ID NO: 43, a variant thereof or a fragment thereof and the light chain of SEQ ID NO: 64, a variant thereof or a fragment thereof; the heavy chain of SEQ ID NO: 43, a variant thereof or a fragment thereof and the light chain of SEQ ID NO: 71, a variant thereof or a fragment thereof; the heavy chain of SEQ ID NO: 43, a variant thereof or a fragment thereof and the light chain of SEQ ID NO: 78, a variant thereof or a fragment thereof; the heavy chain of SEQ ID NO: 43, a variant thereof or a fragment thereof and the light chain of SEQ ID NO: 85, a variant thereof or a fragment thereof; the heavy chain of SEQ ID NO: 50, a variant thereof or a fragment thereof and the light chain of SEQ ID NO: 64, a variant thereof or a fragment thereof; the heavy chain of SEQ ID NO: 50, a variant thereof or a fragment thereof and the light chain of SEQ ID NO: 71, a variant thereof or a fragment thereof; the heavy chain of SEQ ID NO: 50, a variant thereof or a fragment thereof and the light chain of SEQ ID NO: 78, a variant thereof or a fragment thereof; the heavy chain of SEQ ID NO: 50, a variant thereof or a fragment thereof and the light chain of SEQ ID NO: 85, a variant thereof or a fragment thereof; the heavy chain of SEQ ID NO: 57, a variant thereof or a fragment thereof and the light chain of SEQ ID NO: 64, a variant thereof or a fragment thereof; the heavy chain of SEQ ID NO: 57, a variant thereof or a fragment thereof and the light chain of SEQ ID NO: 71, a variant thereof or a fragment thereof; the heavy chain of SEQ ID NO: 57, a variant thereof or a fragment thereof and the light chain of SEQ ID NO: 78, a variant thereof or a fragment thereof; or the heavy chain of SEQ ID NO: 57, a variant thereof or a fragment thereof and the light chain of SEQ ID NO: 85, a variant thereof or a fragment thereof.

In a second aspect, the present disclosure provides a chimeric protein comprising the humanized antibody of described herein and a carrier protein.

In a third aspect, the present disclosure provides a pharmaceutical composition comprising (i) the humanized antibody described or the chimeric protein described herein and (ii) a pharmaceutical excipient.

In a fourth aspect, the present disclosure provides a method of preventing or limiting the interaction between glycoprotein I(b)α (GPIbα) present on a platelet and a GPIbα ligand (such as, for example, von Willebrand factor (VWF), thrombin, kininogen, P-selectin, thrombospondin, etc.), the method comprising contacting the humanized antibody described herein, the chimeric protein described herein or the pharmaceutical composition described herein with the platelet. In some embodiments, the method is for preventing or limiting platelet activation. In an embodiment, the GPIbα ligand is the von Willebrand factor (VWF) and/or thrombin. In a specific embodiment, the humanized antibody, the chimeric protein or the pharmaceutical composition is contacted with the platelet prior to, at the same time or after the GPIbα ligand is contacted with the platelet. In a further embodiment, the method is for preventing or limiting the interaction in vivo in a subject in need thereof. In another embodiment, the method is for preventing the formation or the growth of a thrombus in the subject in need thereof. In another embodiment, the method is for reducing the size of a thrombus or the number of thrombi in the subject in need thereof. In some embodiments, the method further comprises determining the presence, the location and/or the size of the thrombus in the subject. In yet another embodiment, the subject is at risk of experiencing or has experienced a pathological thrombosis. In yet another embodiment, the subject is at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or vascular inflammation. In some embodiments, the method is for reducing or limiting tumor metastasis in the subject in need thereof. In further embodiment, the tumor metastasis are liver tumor metastasis. In yet another embodiment, the method further comprises determining the presence, the location and/or the size of the tumor metastasis in the subject.

In a fifth aspect, the present disclosure provides using the humanized antibody described herein, the chimeric protein described herein or the pharmaceutical composition for preventing or limiting the interaction between glycoprotein I(b)α (GPIbα) present on a platelet and von Willebrand factor (VWF) and/or thrombin as well as other GPIbα ligands. The present disclosure also provides using the humanized antibody described herein, the chimeric protein described herein or the pharmaceutical composition in the manufacture of a medicament for preventing or limiting the interaction between glycoprotein I(b)α (GPIbα) present on a platelet and von Willebrand factor (VWF) and/or thrombin. The contacting step can occur under low or high shear rates. In some embodiments, the humanized and monoclonal antibody, the chimeric protein or the pharmaceutical composition is for preventing or limiting platelet activation. In a specific embodiment, the humanized antibody, the chimeric protein or the pharmaceutical composition is for contacting with the platelet prior to, at the same time or after the VWF and/or thrombin as well as other GPIbα ligands is contacted with the platelet. In a further embodiment, the humanized and monoclonal antibody, the chimeric protein or the pharmaceutical composition is for preventing or limiting the interaction in vivo in a subject in need thereof. In another embodiment, the humanized and monoclonal antibody, the chimeric protein or the pharmaceutical composition is for preventing the formation or the growth of a thrombus in the subject in need thereof. In another embodiment, the humanized and monoclonal antibody, the chimeric protein or the pharmaceutical composition is for reducing the size of a thrombus or the number of thrombi in the subject in need thereof. In some embodiments, the presence, the location and/or the size of the thrombus was previously determined in the subject. In yet another embodiment, the subject is at risk of experiencing or has experienced a pathological thrombosis. In yet another embodiment, the subject is at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or vascular inflammation. In some embodiments, the humanized and monoclonal antibody, the chimeric protein or the pharmaceutical composition is for reducing or limiting tumor metastasis in the subject in need thereof. In further embodiment, the tumor metastasis are liver tumor metastasis. In yet another embodiment, the presence, the location and/or the size of the tumor metastasis have previously been determined in the subject.

In a sixth aspect, the present disclosure provides a humanized antibody described herein, a chimeric protein described herein or a pharmaceutical composition for preventing or limiting the interaction between glycoprotein I(b)α (GPIbα) present on a platelet and von Willebrand factor (VWF) and/or thrombin. In some embodiments, the humanized and monoclonal antibody, the chimeric protein or the pharmaceutical composition is for preventing or limiting platelet activation. In a specific embodiment, the humanized antibody, the chimeric protein or the pharmaceutical composition is for contacting with the platelet prior to, at the same time or after the VWF and/or thrombin as well as other GPIbα ligands is contacted with the platelet. In a specific embodiment, the humanized antibody, the chimeric protein or the pharmaceutical composition is for contacting with the platelet at a low or a high shear rate. In a further embodiment, the humanized and monoclonal antibody, the chimeric protein or the pharmaceutical composition is for preventing or limiting the interaction in vivo in a subject in need thereof. In another embodiment, the humanized and monoclonal antibody, the chimeric protein or the pharmaceutical composition is for preventing the formation or the growth of a thrombus in the subject in need thereof. In another embodiment, the humanized and monoclonal antibody, the chimeric protein or the pharmaceutical composition is for reducing the size of a thrombus or the number of thrombi in the subject in need thereof. In some embodiments, the presence, the location and/or the size of the thrombus was previously determined in the subject. In yet another embodiment, the subject is at risk of experiencing or has experienced a pathological thrombosis. In yet another embodiment, the subject is at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or vascular inflammation. In some embodiments, the humanized and monoclonal antibody, the chimeric protein or the pharmaceutical composition is for reducing or limiting tumor metastasis in the subject in need thereof. In further embodiment, the tumor metastasis are liver tumor metastasis. In yet another embodiment, the presence, the location and/or the size of the tumor metastasis have previously been determined in the subject.

BRIEF DESCRIPTION OF THE DRAWINGS

Having thus generally described the nature of the invention, reference will now be made to the accompanying drawings, showing by way of illustration, a preferred embodiment thereof, and in which:

(FIG. 7A) SPR data of 25 μL injections of 500, 100, 50 and 10 nM H001 fit to the kinetics binding model producing: $k_a$ (on rate)=$2.61 \times 10^7$ s$^{-1}$; $k_d$ (off rate)=$1.1 \times 10^{-1}$ s$^{-1}$; and $K_d$ (dissociation or binding constant)=4.4 nM. (FIG. 7B) Dose response curve of the SPR response of 25 μL injections of 500, 100, 50 and 10 nM of the purified Fab H001 plotted against ligand concentration. The curve was fit to a one-site ligand binding model producing a fit $R^2$=0.9929 and a $K_d$=8.0±2.1 nM.

(FIG. 10A) Representative photographs showing the platelet thrombus formation after heparinized-human whole blood were perfused for 1, 2, and 3 minutes, which were treated with a control PBS buffer (top panels) and the humanized Fab H001 antibody (5 μg/mL, bottom panels) at low shear (300 s⁻) condition. (FIG. 10B) Representative photographs showing the platelet thrombus formation after heparinized-human whole blood were perfused for 1, 2, and 3 minutes, which were treated with a control PBS buffer (top panels)

and the humanized Fab H001 antibody (2.5 μg/mL, middle panels and 5 μg/mL, bottom panels) at high shear (1800 s⁻) condition. (FIG. 10C) Representative photographs showing the platelet thrombus formation after heparinized-human whole blood were perfused for 1, 2, and 3 minutes, which were treated with a control PBS buffer (top panels) and the humanized Fab H002 antibody (5 μg/mL, bottom panels) at low shear (300 s⁻) condition. (FIG. 10D) Representative photographs showing the platelet thrombus formation after heparinized-human whole blood were perfused for 1, 2, and 3 minutes, which were treated with a control PBS buffer (top panels) and the humanized Fab H002 antibody (2.5 μg/mL, middle panels and 5 μg/mL, bottom panels) at high shear (1800 s⁻) condition.

(FIG. 11A) Histogram showing the time to occlusion (in minutes) in function of the antibody or the dose used.

(FIG. 12A) Histogram showing the platelet mean fluorescence intensity (MFI; the shadow part shown the SD) in function of time upon laser injury when the animals received a control treatment (top) or the H001 antibody (bottom, dose of 5 μg). (FIG. 12B) Histogram showing the platelet mean fluorescence intensity (MFI) in function of time upon laser injury when the animals received a control treatment (top) or the H002 antibody (bottom, dose of 5 μg). (FIG. 12C) Histogram showing the platelet mean fluorescence intensity (MFI) in function of time upon laser injury. The animals received a control treatment (top) or the H002 antibody (bottom, dose of 10 μg) 24 hours before injury.

(FIG. 14A) Representative photographs showing mice carotid flow (mL/min) when the animals received a control treatment (top panel), or the Fab H001 antibody (middle panel, dose of 10 μg) treatment, or the Fab H002 antibody (bottom panel, dose of 10 μg) treatment 5 minutes before injury. The arrows indicated time when vessel occlusion.

(FIG. 15A) Histogram showing the ischemic brain infarct area in function of the antibody or the doses used immediately after induction of tMCAO. (FIG. 15B) Histogram showing the ischemic brain infarct area in function of the humanized Fab H002 (dose of 100 μg) treatment after 1 hour of tMCAO. (FIG. 15C) Representative photographs of multiple 2 mm-thick coronal brain sections cut from a whole brain 24 hours after induction of tMCAO in a shame group (without inserting filament), or in a control group treated with a PBS control (200 μL), or in the treatment groups treated with the humanized Fab H001 antibody (100 μg/mouse), or H002 antibody (100 μg/mouse and 50 μg/mouse), respectively immediately after tMCAO. The white color area indicates the infarct brain. *P<0.05, **P<0.01.

(FIG. 16A) Representative photographs showing platelet thrombus accumulation in ADAMTS13⁻/⁻ mice with and without H001 or C100-scFv-HSA treatment. ADAMTS13⁻/⁻ mice were injected with fluorescently labeled platelets from mice of the same genotype, and their mesenteric vessels were then exposed and treated with calcium ionophore to induce VWF secretion. Platelet accumulation in the vessels was monitored microscopically. Sequential images taken at the indicated times after the application of calcium ionophore to ADAMTS13–/– mice (control) or with the prophylactic treatment of H001 or C100-scFv-HSA. (FIG. 16B) Histogram showing number of emboli (platelet thrombi larger than 20 μm in diameter) in ionophore-provoked ULVWF-mediated microvascular thrombosis in a mouse model of TTP.

DETAILED DESCRIPTION

Anti-GPIbα Antibodies

Figure 1:
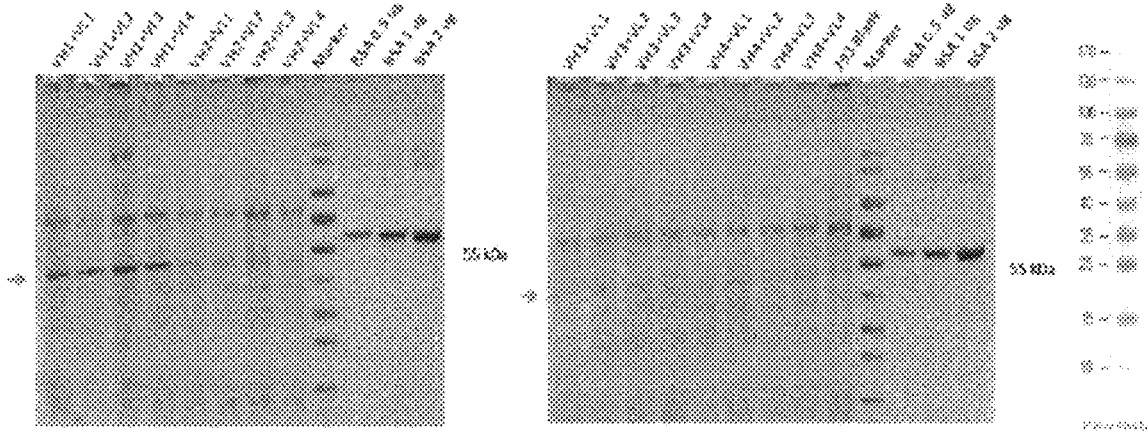
FIG. 1 shows the results of a SDS-PAGE of humanized Fabs in supernatants under non-reducing conditions. The different combinations of heavy and light chains are indicated above the gel. The molecular weight ladder (in KDa) is shown on the left. The arrows point to the humanized Fabs. Bovine serum albumin (BSA) was used as a control.

U.S. Pat. No. 8,323,652 describes that the murine NIT mAbs (NIT-A1, NIT-B1, and NIT-F1), which were generated by immunizing the GPIbα-deficient BALB/c mice with wild-type platelets, could specifically recognize both the human and the mouse GPIbα, markedly inhibited ristocetin-induced platelet aggregation and thrombus formation. However, as shown in the Examples below, these intact mAbs could induce severe thrombocytopenia. Furthermore, because they are of mouse origin, they are immunogenic in humans.

The present disclosure provides for specific antibodies against the GPIbα polypeptide. The antibodies are considered "specific" to the GPIbα polypeptide because their affinity for the GPIbα polypeptide is higher than for other polypeptides (for example other platelet surface polypeptides). The antibodies of the present disclosure can recognize and bind to the human GPIbα polypeptide (as described in Gene ID: 2811), the mouse GPIbα polypeptide (as described in Gene ID: 110331805 as well as Gene ID: 110304274), the rat GPIbα polypeptide (as described in Gene ID: 691992), the monkey GPIbα polypeptide (Gene ID: 721584), the dog GPIbα polypeptide (Gene ID: 403638) and/or the rabbit GPIbα polypeptide (Gene ID: 100349951). In an embodiment, the antibodies of the present disclosure can recognize and bind to the human GPIbα polypeptide (as described in Gene ID: 2811), the mouse GPIbα polypeptide (as described in Gene ID: 110331805 as well as Gene ID: 110304274), the rat GPIbα polypeptide (as described in Gene ID: 691992), the monkey GPIbα polypeptide (Gene ID: 721584), the dog GPIbα polypeptide (Gene ID: 403638) and/or the rabbit GPIbα polypeptide (Gen ID: 100349951).

In an embodiment, the humanized antibodies of the present disclosure have a dissociation constant ($K_D$) with the human GP1bα of 10 µM, 10 nM, 10 µM or lower. In some embodiments, the dissociation constant ($K_D$) of the humanized antibodies with the human GP1bα is 9, 8, 7, 6, 5, 4, 3, 2, 1 µM or lower. In some embodiments, the dissociation constant ($K_D$) of the humanized antibodies with the human GP1bα is 9, 8, 7, 6, 5, 4, 3, 2, 1 nM or lower. In some embodiments, the dissociation constant ($K_D$) of the humanized antibodies with the human GP1bα is 9, 8, 7, 6, 5, 4, 3, 2, 1 µM or lower.

The antibodies of the present disclosure are "humanized" antibodies because they include both a region derived from a human antibody or immunoglobulin and a region derived from a non-human antibody or immunoglobulin. The action of humanizing an antibody consists in substituting a portion of a non-human antibody with a corresponding portion of a human antibody. For example, a humanized antibody as used herein could comprise a non-human origin variable region (such as a region derived from a murine (e.g., mouse) antibody) capable of specifically recognizing GPIbα and a human framework region derived from a human antibody. In another example, the humanized immunoglobulin can comprise a heavy chain and a light chain, wherein the light chain comprises one or more complementarity determining regions (or CDR) derived from an antibody of non-human origin which binds to the GPIbα polypeptide and a framework region (or FR) derived from a light chain of human origin, and the heavy chain comprises a complementarity determining region derived from an antibody of non-human origin which binds to the GPIbα polypeptide and a framework region derived from a heavy chain of human origin. A "complementary determining region" or "CDR" refers to a region of the immunoglobulin located in the variable parts of the polypeptide and involved in specifically binding the epitope. The combination of CDRs constitutes the paratope of the antibody.

The human region of the humanized antibody can be derived from an IgG, IgM, IgA, IgE or IgD isotype. In some embodiments, the human region of the humanized antibody can be derived from an IgG isotype, for example, from the IgG1, IgG2, IgG3 or IgG4 subclass. In some specific embodiments, the human region of the humanized antibody can be derived from the IgG1 subclass. As indicated below, because the humanized antibodies are also monovalent antibodies, the human region of the humanized antibody can include a heavy chain which is derived from a $CH_1$ region and/or a $V_H$ region (excluding the CDRs) and exclude the $CH_2$ and/or $CH_3$ region. The human region of the humanized antibodies can include a light chain which is derived from a $C_L$ region and/or a $V_L$ region (excluding the CDRs). The human region of the humanized antibodies includes a light chain which can be of the kappa or lambda type. In a specific embodiment, the human region of the humanized antibody includes a light chain which is from the kappa type.

The humanized antibodies of the present disclosure do not include (e.g., lack) a Fc moiety. For example, the humanized antibody moiety is the fragment antigen-binding region $F(ab)_2$ of a multivalent antibody. The $F(ab)_2$ fragment is a dimer of two molecular entities (a light chain fragment and a heavy chain fragment), consists of a single antigen-binding site and comprises one constant and one variable domain from each heavy and light chain of the antibody which are associated to one another by disulfide bonds. Each chain of the $F(ab)_2$ includes three $V_L$ and three $V_H$ domains. The $F(ab)_2$ antibody moiety can be fully or partially glycosylated, when compared to the parent multivalent antibody it can be derived from.

In some embodiments, the antibodies of the present disclosure are "monovalent" antibodies. As used in the context of the present disclosure, a "monovalent" antibody contains a single antigen binding site. The monovalent antibody moiety has no more than one variable light domains ($V_L$) associated (covalently or not) and no more than one corresponding variable heavy domains ($V_H$). This is different with multivalent full-length antibodies which comprises at least two antigen binding sites and more than one $V_H$ and more than one $V_L$ domains. The monovalent antibody moiety can be fully or partially glycosylated, when compared to the parent multivalent antibody it can be derived from. In some instances, the monovalent antibody moiety is not glycosylated. The monovalent antibody moiety is capable of competing for the binding site that is recognized by the corresponding multivalent antibody (e.g., NIT-B1 in some embodiments). The monovalent antibody moiety does not include the crystallizable fragment (Fc fragment) of the multivalent antibody it is derived from.

In some instances, the monovalent antibody is a single-chain variable fragment (scFv) derived from one or more multivalent antibody. The scFv is single molecular entity (a fusion protein) consisting of a single antigen-binding region and having no more than one $V_H$ and no more than one $V_L$ domains from a multivalent antibody which are connected with a linker (e.g., usually a short peptide linker). As such, the scFv consists of a single antigen-binding region and comprises one $V_H$ and one $V_L$ domains. The scFv can be obtained from screening a synthetic library of scFvs, such as, for example, a phage display library of scFvs. The scFvs of the present disclosure can include, for example, one or more GGGGS (SEQ ID NO: 92) linker between the $V_H$ and the $V_L$ domains. In some embodiments, the carboxy terminus of the $V_L$ domain can be linked to the amino terminus of the $V_H$ domain. In another embodiment, the carboxy terminus of the $V_H$ domain can be linked to the amino terminus of the $V_L$ domain. In some embodiments, the scFvs of the present disclosure can include a purification tag (such as, for example a 6×His tag) which can be removed once the scFv is purified. In some additional embodiments, the scFv can be (covalently) associated with a carrier protein to form chimeric protein. In such embodiments, the carrier protein can be linked at the amino terminus or the carboxy terminus of the scFv. In some embodiments, the scFv does not include a purification tag or has been processed to remove a purification tag.

In other instances, the monovalent antibody is the fragment antigen-binding region (Fab) of a multivalent (and in some embodiments, monoclonal) antibody. The Fab fragment comprises two molecular entities (a light chain fragment and a heavy chain fragment), consists of a single antigen-binding site and comprises one constant and one variable domain from each heavy and light chain of the antibody which are associated to one another by disulfide bonds. The Fab includes a single $V_L$ and a single $V_H$ domain.

In further instances, the monovalent antibody is a single domain antibody or a nanobody. The single domain antibody includes a single monomeric variable antibody domain comprising at least three complementary determining regions (CDRs). The single domain antibodies can be obtained from camelids (e.g., $V_HH$ antibodies), from fish (e.g. $V_{NAR}$ antibodies) or from phage display. The single domain antibodies can be derived from a heavy chain or a light chain. The single domain antibodies can be humanized.

The antibodies of the present disclosure can be capable of preventing platelet activation and aggregation. The expression "capable of preventing platelet activation and aggregation" refers to the ability of the humanized antibodies of the present disclosure to, in the presence of a platelet and a platelet agonist, avoid activating the platelet and aggregating platelets. Platelet activation occurs primarily during the initiation of the hemostasis or thrombosis. Upon activation, platelets change their shape and release the content of their granules. Activated platelets modulate the expression of their membrane proteins (e.g., P-selectin), lipids (e.g., phosphatidylserine) and conformational changes of platelet αIIbβ3 integrin that results in platelet aggregation. Platelet activation and aggregation can be measured, for example, by determining the shape of the platelet, the level of aggregation of platelets (using for example an aggregometer), the expression of surface protein or lipids, etc. Platelets can be activated with the following agonists (activators), thrombin, ADP, collagen and others. Ristocetin can also cause von Willebrand factor to bind to platelet receptor GPIbα. In order to determine if a humanized antibody prevents platelet activation and aggregation, platelets (which can be obtained in the form of platelet-rich plasma or gel-filtered platelets for example) can be placed in contact with the humanized antibody first and then with the agonist. Then, it should be determined, by methods known in the art, if the platelets are activated/aggregated or not. Antibodies preventing platelet activation and aggregation are considered to be antibodies of the present disclosure.

In addition, the humanized antibodies of the present disclosure can lack the ability to induce platelet activation. The expression "lack the ability to induce platelet activation" refers to one of the properties of the humanized antibodies of the present disclosure, namely that they do not activate platelets in the absence of a known platelet agonist.

In order to determine if a humanized antibody lacks the ability to induce platelet activation, platelets (which can be obtained in the form of platelet-rich plasma or gel-filtered platelets for example) can be placed in contact with the antibody (in the absence of a known platelet agonist) and then, it should be determined, by methods known in the art, if the platelets are activated or not. Antibodies that fail to induce platelet activation are considered to be antibodies of the present disclosure.

The antibodies of the present disclosure can lack the ability to induce thrombocytopenia. The expression "lack the ability to induce thrombocytopenia" refers to one of the properties of the humanized antibodies of the present disclosure, namely that they do not cause a substantial and pathological deficiency in the total number of platelets. In humans, thrombocytopenia requiring emergency treatment is a count below 50,000 platelets per μL of blood. In order to determine if a humanized antibody lacks the ability to induce thrombocytopenia, it is administered to a test subject (a mouse for example) and the level of platelets is monitored using techniques known in the art to determine if the antibody causes a decrease (and if so a substantive or pathological decrease) in platelet count. Antibodies that fail to induce thrombocytopenia are considered to be antibodies of the present disclosure.

The antibodies of the present disclosure can lack the ability to prolong bleeding time (at therapeutic doses). The expression "lack the ability to prolong bleeding time" refers to one of the properties of the humanized antibodies of the present disclosure, namely that they do not cause a substantial and pathological increasing the time it takes to stop bleeding. In order to determine if a humanized antibody lacks the ability to prolong bleeding time, a cut (of standardized width and depth) is made on the tail of a test subject (a mouse for example), the time it takes for the bleeding to stop (e.g., cessation of blood flow for a minimal amount of time) is determined using techniques known in the art (in some embodiments, the Ivy method or Duke method) and compared to a standard to ascertain if the antibody causes an increase (and if so a substantive increase) in bleeding time. Antibodies that fail prolonging bleeding time at doses indicated are considered to be antibodies of the present disclosure.

The antibodies of the present disclosure can also be capable of antagonizing the biological activity of the GPIbα polypeptide. The GPIbα polypeptide is a platelet surface membrane glycoprotein serving as a receptor for the von Willebrand factor (VWF), thrombin as well as other ligands. By antagonizing its biological activity, the antibodies of the present disclosure can thus be used to limit or prevent platelet activation and aggregation (especially under high shear conditions).

Antibodies of the present disclosure can be derived from monoclonal antibodies. Antibodies which are specific for a single epitope on the GPIbα polypeptide are considered as monoclonal antibodies (also referred to as mAbs). In some embodiments, monoclonal antibodies are produced from a single clone of an immune cell. Monoclonal antibodies can be produced by techniques known in the art, such as by using cell culture by fusing a myeloma cell to a spleen cell from a subject (such as a mouse or a human) which has been immunized with an antigen comprising the epitope of the GPIbα polypeptide. Monoclonal antibodies can also be obtained phage display by screening library of monoclonal antibodies using an antigen comprising the epitope of the GPIbα polypeptide. Additional techniques for making monoclonal antibodies include, but are not limited to single B cell culture, single cell amplification from B cell populations. Monoclonal antibodies of the present disclosure can be from various origins (e.g., mouse or human for example) and can include two identical light chains and two identical heavy chains, wherein each chain comprises three CDRs. Monoclonal antibodies can be from any isotype, including, but not limited to immunoglobulin A (IgA), IgD, IgE, IgG (including subtypes IgG1, IgG2, IgG3 or IgG4) or IgM. Monoclonal antibodies can be, in an embodiment, from the IgG isotype.

In an embodiment, the antibodies of present disclosure have at least one complementary determining region comprising or consisting essentially of the amino acid sequence of SEQ ID NO: 37, 38, 39, 65, 66 or 67, variant thereof or fragments thereof. In the context of the present disclosure, and especially when referred to the amino acid sequence of CDR, the expression "consisting essentially of" indicates that the CDR necessarily comprises the amino acid sequence of SEQ ID NO: 37, 38, 39, 65, 66 or 67, but that additional, non-essential, amino acid residues can be added at the amino or the carboxyl end of those sequences (as long as these amino acid residues do not substantially modify the affinity of the antibody for the GPIbα polypeptide or its ability to antagonize the biological activity of the GPIbα polypeptide).

In an embodiment, the antibodies of the present disclosure have at least two complementary determining region comprising or consisting essentially of the amino acid sequence of SEQ ID NO: 37, 38, 39, 65, 66 or 67, variant thereof or fragments thereof. In still another embodiment, the antibodies of the present disclosure have at least three complementary determining region comprising or consisting essentially of the amino acid sequence of SEQ ID NO: 37, 38, 39, 65, 66 or 67, variant thereof or fragments thereof. In yet another embodiment, the antibodies of the present disclosure have at least four complementary determining region comprising or consisting essentially of the amino acid sequence of SEQ ID NO: 37, 38, 39, 65, 66 or 67, variant thereof or fragments thereof. In still another embodiment, the antibodies of the present disclosure have at least five complementary determining region comprising or consisting essentially of the amino acid sequence of SEQ ID NO: 37, 38, 39, 65, 66 or 67, variant thereof or fragments thereof. In still another embodiment, the antibodies of the present disclosure have complementary determining region comprising or consisting essentially of the amino acid sequence of SEQ ID NO: 37, 38, 39, 65, 66 and 67, variant thereof or fragments thereof.

In some embodiments, the antibodies of the present disclosure have the complementary determining region comprising or consisting essentially of the amino acid sequence of SEQ ID NO: 37, 38 and 39 (including variants and fragments) as well as at least one complementary determining region comprising or consisting essentially or SEQ ID NO: 65, 66 or 67 (including variants and fragments). In some additional embodiments, the antibodies of the present disclosure have the complementary determining region comprising or consisting essentially of the amino acid sequence of SEQ ID NO: 37, 38 and 39 (including variants and fragments) as well as at least two complementary determining region comprising or consisting essentially or SEQ ID NO: 65, 66 or 67 (including variants and fragments). In some further embodiments, the antibodies of the present disclosure have the complementary determining region comprising or consisting essentially of the amino acid sequence of SEQ ID NO: 65, 66 and 67 (including variants and fragments) as well as at least one complementary determining region comprising or consisting essentially or SEQ ID NO: 37, 38 or 39 (including variants and fragments). In some additional embodiments, the antibodies of the present disclosure have the complementary determining region comprising or consisting essentially of the amino acid sequence of SEQ ID NO: 65, 66 and 67 (including variants and fragments) as well as at least two complementary determining region comprising or consisting essentially or SEQ ID NO: 37, 38 or 39 (including variants and fragments).

The antibody of the present disclosure can include a functional variant of a CDR having the amino acid sequence of SEQ ID NO: 37, 38, 39, 65, 66 or 67. A variant CDR comprises at least one amino acid difference when compared to the amino acid sequence of the CDR. As used herein, a variant refers to alterations in the amino acid sequence that do not adversely affect the biological functions of the antibody (e.g., providing specificity and affinity towards the GPIbα polypeptide). In some embodiments, the overall charge, structure or hydrophobic-hydrophilic properties of the antibody can be altered without adversely affecting a biological activity. Accordingly, the amino acid sequence of the CDR can be altered, for example to render the antibody more hydrophobic or hydrophilic, without adversely affecting the biological activities of the antibody. The CDR variants have at least 50%, 55%, 60%, 65%, 70%, 75%, 80%, 85%, 90%, 95%, 96%, 97%, 98% or 99% identity to the CDRs described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The CDR variants may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group. A "variant" of the CDR can be a conservative variant or an allelic variant.

The antibody of the present disclosure can include a functional fragment of a CDR having the amino acid sequence of SEQ ID NO: 37, 38, 39, 65, 66 or 67. A fragment of a CDR comprises at least one less amino acid residue compared to the amino acid sequence of the CDR. The CDR fragments comprise some consecutive amino acid residues of the CDR of amino acid sequence of SEQ ID NO: 37, 38, 39, 65, 66 or 67. The CDR fragments have at least 50%, 55%, 60%, 65%, 70%, 75%, 80%, 85%, 90%, 95%, 96%, 97%, 98% or 99% identity to the CDRs described herein.

In another embodiment, the antibodies of the present disclosure comprise a heavy chain and the heavy chain comprises at least one CDR comprising or consisting essentially of an amino acid sequence of SEQ ID NO: 37, 38 or 39, functional variants thereof and functional fragments thereof. In a further embodiment, the heavy chain comprises at least two CDRs each comprising or consisting essentially of a distinct amino acid sequence from the following: SEQ ID NO: 37, 38 or 39, functional variants thereof and functional fragments thereof. In still a further embodiment, the heavy chain comprises three CDRs each comprising or consisting essentially of a distinct amino acid sequence from the following: SEQ ID NO: 37, 38 and 39 functional variants thereof and functional fragments thereof.

In another embodiment, the heavy chain includes a CH1 region of a human IgG1 antibody and comprises the amino acid sequence of SEQ ID NO: 40, 47, 54 or 61, functional variants thereof as well as functional fragments thereof. As used in the context of the present disclosure, a functional variant of a CH1 region of a human IgG1 antibody refers to alterations in the amino acid sequence that do not adversely affect the biological functions of the antibody (e.g., providing specificity and affinity towards the GPIbα polypeptide). In an embodiment, the functional variant of the CH1 region of the human IgG1 antibody has at least 50%, 55%, 60%, 65%, 70%, 75%, 80%, 85%, 90%, 95%, 96%, 97%, 98% or 99% identity to the CH1 region described herein (such as, for example, those having the amino acid sequence of SEQ ID NO: 40, 47, 54 or 61). As also used in the context of the present disclosure, a functional fragment of a CH1 region of a human IgG1 antibody refers to comprises at least one less amino acid residue compared to the amino acid sequence of the CH1 region of the human IgG1 antibody that do not adversely affect the biological functions of the antibody (e.g., providing specificity and affinity towards the GPIbα polypeptide). In an embodiment, the functional fragment of the CH1 region of the human IgG1 antibody has at least 50%, 55%, 60%, 65%, 70%, 75%, 80%, 85%, 90%, 95%, 96%, 97%, 98% or 99% identity to the CH1 region described herein (such as, for example, those having the amino acid sequence of SEQ ID NO: 40, 47, 54 or 61).

In some embodiments, the heavy chain comprises or consists essentially of the amino acid sequence of SEQ ID NO: 36, 43, 50 or 57, functional variants thereof and functional fragments thereof. In the context of the present disclosure, and especially when referred to the amino acid sequence of the heavy chain, the expression "consisting essentially of" indicates that the heavy chain necessarily comprises the amino acid sequence of SEQ ID NO: 36, 43, 50 or 57, but that additional, non-essential, amino acid residues can be added at the amino or the carboxyl end of those sequences (as long as these amino acid residues do not substantially modify the affinity of the antibody for the GPIbα polypeptide or its ability to antagonize the biological activity of the GPIbα polypeptide). As used in the context of the present disclosure, a functional variant of the heavy chain antibody refers to alterations in the amino acid sequence that do not adversely affect the biological functions of the antibody (e.g., providing specificity and affinity towards the GPIbα polypeptide). In an embodiment, the functional variant of the heavy chain has at least 50%, 55%, 60%, 65%, 70%, 75%, 80%, 85%, 90%, 95%, 96%, 97%, 98% or 99% identity to the heavy chain described herein (such as, for example, those having the amino acid sequence of SEQ ID NO: 36, 43, 50 or 57). As also used in the context of the present disclosure, a functional fragment of the heavy chain comprises at least one less amino acid residue compared to the amino acid sequence of the heavy chain that do not adversely affect the biological functions of the antibody (e.g., providing specificity and affinity towards the GPIbα polypeptide). In an embodiment, the functional fragment of the heavy chain has at least 50%, 55%, 60%, 65%, 70%, 75%, 80%, 85%, 90%, 95%, 96%, 97%, 98% or 99% identity to the heavy chain described herein (such as, for example, those having the amino acid sequence of SEQ ID NO: 36, 43, 50 or 57).

In another embodiment, the antibody comprises a light chain and the light chain comprises at least one CDR comprising or consisting essentially of an amino acid sequence of SEQ ID NO: 65, 66 or 67, functional variants thereof and functional fragments thereof. In a further embodiment, the light chain comprises at least two CDRs each comprising or consisting essentially of a distinct amino acid sequence from the following: SEQ ID NO: 65, 66 or 67, functional variants thereof and functional fragments thereof. In still a further embodiment, the light chain comprises three CDRs each comprising or consisting essentially of a distinct amino acid sequence from the following: SEQ ID NO: 65, 66 and 67, functional variants thereof and functional fragments thereof.

In another embodiment, the light chain includes a human IgG1 kappa chain C region which can have, for example, the amino acid sequence of SEQ ID NO: 68, 75, 82, or 89, the variant thereof or the fragment thereof. As used in the context of the present disclosure, a functional variant of a human IgG1 kappa chain C region refers to alterations in the amino acid sequence that do not adversely affect the biological functions of the antibody (e.g., providing specificity and affinity towards the GPIbα polypeptide). In an embodiment, the functional variant of the human IgG1 kappa chain C region has at least 50%, 55%, 60%, 65%, 70%, 75%, 80%, 85%, 90%, 95%, 96%, 97%, 98% or 99% identity to the a human IgG1 kappa chain C region described herein (such as, for example, those having the amino acid sequence of SEQ ID NO: 68, 75, 82 or 89). As also used in the context of the present disclosure, a functional fragment of a human IgG1 kappa chain C region refers to comprises at least one less amino acid residue compared to the amino acid sequence of the a human IgG1 kappa chain C region that do not adversely affect the biological functions of the antibody (e.g., providing specificity and affinity towards the GPIbα polypeptide). In an embodiment, the functional fragment of the human IgG1 kappa chain C region has at least 50%, 55%, 60%, 65%, 70%, 75%, 80%, 85%, 90%, 95%, 96%, 97%, 98% or 99% identity to the CH1 region described herein (such as, for example, those having the amino acid sequence of SEQ ID NO: 68, 75, 82 or 89).

In another embodiment, the light chain comprises or consists essentially of the amino acid sequence of SEQ ID NO: 64, 71, 78 or 85, functional variants thereof and functional fragments thereof. In the context of the present disclosure, and especially when referred to the amino acid sequence of a light chain, the expression "consisting essentially of" indicates that the light chain necessarily comprises the amino acid sequence of SEQ ID NO: 64, 71, 78 or 85, but that additional, non-essential, amino acid residues can be added at the amino or the carboxyl end of those sequences (as long as these amino acid residues do not substantially modify the affinity of the antibody for the GPIbα polypeptide or its ability to antagonize the biological activity of the GPIbα polypeptide). As used in the context of the present disclosure, a functional variant of a light chain antibody refers to alterations in the amino acid sequence that do not adversely affect the biological functions of the antibody (e.g., providing specificity and affinity towards the GPIbα polypeptide). In an embodiment, the functional variant of the light chain has at least 50%, 55%, 60%, 65%, 70%, 75%, 80%, 85%, 90%, 95%, 96%, 97%, 98% or 99% identity to the light chain described herein (such as, for example, those having the amino acid sequence of SEQ ID NO: 64, 71, 78 or 85). As also used in the context of the present disclosure, a functional fragment of a light chain comprises at least one less amino acid residue compared to the amino acid sequence of the heavy chain that do not adversely affect the biological functions of the antibody (e.g., providing specificity and affinity towards the GPIbα polypeptide). In an embodiment, the functional fragment of the light chain has at least 50%, 55%, 60%, 65%, 70%, 75%, 80%, 85%, 90%, 95%, 96%, 97%, 98% or 99% identity to the light chain described herein (such as, for example, those having the amino acid sequence of SEQ ID NO: 64, 71, 78 or 85).

In some embodiments, the heavy chain comprises or consists essentially of the amino acid sequence of SEQ ID NO: 36, 43, 50 or 57, functional variants thereof and functional fragments thereof. In the context of the present disclosure, and especially when referred to the amino acid sequence of heavy chain, the expression "consisting essentially of" indicates that the CDR necessarily comprises the amino acid sequence of SEQ ID NO: 36, 43, 50 or 57, but that additional, non-essential, amino acid residues can be added at the amino or the carboxyl end of those sequences (as long as these amino acid residues do not substantially modify the affinity of the antibody for the GPIbα polypeptide or its ability to antagonize the biological activity of the GPIbα polypeptide). As used in the context of the present disclosure, a functional variant of heavy chain antibody refers to alterations in the amino acid sequence that do not adversely affect the biological functions of the antibody (e.g., providing specificity and affinity towards the GPIbα polypeptide). In an embodiment, the functional variant of the heavy chain has at least 50%, 55%, 60%, 65%, 70%, 75%, 80%, 85%, 90%, 95%, 96%, 97%, 98% or 99% identity to the heavy chain described herein (such as, for example, those having the amino acid sequence of SEQ ID NO: 36, 43, 50 or 57). As also used in the context of the present disclosure, a functional fragment of a heavy chain comprises at least one less amino acid residue compared to the amino acid sequence of the heavy chain that do not adversely affect the biological functions of the antibody (e.g., providing specificity and affinity towards the GPIbα polypeptide). In an embodiment, the functional fragment of the heavy chain has at least 50%, 55%, 60%, 65%, 70%, 75%, 80%, 85%, 90%, 95%, 96%, 97%, 98% or 99% identity to the heavy chain described herein (such as, for example, those having the amino acid sequence of SEQ ID NO: 36, 43, 50 or 57).

In yet another embodiment, the antibody can comprise both a heavy chain and the light chain. In such embodiment, the humanized antibody can have the heavy chain of SEQ ID NO: 36, the variant thereof or the fragment thereof and the light chain of SEQ ID NO: 64, the variant thereof or the fragment thereof. In another embodiment, the humanized antibody can have the heavy chain of SEQ ID NO: 36, the variant thereof or the fragment thereof and the light chain of SEQ ID NO: 64, the variant thereof or the fragment thereof. In still another embodiment, the humanized antibody can have the heavy chain of SEQ ID NO: 36, the variant thereof or the fragment thereof and the light chain of SEQ ID NO: 71, the variant thereof or the fragment thereof. In yet another embodiment, the humanized antibody can have the heavy chain of SEQ ID NO: 36, the variant thereof or the fragment thereof and the light chain of SEQ ID NO: 78, the variant thereof or the fragment thereof. In another embodiment, the humanized antibody can have the heavy chain of SEQ ID NO: 36, the variant thereof or the fragment thereof and the light chain of SEQ ID NO: 85, the variant thereof or the fragment thereof. In still another embodiment, the humanized antibody can have the heavy chain of SEQ ID NO: 43, the variant thereof or the fragment thereof and the light chain of SEQ ID NO: 64, the variant thereof or the fragment thereof. In yet another embodiment, the humanized antibody can have the heavy chain of SEQ ID NO: 43, the variant thereof or the fragment thereof and the light chain of SEQ ID NO: 71, the variant thereof or the fragment thereof. In yet a further embodiment, the humanized antibody can have the heavy chain of SEQ ID NO: 43, the variant thereof or the fragment thereof and the light chain of SEQ ID NO: 78, the variant thereof or the fragment thereof. In a further embodiment, the humanized antibody can have the heavy chain of SEQ ID NO: 43, the variant thereof or the fragment thereof and the light chain of SEQ ID NO: 85, the variant thereof or the fragment thereof. In a further embodiment, the humanized antibody can have the heavy chain of SEQ ID NO: 50, the variant thereof or the fragment thereof and the light chain of SEQ ID NO: 64, the variant thereof or the fragment thereof. In a further embodiment, the humanized antibody can have the heavy chain of SEQ ID NO: 50, the variant thereof or the fragment thereof and the light chain of SEQ ID NO: 71, the variant thereof or the fragment thereof. In yet a further embodiment, the humanized antibody can have the heavy chain of SEQ ID NO: 50, the variant thereof or the fragment thereof and the light chain of SEQ ID NO: 78, the variant thereof or the fragment thereof. In still another embodiment, the humanized antibody can have the heavy chain of SEQ ID NO: 50, the variant thereof or the fragment thereof and the light chain of SEQ ID NO: 85, the variant thereof or the fragment thereof. In an embodiment, the humanized antibody can have the heavy chain of SEQ ID NO: 57, the variant thereof or the fragment thereof and the light chain of SEQ ID NO: 64, the variant thereof or the fragment thereof. In still a embodiment, the humanized antibody can have the heavy chain of SEQ ID NO: 57, the variant thereof or the fragment thereof and the light chain of SEQ ID NO: 71, the variant thereof or the fragment thereof. In yet another embodiment, the humanized antibody can have the heavy chain of SEQ ID NO: 57, the variant thereof or the fragment thereof and the light chain of SEQ ID NO: 78, the variant thereof or the fragment thereof. In still a further embodiment, the humanized antibody can have the heavy chain of SEQ ID NO: 57, the variant thereof or the fragment thereof and the light chain of SEQ ID NO: 85, the variant thereof or the fragment thereof.

The heavy and light chains of the antibodies of the present disclosure can include a leader sequence which, upon secretion from the cell, is cleaved. For example, the amino acid sequence of SEQ ID NO: 35 includes the amino acid sequence of SEQ ID NO: 36 as well as additional amino acid residues at the N terminus which act as a leader sequence. The leader sequence which can be included in the heavy and/or light chain includes, but are not limited to the amino acid sequence of SEQ ID NO: 91.

In some embodiment, the antibodies of the present disclosure may be further modified or designed into a chimeric protein (comprising a carrier protein) to increase, amongst other things, their circulation half-life. The humanized antibody moiety can be associated (directly or indirectly with the linker, such as, for example one or more GGGGS (SEQ ID NO: 92) linker) to the carrier at any amino acid residue(s), provided that the association does not impede the humanized antibody moiety from binding to GPIbα and inhibiting its biological activity. In an embodiment, the linker includes three copies of the GGGGS (SEQ ID NO: 92) linker. In another embodiment, the linker includes four copies of the GGGGS (SEQ ID NO: 92) linker. In some instances, the linker (when present) or the carrier is associated to one or more amino acid residue(s) of the humanized antibody moiety that is (are) not involved in specifically binding to GPIbα and inhibiting its biological activity. In some instances, the linker or the carrier is associated to a single amino acid residue of the humanized antibody moiety. The linker or the carrier can be associated with any amino acid residue of the humanized antibody moiety, including the amino acid residue located at the amino-terminus of the humanized antibody moiety or at the carboxyl-terminus of the humanized antibody moiety. In some embodiments, the carrier protein can be located upstream (at the amino end) or downstream (at the carboxy end) of the humanized antibody moiety. In instances in which the linker and the carrier are also of proteinaceous nature, the humanized antibody moiety can be associated to any amino acid residue of the linker or the carrier, including the amino acid residue located at the amino-terminus of the linker or the carrier or the amino acid residue located at the carboxyl-terminus of the linker or the carrier. In an embodiment, the amino acid residue located at the amino-terminus of the linker or the carrier is associated to the amino acid residue located at the carboxyl-terminus of the humanized antibody moiety. In still another embodiment, when the linker is present and is of protaneicous nature, its amino terminus is associated to the carboxyl terminus of humanized antibody and its carboxyl terminus is associated with the amino terminus of the carrier. In an embodiment, the carrier protein is albumin (e.g., human serum albumin for example). In an embodiment, the carrier comprises one or more further antibody or an antibody fragment.

In instances where a covalent association is sought between the humanized antibody moiety and the carrier, the association between the two entities can be a peptidic bond. Such embodiment is especially useful for chimeric proteins wherein the at least two entities are both proteinaceous and are intended to be produced as a fusion protein in an organism (prokaryotic or eukaryotic) using a genetic recombinant technique. Alternatively, the covalent association between the two moieties can be mediated by any other type of chemical covalent bounding. In some instances, the chimeric proteins are designed so as not to be susceptible of being cleaved into the two moieties in the general circulation (for example in plasma).

As indicated above, the association between the two entities (e.g., humanized antibody moiety and carrier moiety) can be non-covalent. Exemplary non-covalent associations include, but are not limited to the biotin-streptavidin/avidin system. In such system, a label (biotin) is covalently associated to one entity/moiety while a protein (streptavidin or biotin) is covalently associated with the other entity/moiety. In such embodiment, the biotin can be associated to the humanized antibody moiety or to the carrier, providing that the other entity in the system is associated with streptavidin or avidin.

In a further system of non-covalent association, the first entity is designed to be non-covalently associated to the second entity only upon its administration into the intended recipient. This embodiment is especially useful when the carrier is a protein present in the blood of the recipient. For example, the humanized antibody moiety may be associated (in a covalent or a non-covalent fashion) with a second antibody, a lectin or a fragment thereof (referred to herein as an antibody-derived linker) which is capable of non-covalently binding the carrier once administrated to the intended recipient. For example, the second antibody, lectin or fragment thereof can be specific for any blood/plasma protein present in the intended recipient (such as, for example, serum albumin, immunoglobulins fragments (provided that these fragments do not directly bind the activating Fc receptor or cause the chimeric protein to simultaneously bind to more than one site on the activating Fc receptor), alpha-1-acid glycoprotein, transferrin, or lipoproteins). The second antibody, lectin or fragment thereof can be associated, preferably in a covalent manner, with the humanized antibody moiety at any amino acid residue of the humanized antibody moiety, but preferably at the amino- or carboxyl-end of the humanized antibody moiety. In such embodiment, the second antibody, lectin or fragment thereof is akin to a linker between the humanized antibody moiety and the carrier. Upon the administration of this embodiment of the humanized antibody moiety in the recipient, the carrier (a blood or plasma protein for example) associates with the second antibody, lectin or fragment thereof to form, in vivo, the chimeric protein. In a specific embodiment, the second antibody is an antibody specifically recognizing albumin (such as, for example, an antibody specifically recognizing human albumin).

The present disclosure also provides nucleotide molecules encoding the antibodies described herein. The nucleotide molecules can be provided in an isolated form and may be derived from a variety of sources including DNA, cDNA, synthetic DNA, synthetic RNA, derivatives, mimetics or combinations thereof. Such sequences may comprise genomic DNA, which may or may not include naturally occurring introns, genic regions, non-genic regions, and regulatory regions. Moreover, such genomic DNA may be obtained in association with promoter regions or poly (A) sequences. The sequences, genomic DNA, or complementary DNA (cDNA) may be obtained in any of several ways. Genomic DNA can be extracted and purified from suitable cells by means well known in the art. Alternatively, mRNA can be isolated from a cell and used to produce cDNA by reverse transcription or other means. The nucleotide molecules described herein are used in certain embodiments of the methods of the present disclosure for production of RNA, proteins or polypeptides, through incorporation into host cells, tissues, or organisms. In an embodiment, the nucleotide molecules can be codon-optimized for expression in a particular host. The nucleotide molecules can include, in some embodiments, one or more promoter sequence and/or one or more terminator sequence. The nucleotide molecules can be included in a vector for expression in a recombinant host. The nucleotide molecules of the present disclosure can include, in some embodiments, the nucleic acid sequence of SEQ ID NO: 41, 48, 55, 62, 69, 76, 83 and/or 90. In an embodiment, the nucleotide sequence of the present disclosure includes the nucleic acid sequence of SEQ ID NO: 41 and 69, 41 and 76, 41 and 83 or 41 and 90. In another embodiment, the nucleotide sequence of the present disclosure includes the nucleic acid sequence of SEQ ID NO: 48 and 69, 48 and 76, 48 and 83 or 48 and 90. the nucleotide sequence of the present disclosure includes the nucleic acid sequence of SEQ ID NO: 55 and 69, 55 and 76, 55 and 83 or 55 and 90. the nucleotide sequence of the present disclosure includes the nucleic acid sequence of SEQ ID NO: 62 and 69, 62 and 76, 62 and 83 or 62 and 90.

Therapeutic Uses of the Humanized Antibodies

Since platelet GPIbα and its ligands (such as VWF) interactions have been recognized as important players in the pathogenesis of diverse diseases, the humanized antibodies can be used in the prevent and/or treatment of ischemic stroke, acute myocardial infarction, restenosis, angina, acute coronary syndrome, atherothrombosis, vascular inflammation, venous thrombosis, peripheral vascular disease, thrombotic thrombocytopenic purpura, sepsis and/or tumor metastasis. The humanized antibody or the chimeric protein can be used in a subject having platelets being specifically recognized by the humanized antibody (or the humanized antibody moiety of the chimeric protein). As such, the humanized antibody can be used in a mammal subject, such as, for example, a human, a monkey, a mouse, a rabbit and/or a dog, etc.

The present disclosure provides a method for preventing or limiting the physical interaction between GPIbα and its cognate ligand. The method comprises contacting the humanized antibody, the chimeric protein or the pharmaceutical composition described herein with a platelet (which expresses on its surface GPIbα) under conditions to allow the binding of the humanized antibody/humanized antibody moiety with GPIbα. As shown in the Examples below, the humanized antibodies and the chimeric proteins of the present disclosure are capable of binding to GPIbα and antagonizing its biological activity under low and high shear stress. As such, the method can be used to bind to GPIbα irrespective of the shear stress applied. The method can be used in vitro or in vivo in a subject in need thereof. The method can be used in low or high shear rates.

When it is sought to prevent the interaction between GPIbα and its ligands (such as VWF), the humanized antibody or the chimeric protein can be used prior to the contact between GPIbα and its ligand. As such, the platelet is first contacted with the humanized antibody (which is optionally presented as a chimeric protein or a pharmaceutical composition) before its ligand is placed or is found in vicinity of the platelet. In such embodiment, it is understood that the binding of the humanized antibody of the present disclosure will prevent the physical association of GPIbα with its ligand and, ultimately, prevent or limit platelet activation and aggregation.

When it is sought to limit the interaction between GPIbα and its ligands (such as VWF), the humanized antibody can be used at the same time or after the contact between GPIbα and its ligand has occurred. As such, the platelet is contacted with the humanized antibody (which is optionally presented as a chimeric protein or a pharmaceutical composition) simultaneously or after its ligand is placed or is found in vicinity of the platelet. In such embodiment, it is understood that the binding of the humanized antibody of the present disclosure will limit the physical association of GPIbα with its ligand and, in some embodiments, prevent or limit platelet activation and aggregation.

The humanized antibody (optionally in a chimeric form or in a pharmaceutical composition) can be used to prevent, treat or alleviate the symptoms associated with pathological thrombosis in a subject in need thereof. Since the humanized antibody of the present disclosure can prevent platelet activation and aggregation (at least in the Examples below), they can be used to prevent pathological thrombosis in a subject susceptible to pathological thrombosis. In addition, since the humanized antibody of the present disclosure do not induce thrombocytopenia or prolong bleeding, they are safer to use (than for example, the original monoclonal antibody they are derived from). As used in the context of the present disclosure, the term "pathological thrombosis" refers to a condition in which a thrombus (a blood clot) forms in a blood vessel and causes a damage to the surrounding tissues. The pathological thrombosis can occur in a vein or an artery. The pathological thrombus can occur or be observed in a cavernous sinus, a renal vein, a deep vein or in a lung (pulmonary embolism). In some embodiments, the humanized antibody or the chimeric protein is used to prevent, treat or alleviate the symptoms associated with pathological thrombosis under high sheer stress conditions. In the vicinity of an occluded or partially occluded vessel, shear stress is high and the interaction between GPIbα and VWF is critical for vessel occlusion.

In embodiments in which it is warranted to prevent the formation or the growth of a thrombus, the humanized antibody or the chimeric protein can be used in subject at risk of forming or growing a thrombus. In an embodiment, the method can include determining if, prior to administration of the antibody, the subject is at risk of forming or growing a thrombus (with methods and assays known in the art). The humanized antibody can be used in subject which has previously been determined to be at risk of forming or growing a thrombus. In another embodiment, the method can include determining, after the administration of at least one dose of the humanized antibody or the chimeric protein, if the subject has at least one thrombus and, in some further embodiments, the size of the thrombus. Such determination can help determine if additional doses should be administered to the subject to achieve the desired therapeutic effect.

In subjects having a plurality of thrombi, the humanized antibody or the chimeric protein can be used to reduce the size and/or the number of thrombi. In an embodiment, the method can include determining if, prior to administration of the antibody, the subject has one or more thrombus and optionally the size of the thrombus (with methods and assays known in the art). The humanized antibody can be used in a subject which has previously been determined have a plurality of thrombi and optionally the size of the thrombus. In another embodiment, the method can include determining, after the administration of at least one dose of the humanized antibody or the chimeric protein, the presence, number and size of the thrombus. Such determination can help determine if additional doses should be administered to the subject to achieve the desired therapeutic effect.

In some embodiments, the methods of the present disclosure includes determining if the subject is at risk of experiencing or has experienced a pathological thrombosis. A positive determination that the subject is at risk of experiencing or has experienced pathological thrombosis is indicative that the subject would benefit from receiving the humanized antibodies of the present disclosure. As such, the methods of the present disclosure can include administering the humanized antibody or the chimeric protein to a subject which has been determined to be at risk of experiencing or has experienced a pathological thrombosis. The humanized antibodies and the chimeric protein of the present disclosure can be used in subjects in which it has been determined that they are at risk of experiencing or has experienced a pathological thrombosis.

In some further embodiments, the methods of the present disclosure includes determining if the subject is at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or vascular inflammation. A positive determination that the subject is at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or vascular inflammation is indicative that the subject would benefit from receiving the humanized antibodies of the present disclosure. As such, the methods of the present disclosure can include administering the humanized antibody to a subject which has been determined to be at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or vascular inflammation. The humanized antibodies of the present disclosure can be used in subjects in which it has been determined that they are at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or vascular inflammation.

Because the interaction between GPIbα and VWF is important for the dissemination of tumor metastasis, the humanized antibody or the chimeric protein of the present disclosure can be used to reduce or limit tumor metastasis in a subject in need thereof. In some embodiments, the humanized antibody or the chimeric protein can be used to reduce the number of tumor metastasis and/or the size of tumor metastasis. In an embodiment, the tumor metastasis are associated with a liver cancer (such as a liver carcinoma or adenocarcinoma) and the humanized antibody can be used to reduce or limit liver tumor metastasis.

In some embodiments, the methods of the present disclosure includes determining the presence, location and/or the size of the tumor metastasis prior to and/or after having provided one or more dose of the humanized antibodies or of the chimeric proteins. Such assessment can be useful to determine if additional doses of the humanized antibody should be administered to achieve the desired therapeutic result in the subject.

The humanized antibody or the chimeric protein comprising same can be formulated as a pharmaceutical composition for administration with an excipient. An excipient or "pharmaceutical excipient" is a pharmaceutically acceptable solvent, suspending agent or any other pharmacologically inert vehicle for delivering one or more chimeric protein to a subject, and is typically liquid. A pharmaceutical excipient is generally selected to provide for the desired bulk, consistency, etc., when combined with components of a given pharmaceutical composition, in view of the intended administration mode. Typical pharmaceutical excipients include, but are not limited to binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycotate, etc.); and wetting agents (e.g., sodium lauryl sulphate, etc.).

The humanized antibody or the chimeric protein comprising same may be formulated for administration with a pharmaceutically-acceptable excipient, in unit dosage form or as a pharmaceutical composition. Conventional pharmaceutical practice may be employed to provide suitable formulations or compositions to administer such compositions to subjects. Although intravenous administration is preferred, any appropriate route of administration may be employed, for example, oral, perenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. Therapeutic formulations may be in the form of liquid solutions or suspension. Methods well known in the art for making formulations are found in, for example, Remington: The Science and Practice of Pharmacy, (19th ed.) ed. A. R. Gennaro A R 1995, Mack Publishing Company, Easton, PA.

In addition, in some embodiments, the humanized antibody or the chimeric protein can be administered at a pharmaceutically effective amount. The term "pharmaceutically effective amount" or "therapeutically effective amount" refers to an amount (dose) effective in treating a subject afflicted by or suspected to be afflicted by an thrombotic, metastatic or inflammatory condition or disorder. It is also to be understood herein that a "pharmaceutically effective amount" may be interpreted as an amount giving a desired therapeutic effect, either taken in one dose or in any dosage or route, taken alone or in combination with other therapeutic agents.

A therapeutically effective amount or dosage of the humanized antibody or the chimeric protein comprising same disclosed herein or a pharmaceutical composition, may range from about 0.001 to 30 mg/kg body weight, with other ranges of the invention including about 0.01 to 25 mg/kg body weight, about 0.025 to 10 mg/kg body weight, about 0.3 to 20 mg/kg body weight, about 0.1 to 20 mg/kg body weight, about 1 to 10 mg/kg body weight, 2 to 9 mg/kg body weight, 3 to 8 mg/kg body weight, 4 to 7 mg/kg body weight, 5 to 6 mg/kg body weight, and 20 to 50 mg/kg body weight. In other embodiments, a therapeutically effective amount or dosage may range from about 0.001 to 50 mg total, with other ranges of the invention including about 0.01 to 10 mg, about 0.3 to 3 mg, about 3 to 10 mg, about 6 mg, about 9 mg, about 10 to 20 mg, about 20-30 mg, about 30 to 40 mg, and about 40 to 50 mg. In an embodiment, the chimera is administered to a dosage between about 40-80 mg/kg (e.g. 60 mg/kg).

Example I—Humanization of Murine NIT-B1 Antibodies

The variable domains of murine NIT-A1 and NIT-B1 antibodies (described in U.S. Pat. No. 8,323,652 and respectively deposited at the International Depositary Authority of Canada on Oct. 7, 2008 under Accession Numbers 071008-01 (NIT A1 clone), 071008-02 (NIT B1 clone)) were sequenced. The murine NIT-A1 antibody has a heavy chain of SEQ ID NO: 1 (including CDR1 of SEQ ID NO: 3, CDR2 of SEQ ID NO: 4 and CDR3 of SEQ ID NO: 5) and a light chain of SEQ ID NO: 11 (including CDR1 of SEQ ID NO: 13, CDR2 of SEQ ID NO: 14 and CDR3 of SEQ ID NO: 15). The murine NIT-B1 antibody has a heavy chain of SEQ ID NO: 6 (including CDR1 of SEQ ID NO: 8, CDR2 of SEQ ID NO: 9 and CDR3 of SEQ ID NO: 10) and a light chain of SEQ ID NO: 16 (including CDR1 of SEQ ID NO: 18, CDR2 of SEQ ID NO: 19 and CDR3 of SEQ ID NO: 20).

The murine NIT-B1 antibody was further developed as a chimeric C100-Fab by fusing the NIT-B1 heavy chain variable domain (SEQ ID NO: 6) with a human IgG1 constant region CH1 (SEQ ID NO: 26; https://www.uniprot.org/uniprot/P01857); as well as fusing the NIT-B1 light chain variable domain (SEQ ID NO: 16) with a human Ig kappa light chain constant region (SEQ ID NO: 33; http://www.uniprot.org/uniprot/P01834).

Example II—Characterization of Humanized Anti-GPIbalpha Antibodies

Using CDR grafting method (Safdari et al., 2013), four human heavy (VH1 of SEQ ID NO: 35, VH2 of SEQ ID NO: 42, VH3 of SEQ ID NO: 49, VH4 of SEQ ID NO: 56) and four human light (VL1 of SEQ ID NO: 63, VL2 of SEQ ID NO: 70, VL3 of SEQ ID NO: 77, VL4 of SEQ ID NO: 84) chains were synthesized based on homology of the frame works to human sequences in the NCBI database with the annotated CDRs.

Briefly, the variable domain sequences of parental antibody were searched in the database of human germline using NCBI Ig-Blast (http://www.ncbi.nlm.nih.gov/projects/igblast/). Four diverse human acceptors (i.e. human variable domains with high homology to the parental antibody) for each heavy chain and light chain were chosen. The CDRs of human acceptors were replaced with their mouse counterparts, resulting in the humanized variable domain sequences.

Humanized single-chain variable fragment (scFv) and associated chimeric protein. A scFv including both VH1 and VL2 was prepared. It included a (GGGGS (SEQ ID NO: 92))×4 linker between VH1 and VL2 (orientation as VH1-(G4S)4-VL2). For facilitating the purification, the scFv had a 6×His-tag and a TEV cleavage site ENLYFQG prior to VH1. The tag was however removed using the TEV protease prior to the different testing. The scFv was also included in a chimeric protein (scFv-HSA) with the human serum albumin (HSA). In those instances, the scFv-HSA included an additional linker GGGGS (SEQ ID NO: 92) ahead of HSA. The chimeric scFv-HSA was produced in a stable form and did not form aggregates during its production or purification.

Figure 2:
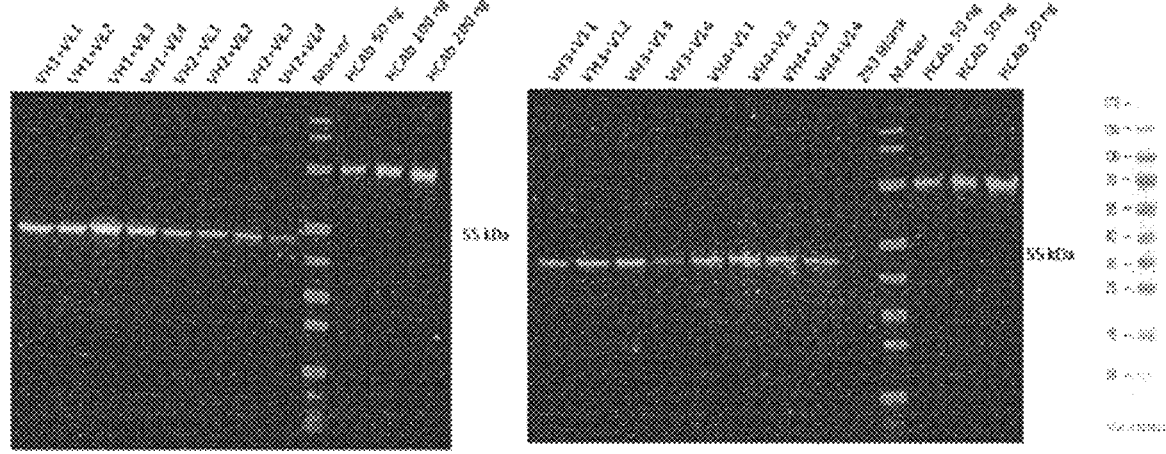
FIG. 2 shows the results of a Western blot results of humanized Fabs under non-reducing conditions. About 20 μL of supernatant was loaded in each lane. The molecular weight ladder (in KDa) is shown on the left. Heavy-chain only (HCAb) antibodies were used as a control.

Size. The DNA sequences encoding humanized heavy and light chains were synthesized and inserted into pTT5 vector to construct expression plasmids of Fabs. Sixteen humanized Fabs were transiently expressed in HEK 293 or CHO 3E7 cell culture, and then the cells were spun down. The supernatants were filtered and evaluated with SDS-PAGE and Western-blot analysis. The humanized Fabs have molecular weight of approximately 47 kDa under non-reducing conditions (FIGS. 1 and 2).

Figure 3:
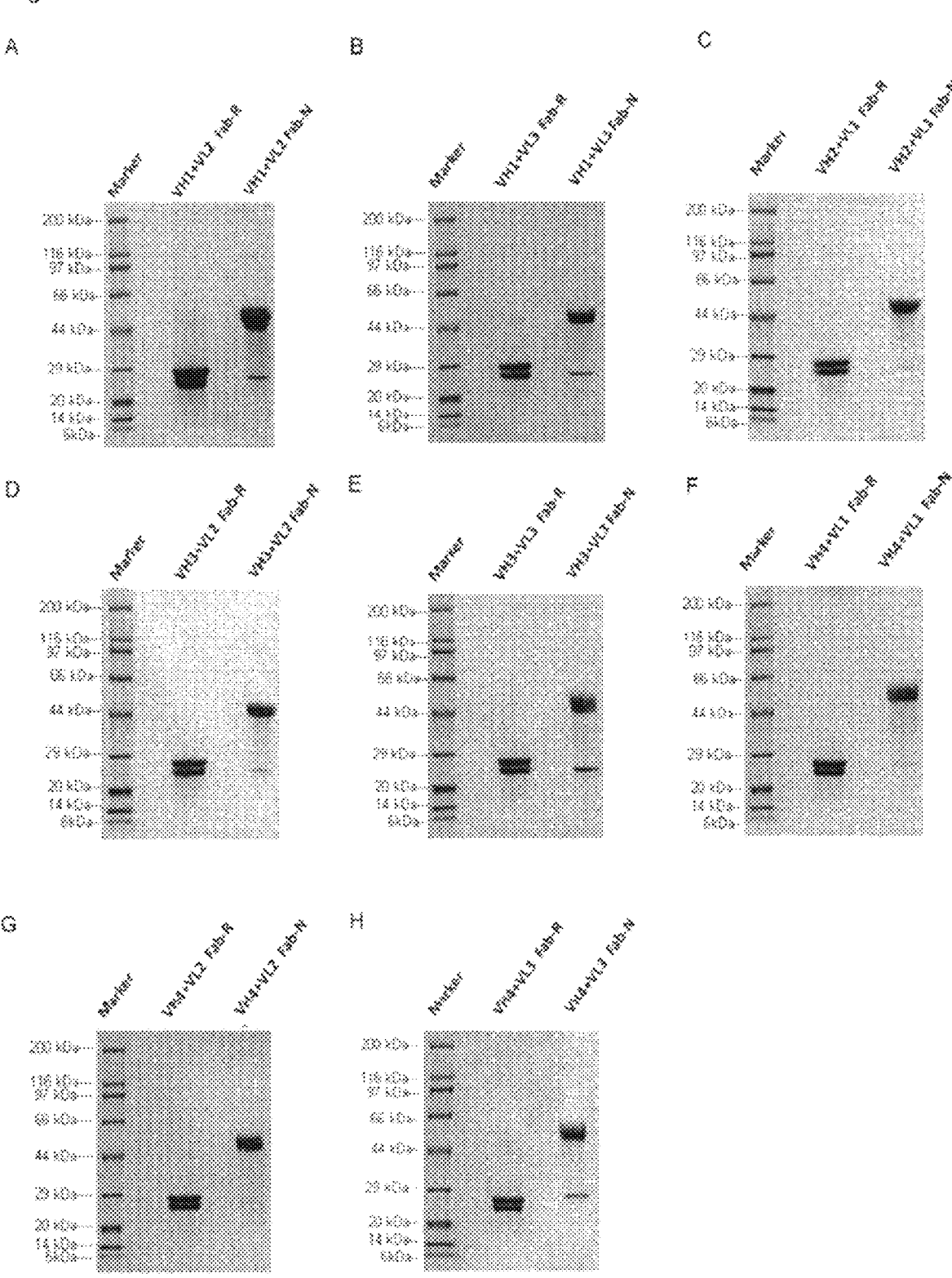
FIGS. 3A to H show the results of a SDS-PAGE under non-reducing (labelled as "N") and reducing conditions (labelled as "R") for purified Fabs comprising (FIG. 3A) the VH1 and VL2 chains, (FIG. 3B) the VH1 and VL3 chains, (FIG. 3C) the VH2 and VL1 chains, (FIG. 3D) the VH3 and VL2 chains, (FIG. 3E) the VH3 and VL3 chains, (FIG. 3F) the VH4 and VL1 chains, (FIG. 3G) the VH4 and VL2 chains and (FIG. 3H) the VH4 and VL3 chains.

The supernatants of eight selected humanized Fabs (see table 1) were then purified by Capture Select™ Kappa XL Affinity Matrix resin. The purified humanized Fabs were buffer-exchanged into PBS using a PD-10 desalting column. The concentration and purity of the purified protein were determined by $OD_{280}$ and SDS-PAGE (about 2 µg of protein was loaded in each lane), respectively. As shown on FIG. 3, the purified humanized Fabs migrated as ~47 kDa band in SDS-PAGE under non-reducing condition, ~24 kDa and ~23 kDa bands under reducing condition.

TABLE 1

| Description of the humanized Fabs | | |
|---|---|---|
| Name | Heavy chain | Light chain |
| H001 | VH1 (SEQ ID NO: 35) | VL2 (SEQ ID NO: 70) |
| H002 | VH1 (SEQ ID NO: 35) | VL3 (SEQ ID NO: 77) |
| H003 | VH2 (SEQ ID NO: 42) | VL1 (SEQ ID NO: 63) |
| H004 | VH3 (SEQ ID NO: 49) | VL2 (SEQ ID NO: 70) |
| H005 | VH3 (SEQ ID NO: 49) | VL3 (SEQ ID NO: 77) |
| H006 | VH4 (SEQ ID NO: 56) | VL1 (SEQ ID NO: 63) |
| H007 | VH4 (SEQ ID NO: 56) | VL2 (SEQ ID NO: 70) |
| H008 | VH4 (SEQ ID NO: 56) | VL3 (SEQ ID NO: 77) |

Figure 4:
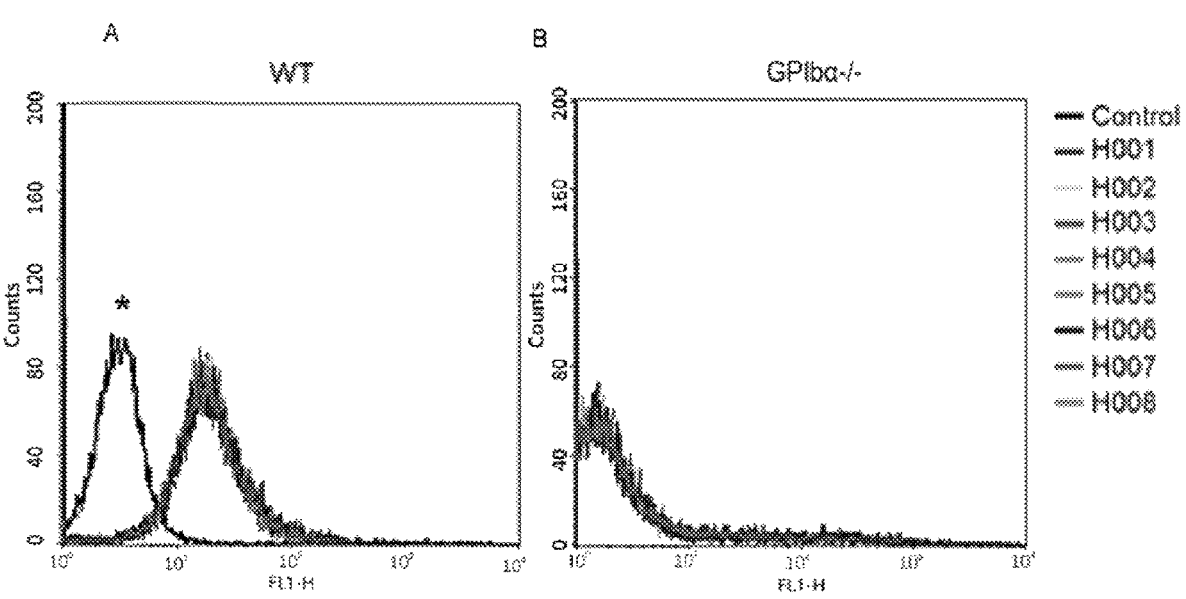
FIGS. 4A and B show that the humanized Fabs H001 to H008 bind to (FIG. 4A) wild-type mouse platelets but not to (FIG. 4B) GPIbα−/− mouse platelets (5 μg/mL). The "*" shown on FIG. 4B indicated the control signal.
Figure 19:
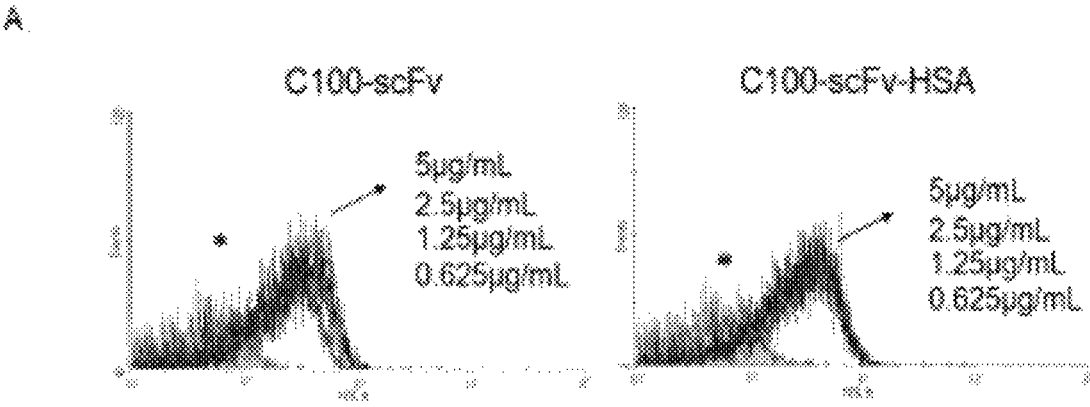
FIG. 19A to D show that the humanized C100-scFv and humanized C100-scFv fused with human albumin (C100-scFv-HSA) bind to (FIG. 19A) wild-type mouse platelets but not to (FIG. 19B) GPIbα–/– mouse platelets, as well as bind to (FIG. 19C) human platelets at dose indicated. The "★" shown on FIGS. 19A and C indicated the control signal.
Figure 19:
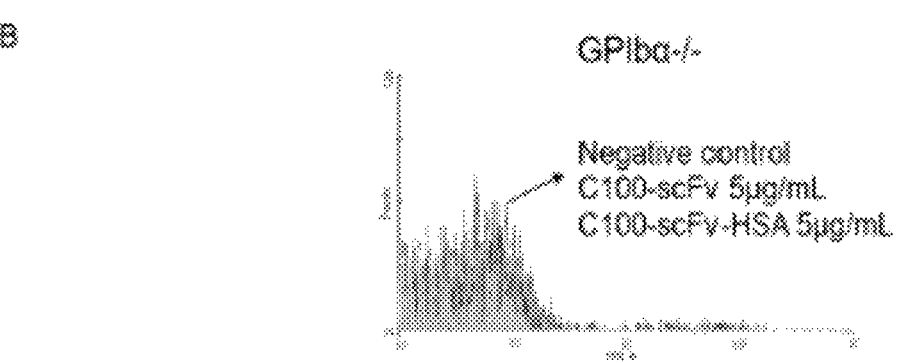
Figure 19:
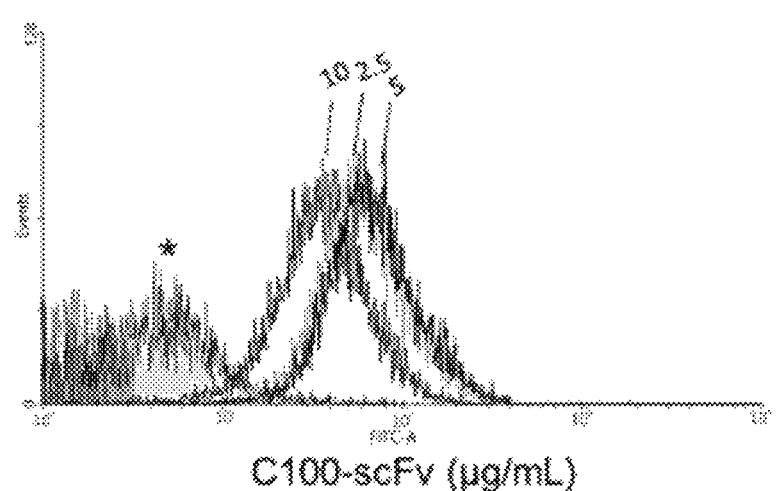
Figure 19:
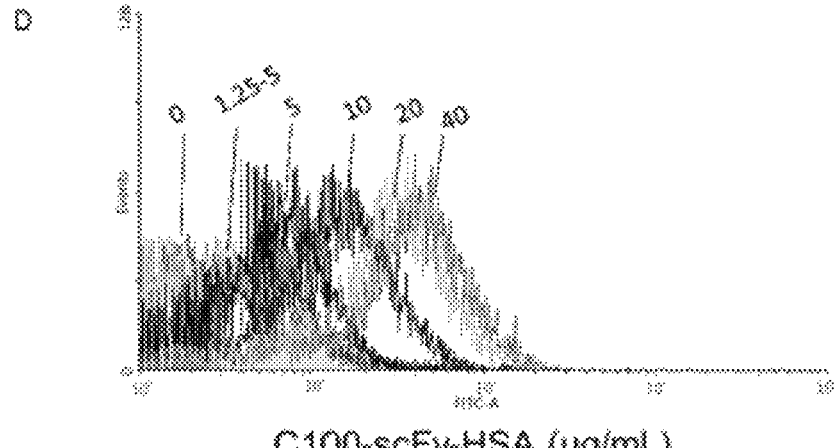
Figure 20:
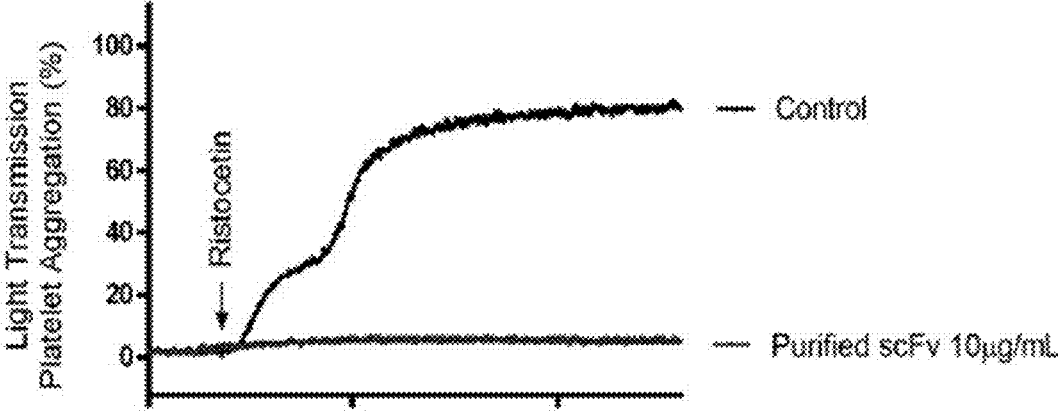
FIG. 20 shows standard aggregometry traces indicating that the humanized C100-scFv inhibited platelet aggregation induced by ristocetin.
Figure 21:
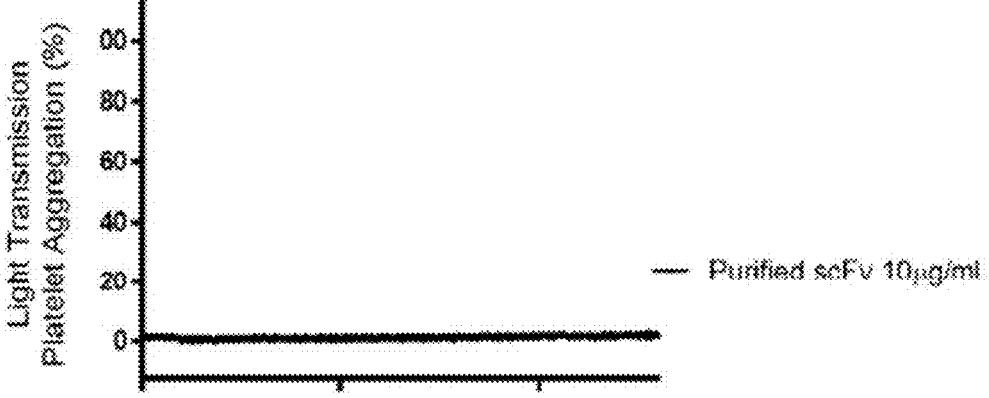
FIG. 21 shows standard aggregometry traces indicating that the humanized C100-scFv did not induce platelet activation in platelet-rich plasma.

Specificity. Human and mouse platelet-rich plasma (PRP) was prepared by centrifugation at 300 g for 7 min, and was washed by transferring 200 µL PRP into 10 mL PBS followed with 800 g centrifugation for 10 min. The supernatant was then removed and platelets were re-suspended in 200 µL PBS. Washed platelets (10 µL) were incubated with the different antibodies (2.5-5 µg/mL) in a 200 µL system at room temperature for 30 min, and detected by FITC labeled anti-human-Fab antibody. These eight selected humanized Fabs H001-H008, the scFv and the chimeric protein all bound to both human and wild-type mouse platelets, but not GPIbα deficient mouse platelets, indicating the specificity of the humanized Fabs to platelet GPIbα (FIGS. 4 and 19).

Figure 5:
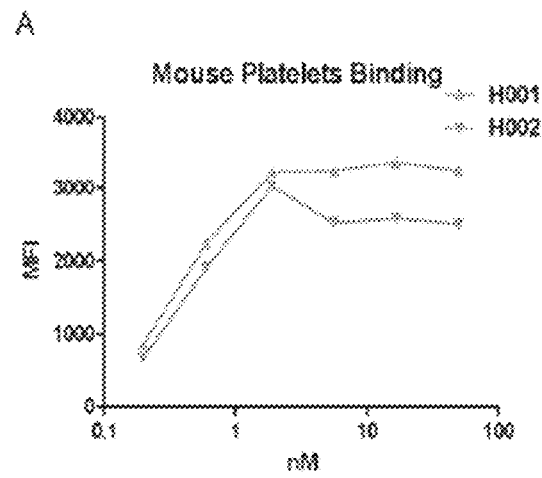
FIGS. 5A to E show that purified Fabs H001 (▲) and H002 (▼) bind to (FIG. 5A) mouse, (FIG. 5B) dog, (FIG. 5C) human, (FIG. 5D) rat and (FIG. 5E) rabbit platelets. Humanized Fabs binding to platelets was tested in vitro by flow cytometry assay.
Figure 5:
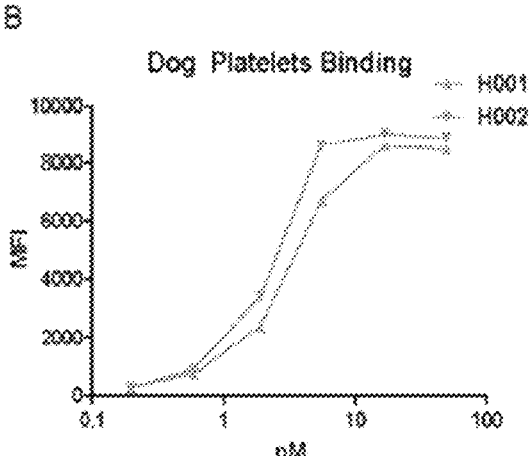
Figure 5:
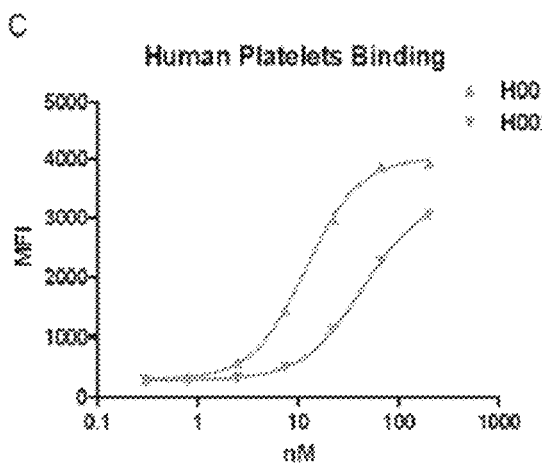
Figure 5:
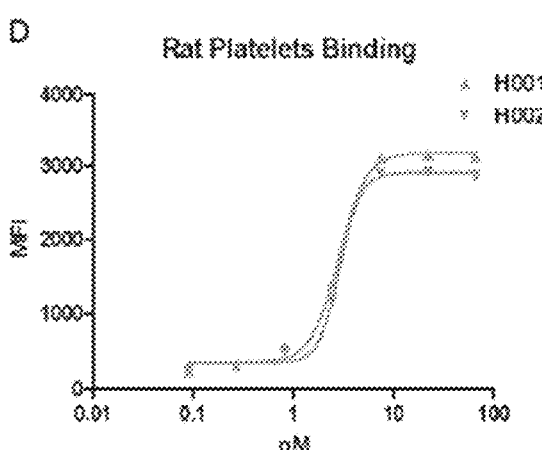
Figure 5:
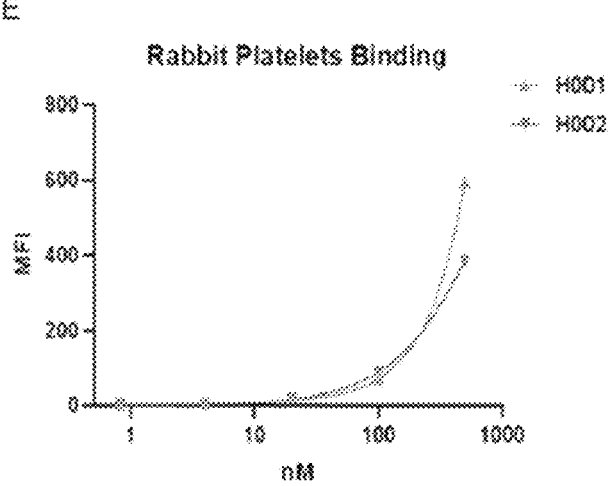

Platelets ($2\times10^5$) from mouse, dog, human, rat and rabbit PRP were transferred into 200 µL PBS containing a serial concentration of the Fabs H001 or H002 at 50, 16.7, 5.6, 1.8, 0.6, 0.2 nM (for mouse and dog), at 200, 67, 22, 7.4, 2.5, 0.8, 0.3, 0.1 nM (for human and rat) and at 500, 100, 20, 4, 0.8 nM (for rabbit). After a 30 min incubation, a detection antibody (FITC-labeled anti-human Kappa chain, 1:200) was added and incubated in darkness for 15 min. Flow cytometry was performed using the BD LSR Fortessa™ X-20. H001 and H002 also bound to rat, dog and rabbit platelets (FIG. 5).

Figure 6:
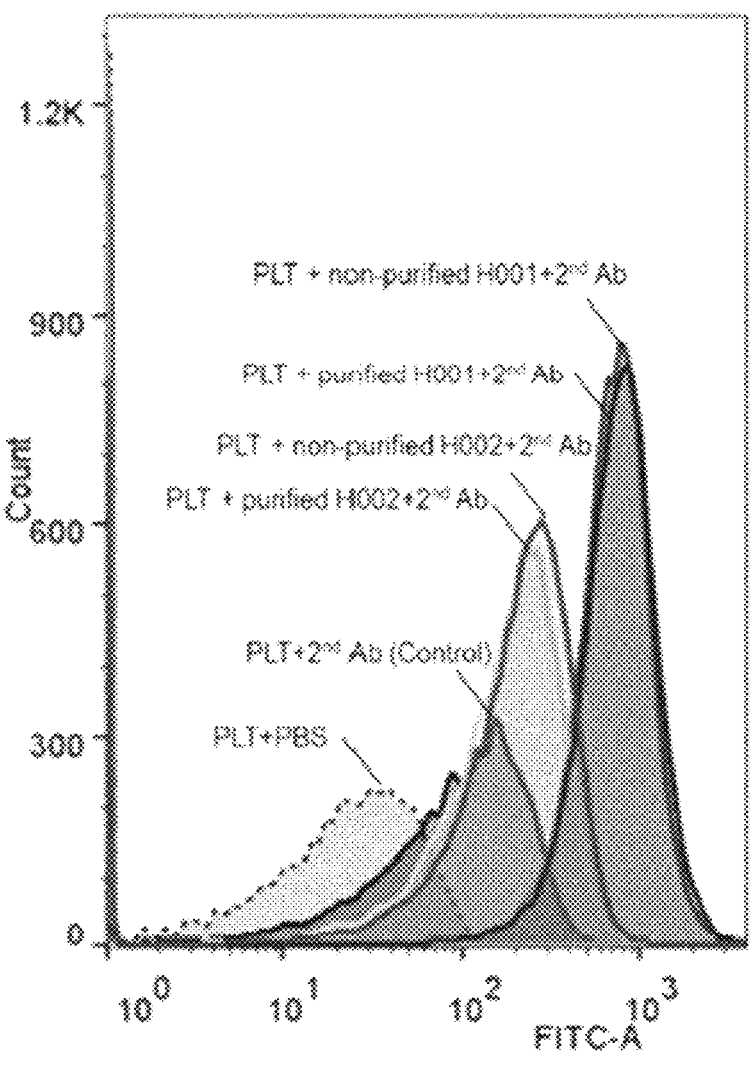
FIG. 6 shows flow cytometry results that purified Fabs H001 and H002 bind to monkey platelets.

Humanized Fabs with (purified H001/H002, 5 µg/mL) and without (non-purified H001/H002, 5 µg/mL) the second purification by SEC-FPLC chromatography were incubated with Cynomolgus monkey washed platelets ($2\times10^6$) for 30 min. A FITC-labeled anti-human Kappa chain secondary antibody (Ab) was then incubated for 30 minutes. Humanized Fabs binding to monkey platelets were detected by flow cytometry assay. FIG. 6 shows that Fab H001 and H002 antibodies bound to monkey platelets.

The affinity between H001 and recombinant GPIbα was measured in a surface plasmon resonance (SPR) assay. For preparation of SPR biosensors, SPR bare gold coated biosensors (Biosensing Instrument Inc., AZ, USA) were cleaned in a solution of 0.5 M sodium borohydride dissolved in 1:1 anhydrous ethanol:ddH₂O for 2 hours. The biosensors were rinsed with copious amounts of anhydrous ethanol followed by 16 hour incubation in a solution of 1 mM mercaptopropionic acid in dimethylformamide. Following the incubation, SPR biosensors were rinsed with copious amounts of dimethylformamide followed by anhydrous ethanol and finally ddH₂O. The biosensors were then incubated in 40 mM 1-Ethyl-3-(3-dimethylaminopropyl) carbodiimide and 20 mM N-Hydroxysuccinimide dissolved in ddH₂O for 1 hour. Sensors were then rinsed with copious amounts of ddH₂O and then incubated with 100 mM Nα,Nα-Bis(carboxymethyl)-L-lysine hydrate for 4 hour. Following the incubation, the biosensing surfaces were rinsed with ddH2O. The final step before SPR experiments was to expose the functionalized biosensing surfaces with 100 mM NiCl₂ for 1 hour.

The SPR experiments were performed on a Biosensing Instrument 4000 SPR. The functionalized biosensors were loaded onto the instrument and the biosensor was equilibrated with running buffer (10 mM tris(hydroxymethyl) aminomethane, 140 mM NaCl, 20 mM Imidazole pH=7.4) at a flow rate of 40 μL/min. For binding measurements 25 μL of 500 nM hexa-histidine tagged GPIbα was injected over the biosensing surface immobilizing the GPIbα to the SPR sensor surface. The baseline was allowed to equilibrate followed by injection of 25 μL of the desired concentration of ligand (either Fab H001 or control). Biosensing surfaces were regenerated between ligand injections by injection of 100 μL of 500 mM imidazole in running buffer, followed by 100 μL of 100 mM $NiCl_2$. The resulting data was analyzed using the instrument included SPR analysis software.

Figure 7:
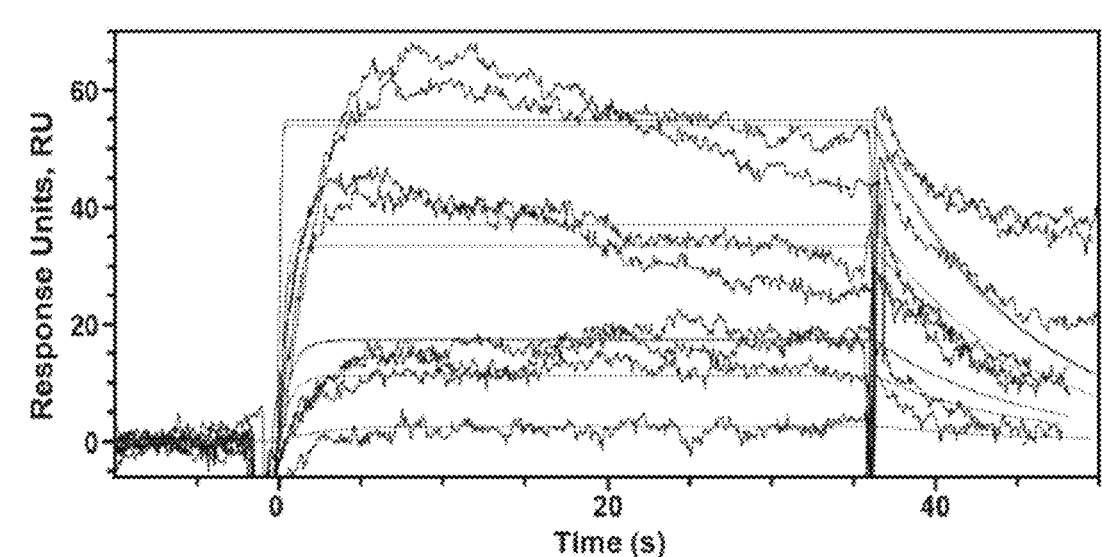
FIG. 7 shows that purified Fab H001 antibody binds to recombinant GPIbα in a surface plasmon resonance (SPR) assay.
Figure 7:
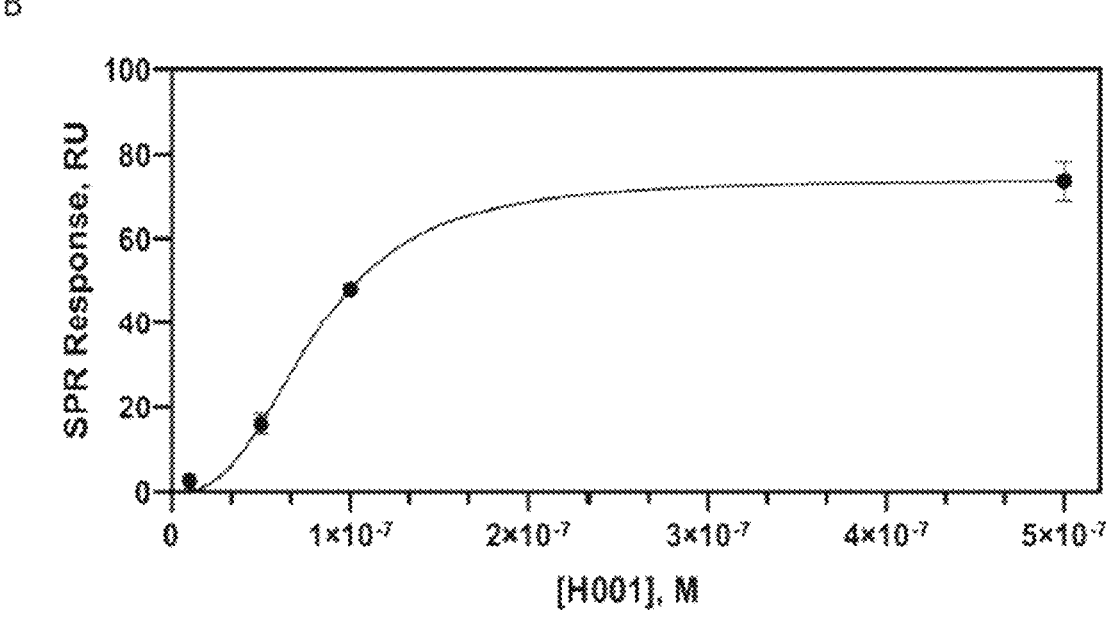
Figure 8:
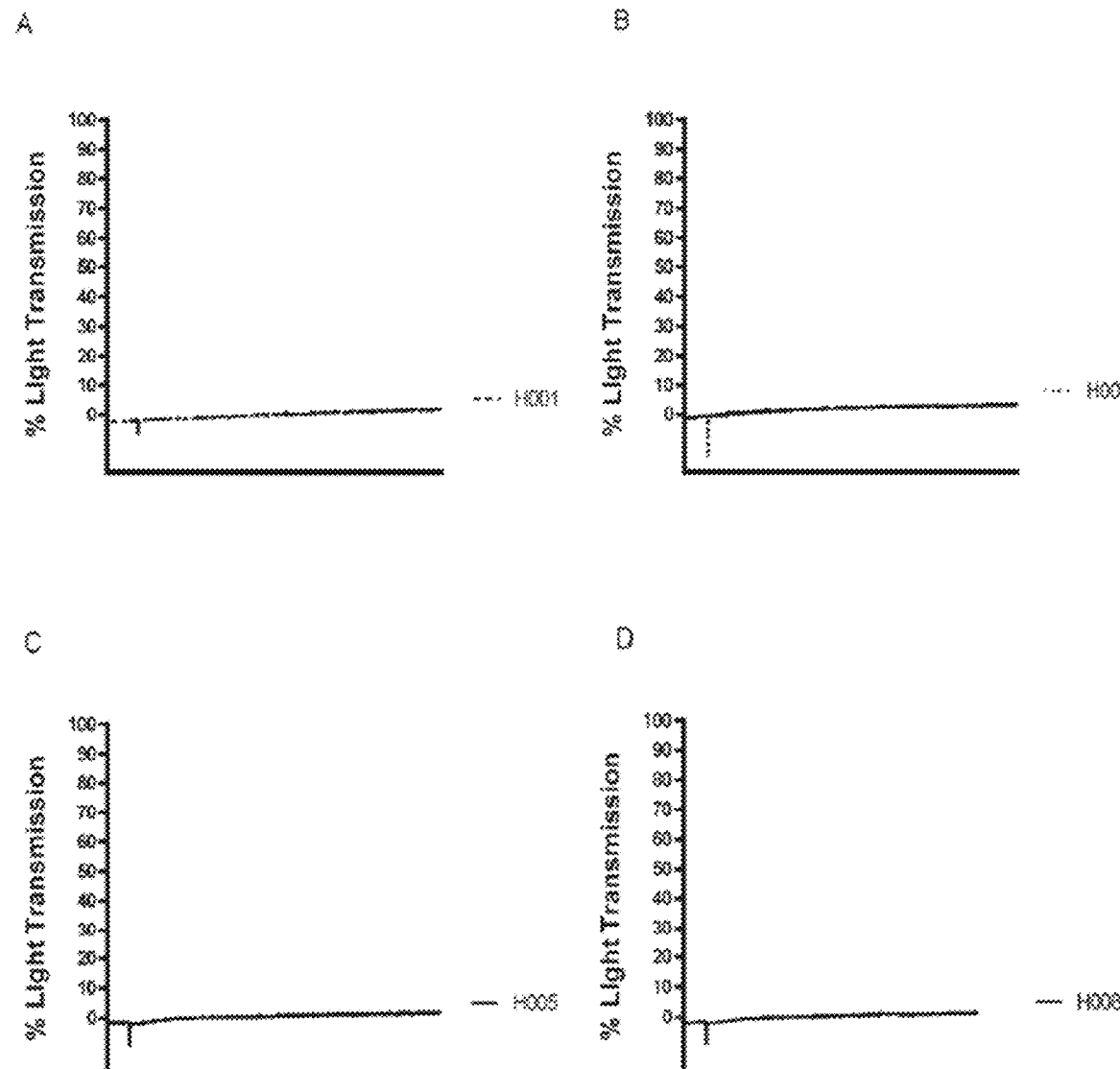
FIGS. 8A to D show standard aggregometry traces indicating that the purified Fabs (FIG. 8A) H001, (FIG. 8B) H002, (FIG. 8C) H005 and (FIG. 8D) H008 did not induce platelet activation in platelet-rich plasma.
Figure 9:
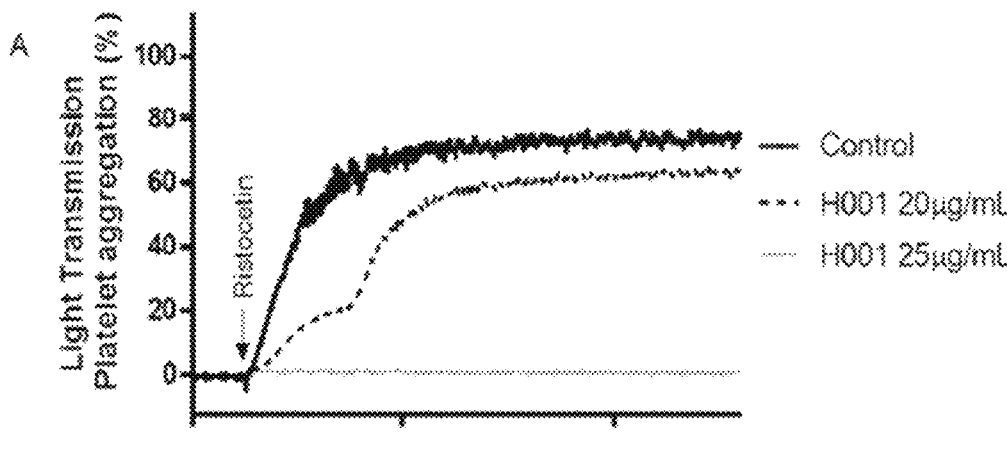
FIGS. 9A to D show standard aggregometry traces indicating that purified Fabs (FIGS. 9A and 9D) H001 and (FIGS. 9B, 9C and 9D) H002 inhibited platelet aggregation induced by ristocetin (A, B and D) or low dose thrombin (C). Platelets were obtained from healthy volunteers (A to C) or patients with peripheral vascular disease (D).
Figure 9:
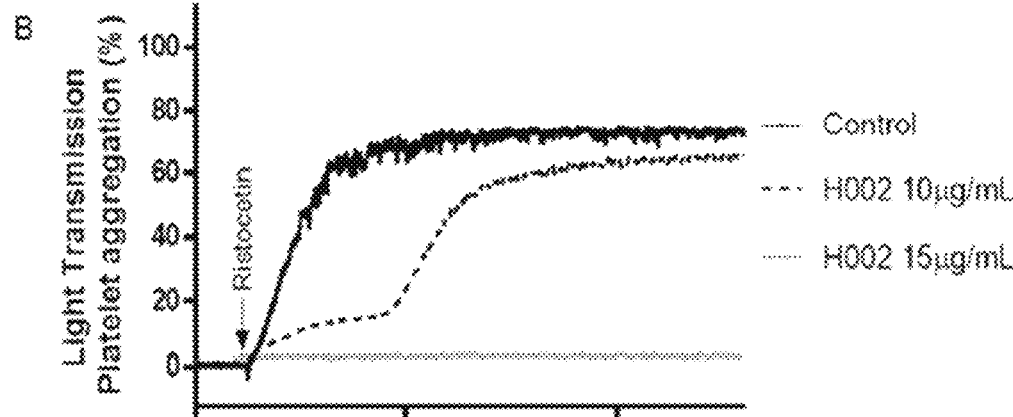
Figure 9:
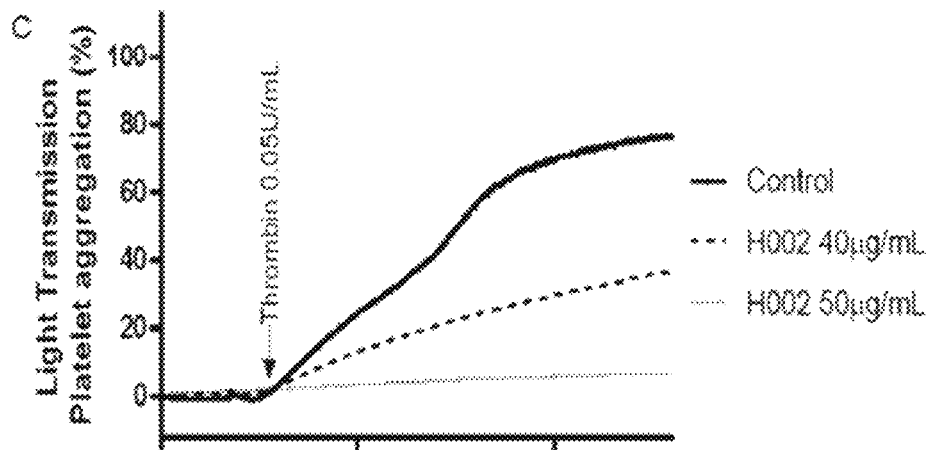
Figure 9:
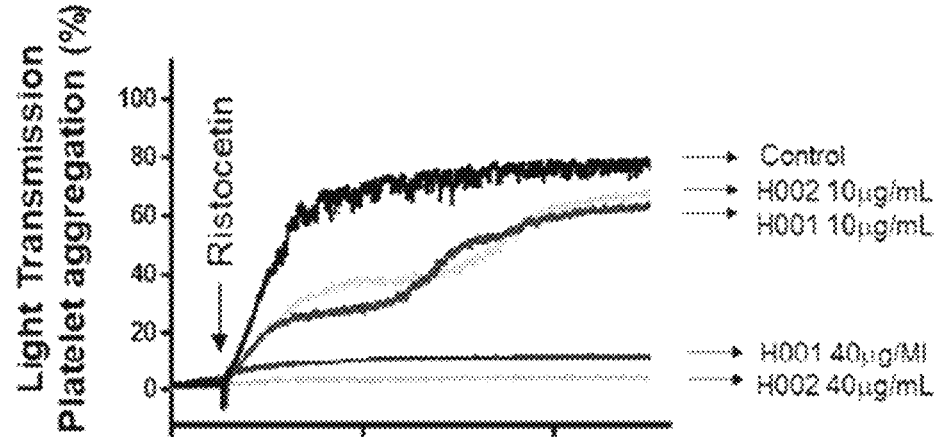

GPIbα immobilized SPR biosensors were exposed to 500, 100, 50 and 10 nM of Fab H001 antibody and 100 nM control antibody (PSI E1, an antibody against GPIIbIIIa). The control did not bind the immobilized GPIbα and fully dissociated from the biosensor prior to the end of injection (data not shown). In contrast the Fab H001 antibody clearly bound GPIbα producing clear SPR shifts with only partial dissociation after the end of the injection (FIG. 7A). The SPR shifts were fit to the kinetics binding model resulting in an on rate $(k_a)$ of $2.61 \times 10^7$ s$^{-1}$ an off rate $(k_d)$=$1.1 \times 10^{-1}$ s$^{-1}$ and a dissociation constant (Kd) of 4.4 nM (FIG. 7B). To confirm the dissociation constant, the magnitude of the SPR shifts were plotted against the Fab H001 antibody concentration and fit to a one site binding model producing a fit $R^2$ of 0.9929 and a dissociation constant (Kd) of 8.0±2.1 nM. The data clearly demonstrates that the Fab H001 antibody bound recombinant GPIbα tightly with a low nanomolar dissociation constant and a fast binding on rate.

In vitro inhibition of agonists-induced platelet aggregation. To evaluate whether the humanized Fabs can induce aberrant platelet activation, and their roles in platelet aggregation, in vitro platelet aggregation assays were performed. Human PRP from healthy volunteers and patients with peripheral vascular disease was prepared from sodium-citrate anti-coagulated whole blood by centrifugation at 300 g for 7 min. Platelet aggregation in PRP was induced by the addition of 5 μg/mL humanized Fab clones and monitored by a computerized Chrono-log aggregometer (Chrono-Log Corporation, USA). Platelet aggregation in PRP was induced by ristocetin (1 mg/mL), and in gel-filtered platelets was induced by thrombin (0.05 U/mL) with or without the humanized Fabs using a computerized Chrono-log aggregometer (Chrono-Log Corporation, USA).

The Fab H001, H002, H005 and H008 antibodies as well as the scFv antibody did not induce platelet activation. Moreover, H001 and H002 significantly inhibited ristocetin-induced human platelet aggregation in PRP, and low-dose thrombin-induced platelet aggregation in gel-filtered platelets (FIGS. 8, 9, 20 and 21).

Inhibition of thrombus formation at low and high shear rate. To measure platelet adhesion, aggregation, and thrombus formation at different shear rates, heparinized-whole blood from 30 healthy volunteers was perfused over a type I collagen-coated surface using an ex vivo perfusion chamber system, under a real-time fluorescence microscope. Briefly, rectangular microcapillary tubes (ibidi channel slides, ibidi GmbH) were coated with Horm collagen (100 μg/mL, overnight, 4° C.; Nycomed Linz, Austria). Anti-coagulated (heparin 15 U/mL) whole blood from healthy donors was fluorescently-labeled with $DiOC_6$ (1 μM, 10 min, 37° C.; Sigma). Then, control or humanized Fabs or scFv-HSA treated whole blood was perfused over the collagen-coated surface at shear rates of 300 s$^{-1}$, 1,200 s$^{-1}$ and 1,800 s$^{-1}$ for 3 min using a syringe pump (Harvard Apparatus, USA). Platelet accumulation and thrombus formation were recorded in real-time under a Zeiss Axiovert 135-inverted florescent microscope (60×/0.90 NA water objective). Quantitative dynamics of platelet fluorescence intensity were acquired using SlideBook software.

Figure 10:
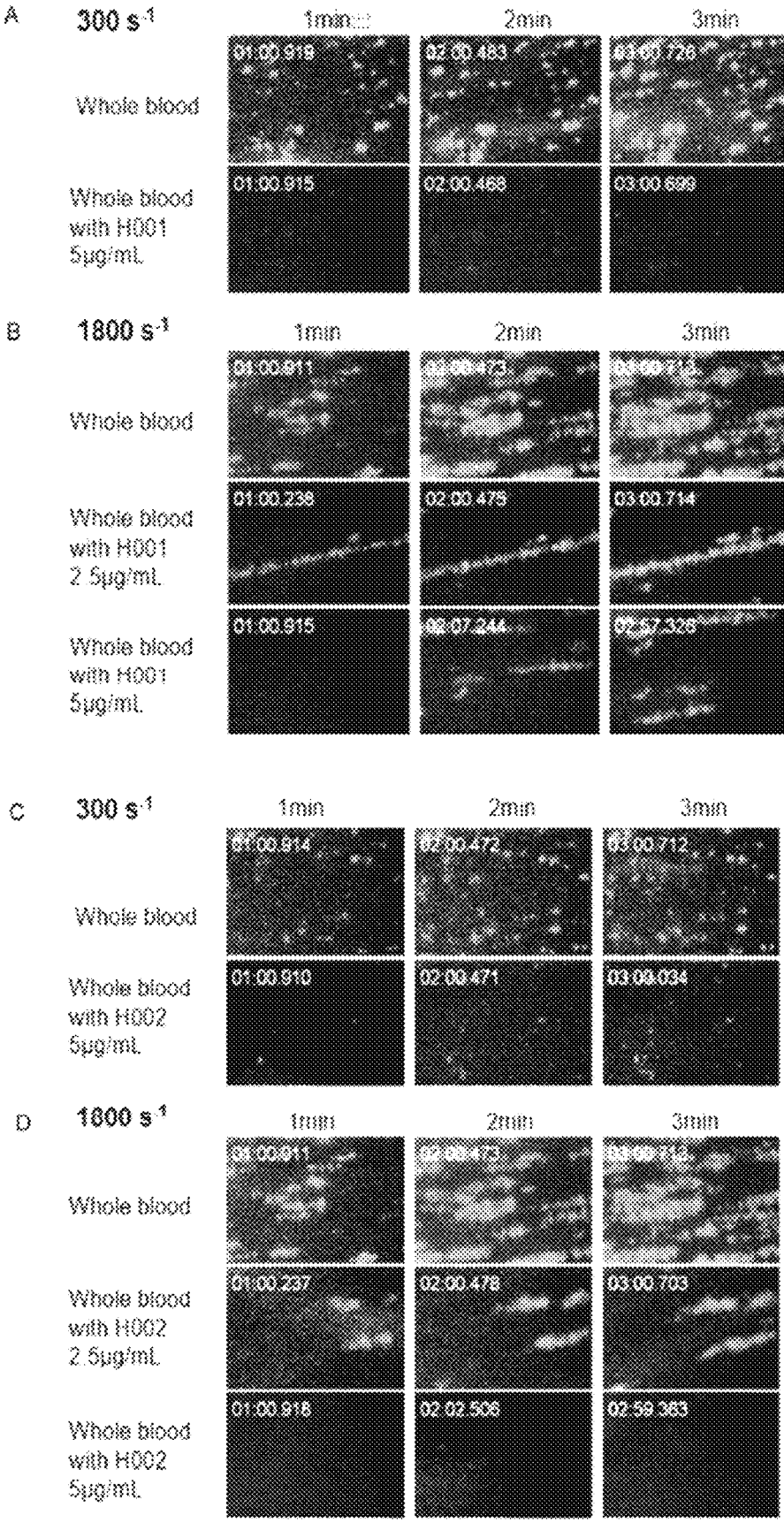
FIG. 10A to D show that the humanized Fabs H001 (FIGS. 10A and 10B) and H002 (FIGS. 10C and 10D) antibodies inhibited thrombus formation from human whole blood at both low (300 s⁻, FIGS. 10A and 10C) and high shear (1800 s⁻, FIGS. 10B and 10D) rate conditions.
Figure 22:
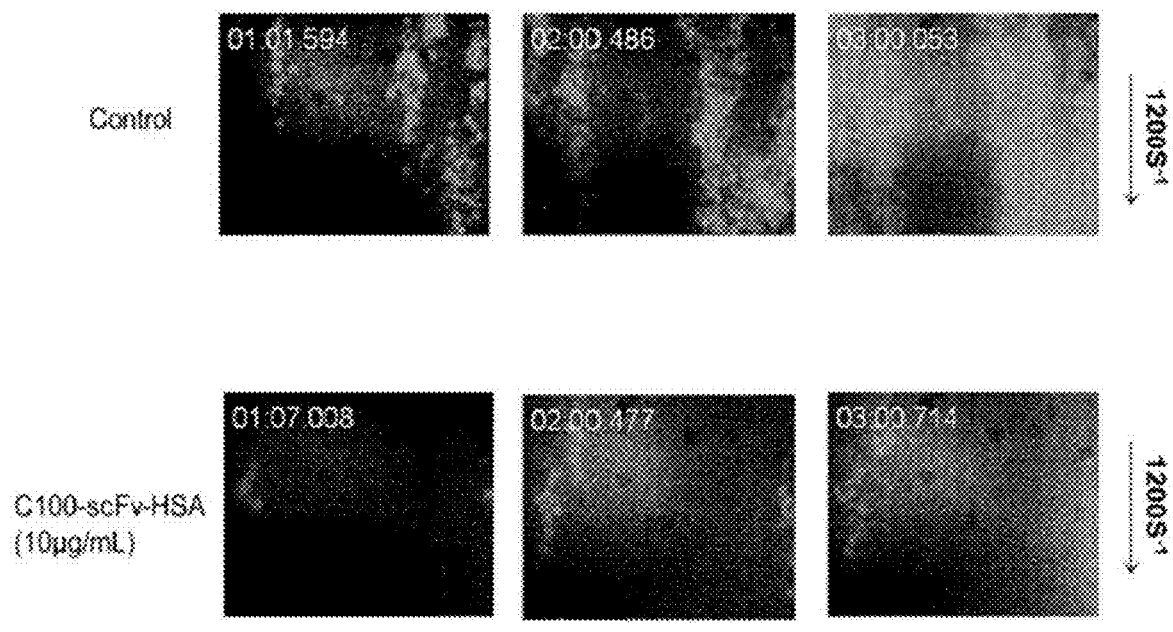
FIG. 22 shows that the humanized C100-scFv-HSA inhibited thrombus formation from human whole blood at high shear (1200 s⁻) rate conditions. Representative photographs showing the platelet thrombus formation after heparinized-human whole blood were perfused for 1, 2, and 3 minutes, which were treated with a control PBS buffer (top panels) and the humanized C100-scFv-HSA (10 μg/mL, bottom panels) at high shear (1200 s⁻) condition.

The humanized Fabs H001 and H002 markedly inhibited thrombus formation at both 300 s$^{-1}$ and 1,800 s$^{-1}$ wall shear rates (although preferably at 1,800 s$^{-1}$ wall shear rates), corresponding to blood flow in venules/large arteries and arterioles, respectively (FIG. 10). The chimeric protein markedly inhibit thrombus formation at 1,200 s$^{-1}$ wall shear rates (FIG. 22). These ex vivo results suggest that humanized C100-Fab, scFv and chimeric proteins are significant inhibitors of thrombosis under both low shear and high shear conditions.

In vivo inhibition of thrombus growth and vessel occlusion. To examine whether the humanized Fabs affects thrombus growth in vivo, two complementary intravital microscopy thrombosis models and a large artery thrombosis model were utilized.

Figure 11:
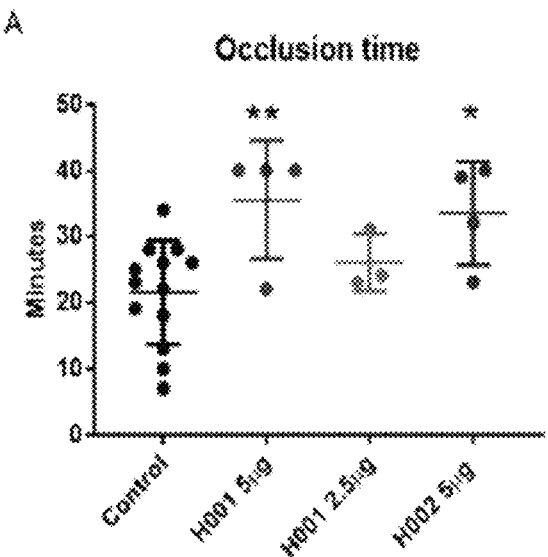
FIGS. 11A and B show that the humanized Fabs H001 and H002 antibodies prolonged vessel occlusion time in a FeCl₃-induced mesenteric arteriole thrombosis model in vivo.
(FIG. 11B) Representative photographs of arterioles treated with a control (top panels), the humanized Fab H001 antibody (5 μg/mouse, middle panels), the humanized Fab H002 antibody (5 μg/mouse, lowest panels) at different time points where indicated after vessel injury induced by FeCl₃. *P<0.05, **P<0.01.
Figure 11:
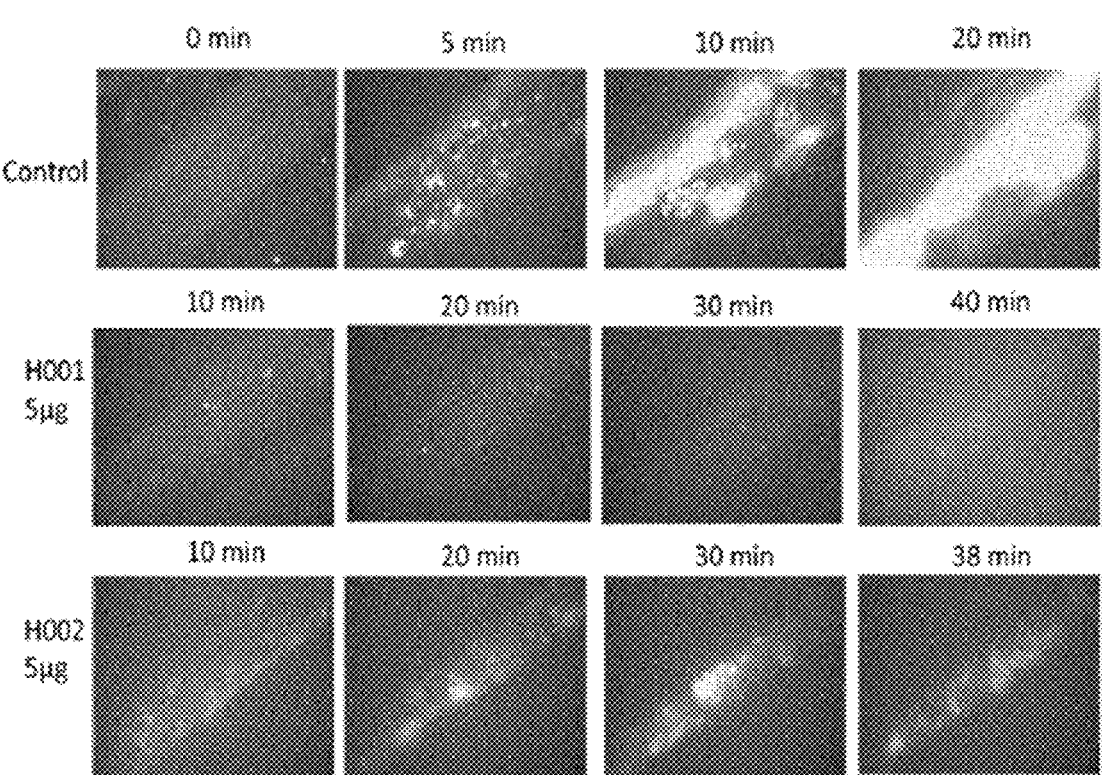

Thrombus formation in mesenteric arterioles was monitored in 3- to 4-week-old C57BL/6 wild-type mice. Mice were injected with donor-matched fluorescently labeled platelets and visualized under a Zeiss Axiovert 135-inverted fluorescent microscope (Zeiss, Germany). Briefly, blood was collected into an acid citrate dextrose solution (ACD; as anti-coagulant) from the donor-matched mice. Gel-filtered platelets were prepared and labeled with Calcein AM (1 mg/mL, Invitrogen, Canada) at room temperature for 20 min. Platelets were then injected into the experimental mice via the tail vein with control saline buffer, with Fab H001 or with H002 (2.5 or 5 μg/mouse). Mice were then anesthetized and the mesentery was externalized. A single mesenteric arteriole of 100-120 μm diameter was chosen and injury was induced by topical application of 30 μL of 250 mM ferric chloride. The time to complete vessel occlusion was recorded. Images of thrombus formation and dissolution were visualized with a fluorescence microscope. As shown in FIG. 11 and table 2, thrombus growth and vessel occlusion induced by $FeCl_3$ injury were significantly inhibited by injection of the humanized Fabs H001 and H002 antibodies (when compared to a control saline injection).

TABLE 2

| Number of mice that did not occlude in function of treatment received | |
| --- | --- |
| Control | 0 |
| H002-5 μg | 1 in 4 |
| H001-5 μg | 3 in 4 |
| H001-2.5 μg | 0 |

Figure 12:
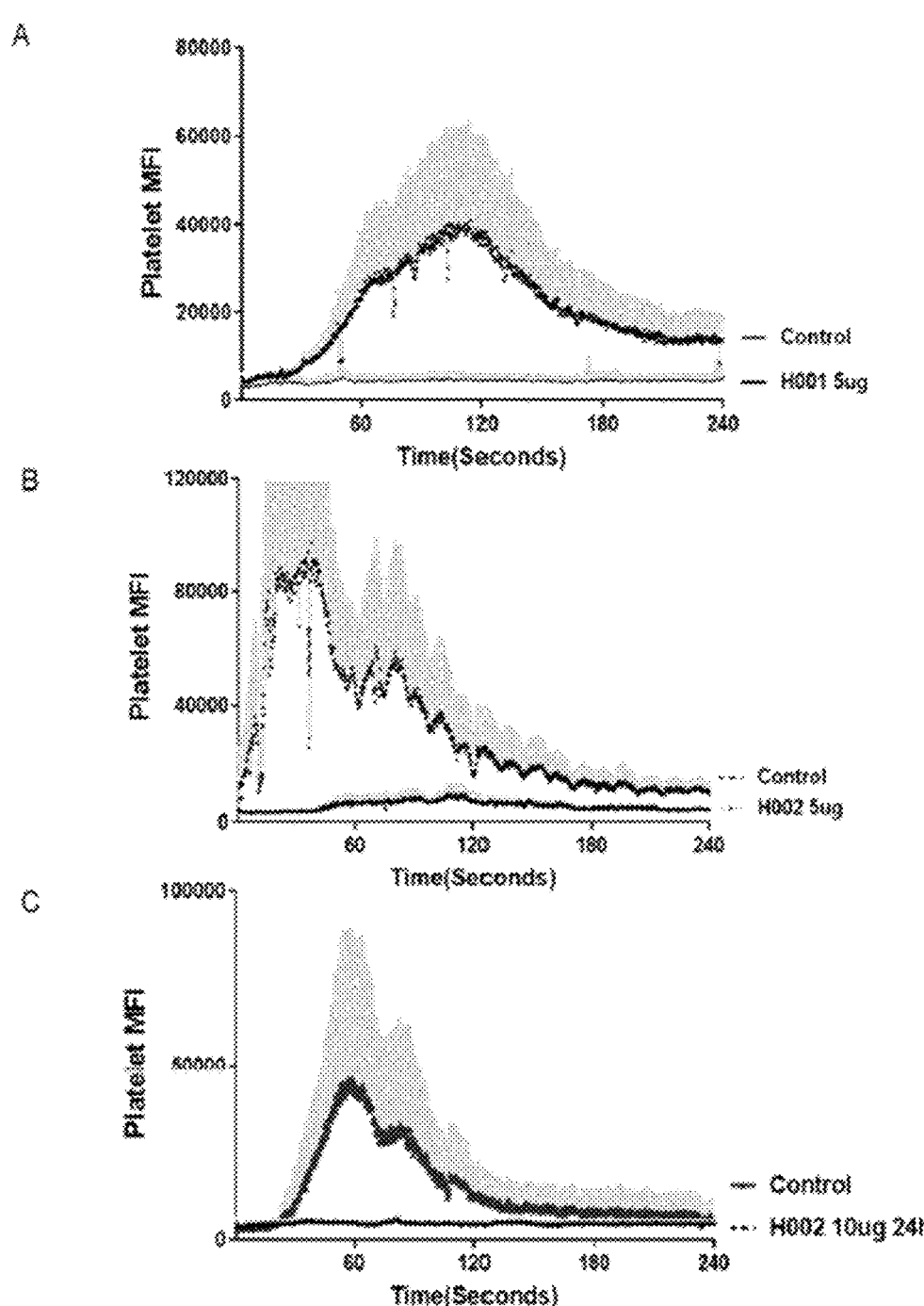
FIGS. 12A to C show that the humanized Fabs H001 and H002 antibodies inhibited thrombus formation in a laser-induced cremaster arteriole thrombosis model in vivo.

For the laser-induced cremaster arteriole thrombosis model, 057B/6 wild-type mice (male, 6-8 weeks old) were anesthetized and a tracheal tube was inserted to facilitate breathing. The cremaster muscle was prepared under a dissecting microscope and superfused throughout the experiment with preheated bicarbonate-buffered saline. Platelet antibody, control (saline buffer), the humanized and monovalent H001 and H002 antibodies (5 or 10 μg/mouse) were administered where indicated by a jugular vein cannula. Platelets were labeled by the rat anti-mouse CD41 antibody (Leo.A1; EMFRET Analytics, Germany; 0.1 μg/g) injection. Multiple independent upstream injuries were induced on a cremaster arteriole using an Olympus BX51WI microscope with a pulsed nitrogen dye laser. The dynamic accumulation of fluorescently labeled platelets within the growing thrombus was captured and analyzed using Slide-book software. In this cremaster arteriole intravital micros-copy thrombosis model (which does not involve oxidative stress as it induces mild vascular injury with a laser) the thrombus growth was almost completely abolished after intravenous infusion of the humanized and monovalent H001 and H002 antibodies (FIG. 12). These findings indi-cate that the humanized Fabs can inhibit thrombus growth and promote thrombus dissolution, and therefore have great potential to be developed as novel anti-thrombotic agents.

Figure 13:
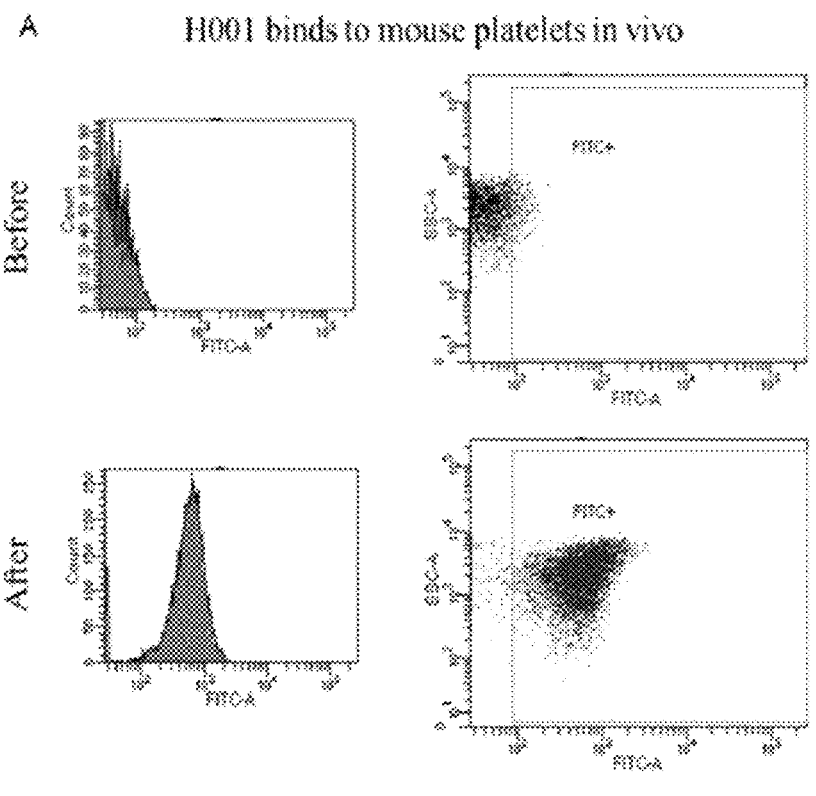
FIGS. 13A to C show that while the injected humanized Fab H001 is able to bind to platelets in vivo, it did not cause an increase in the expression of P-selectin or phosphatidylserine (PS). Results are shown as flow cytometry results for (FIG. 13A) platelets (FIG. 13B) P-selectin and (FIG. 13C) phosphatidylserine.
Figure 13:
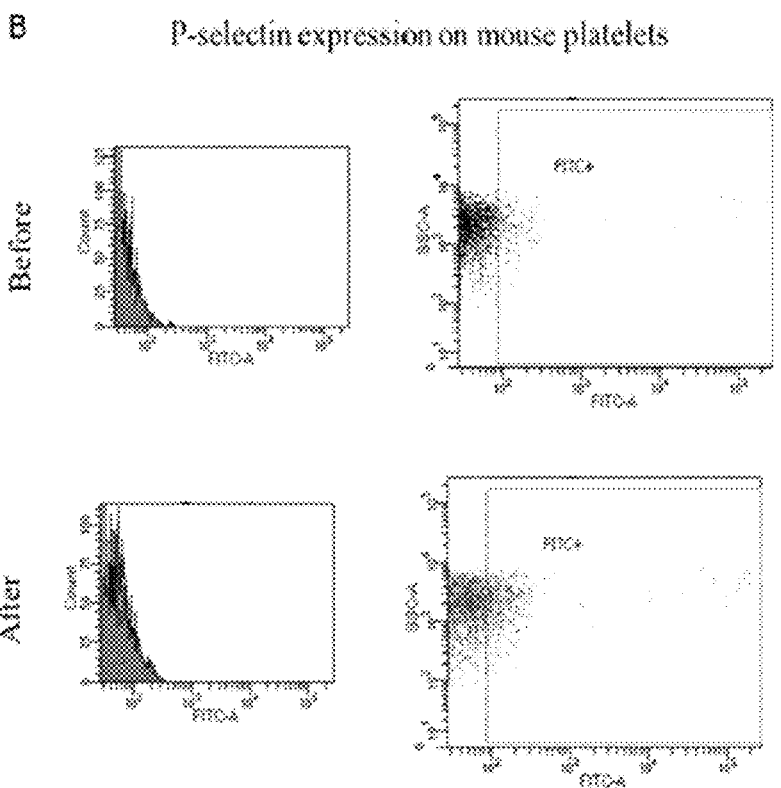
Figure 13:
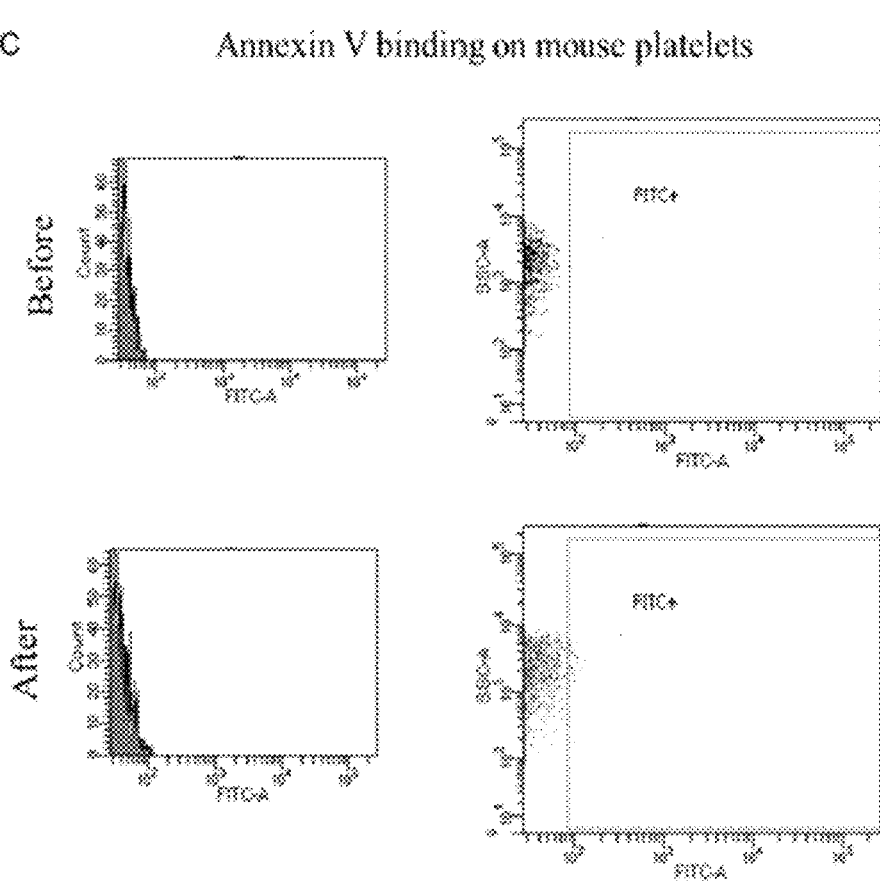

Mouse blood was drawn before and after the intravital microscopy thrombosis model experiments and the platelets were isolated and characterized using flow cytometry and FITC-labeled mouse anti-human CD62P antibody and Annexin V-Alexa Fluor® 647. It is shown in FIG. 13 that the humanized and monovalent H001 antibody did not induce platelet aberrant activation in vivo as it did not result in platelet P-selectin expression or phosphatidyl serine (PS) exposure. Similar results were obtained with the humanized Fab H002 antibody (data not shown).

Figure 14:
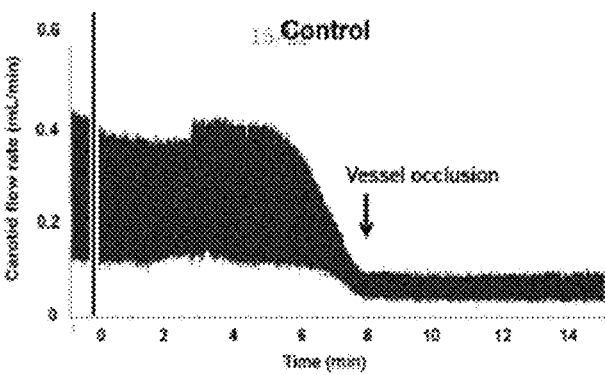
FIGS. 14A and B show that the humanized Fabs H001 and H002 antibodies prevented or prolonged vessel occlusion in a FeCl₃-induced carotid artery thrombosis model in vivo.
(FIG. 14B) Histogram showing the time to vessel occlusion (in minutes) in function of the antibody or the doses used. *P<0.05, #P<0.05, **P<0.01.
Figure 14:
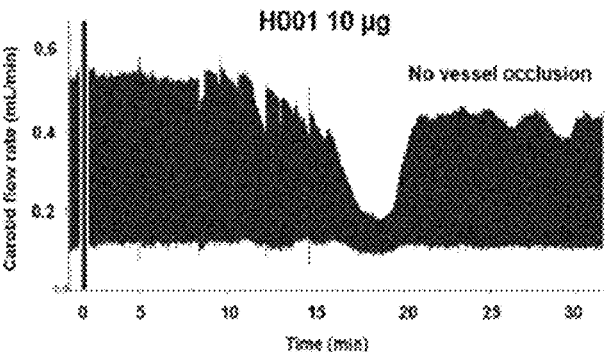
Figure 14:
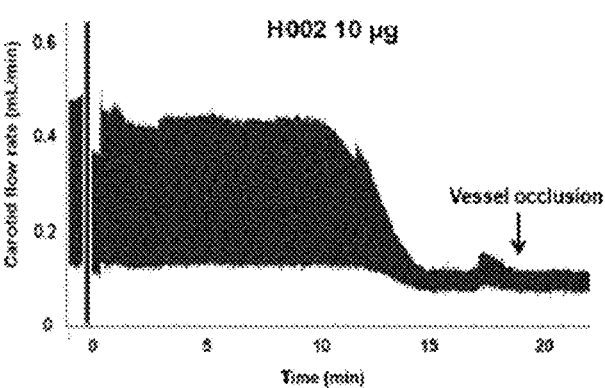
Figure 14:
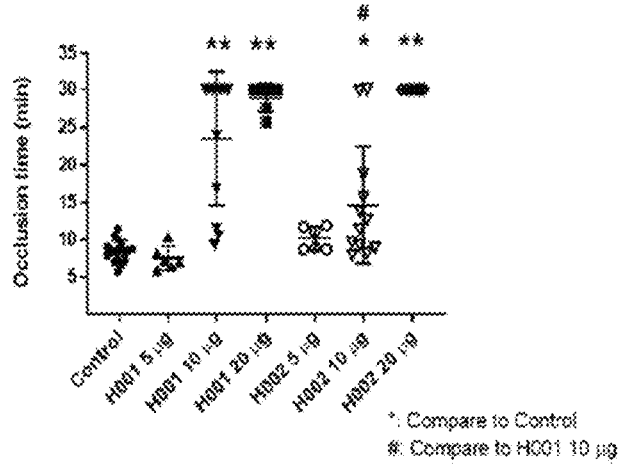

In a ferric chloride-induced large carotid artery thrombo-sis model, C57BL/6J wild-type mice (both genders, >8-week old, 25-30 g) were anesthetized and intravenously injected with Fab H001 or H002 antibody (5, 10 or 20 µg/mouse) or an equal volume (200 µL) of PBS 5 minutes before inducing arterial injury. The left common carotid artery was dissected and held with a miniature Doppler flow probe (TS420 transit-time perivascular flowmeter, Transonic Systems Inc., USA). The baseline blood flow rate was measured for 30 seconds. Carotid artery injury was then induced with a strip of Whatman filter paper saturated with 7.5% ferric chloride for 3 minutes. Blood flow was moni-tored until complete vessel occlusion was observed. The Fabs H001 and H002 antibodies significantly reduced thrombus growth and prevented stable vessel occlusion (FIG. 14).

In vivo decrease of the infarct size of ischemic brain without increasing the risk of intracerebral hemorrhage. To investigate the therapeutic potential of the antibodies in ischemic stroke, a cerebral ischemia and reperfusion injury model (transient middle cerebral artery occlusion (tMCAO)) was conducted. Male mice (25 g) were anesthetized with inhaled isofluorane. A midline neck incision was made and the soft tissues were pulled apart. The left common carotid artery (LCCA) was carefully dissected free from the sur-rounding nerves (without harming the vagal nerve) and a ligature was made using 5.0 string. The left external carotid artery (LECA) was then separated and a second knot was made. Next, the left internal carotid artery (LICA) was isolated and a knot was prepared with a 6.0 filament. After obtaining good view of the left internal carotid artery (LICA) and the left pterygopalatine artery (LPA), both arteries were clipped using a microvascular clip. A small hole was cut in the LCCA before it bifurcated to the LECA and the LICA. A standardized silicon rubber-coated 6.0 nylon monofilament (6021; Doccol Corp, Redlands, CA) was introduced into the LICA, until it stopped at the clip. The clipped arteries were opened while the filament was inserted into the LICA to occlude the origin of the LMCA in the circle of Willis. The third knot on the LICA was closed to fix the filament in position. After 1 hour, the third knot was opened and the filament was withdrawn. The antibodies were administered intravenously immediately after the fila-ment was inserted; or after 1 hour when the filament was withdrawn.

Figure 15:
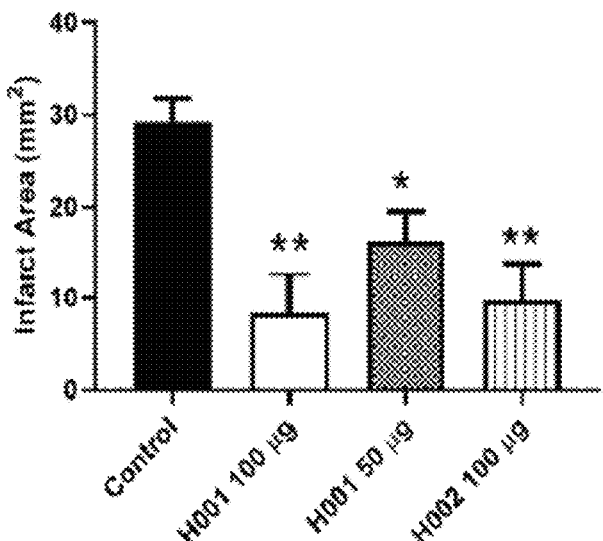
FIG. 15A to C show that the humanized Fabs H001 and H002 dramatically decreased the infarct size of the ischemic brain without increasing the risk of intracerebral hemorrhage in an cerebral ischemia and reperfusion injury mouse model (transient middle cerebral artery occlusion (tMCAO) model).
Figure 15:
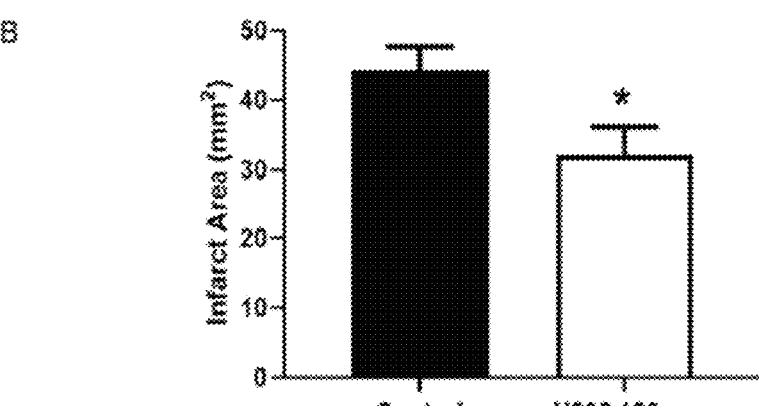
Figure 15:
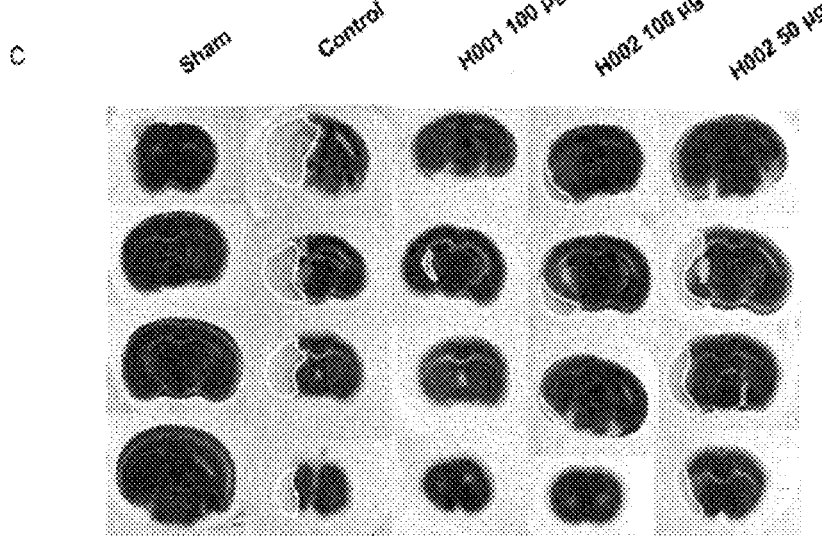

To measure cerebral infarct volumes, mice were euthan-ized 24 hours after induction of tMCAO. Multiple 2 mm-thick coronal brain sections cut from the whole brain were stained with 2% 2,3,5-triphenyl-tetrazolium chloride (TTC, Sigma-Aldrich, St Louis, MO) to visualize cerebral infarc-tions. The presence of cerebral hemorrhages was macro-scopically assessed. To measure the neurological function twenty-four hours after induction of tMCAO, mice were subjected to the modified Bederson test and the grip test to assess global neurological and motor function respectively. Results showed that blocking of GPIbα by the humanized Fabs H001 and H002 antibodies and scFv-HSA significantly reduced infarct size in the brain and improved functional outcome after tMCAO without increasing the risk of intrac-erebral hemorrhage (FIG. 15).

In vivo protection of TTP. To test the therapeutic effect of the antibodies in TTP, an ionophore-provoked ultra-large VWF (ULVWF)-mediated microvascular thrombosis model was used. ADAMTS13$^{-/-}$ mice were anesthetized and intra-venously injected with fluorescently labeled platelets puri-fied from the donor mice of the same genotype, and iono-phore-provoked microvascular thrombosis in mesenteric venules was monitored in real-time under intravital micros-copy. For platelet preparation, mice (6-8 weeks old) were anesthetized by intraperitoneal injection of ketamine/xyla-zine (100 mg/kg and 10 mg/kg body weight, respectively), and whole blood was collected from the retro-orbital plexus using heparin-coated glass capillary tubes. Blood was col-lected into a tube containing citrate-dextrose solution (38 mmol/L citric acid, 75 mmol/L trisodium citrate, 100 mmol/L dextrose). Platelet-rich plasma was obtained by centrifugation of whole blood at 300 g for 7 minutes. Gel-filtered platelets were then isolated from the platelet-rich plasma using a sepharose 2B column in PIPES buffer (PIPES 5 mmol/L, NaCl 1.37 mmol/L, KCl 4 mmol/L, and glucose 0.1%, pH 7.0). Platelet counts were confirmed using a Hemovet (HV950, Drew Scientific). Fluorescent labeling of gel-filtered platelets was achieved by incubating platelets with calcein-acetoxymethyl ester (1 µg/mL) for 15 minutes at room temperature. The efficacy of the fluorescent labeling of platelets was confirmed under fluorescent microscope before being used for in vivo imaging.

For intravital microscopy imaging, 4-week-old mice were anesthetized and injected with fluorescently labeled platelets (1.25×10$^6$ platelets/g from mice of the same genotype). Mesenteric vessels were surgically prepared and monitored under an inverted fluorescent microscope (Zeiss Axio Observer Z1 Advanced Marianas Microscope) using a 25× oil objective lens (Zeiss). An ≈2.5 mm section of the mesenteric venule (100 to 150 µmol/L in diameter) was topically treated with 10 µL of 10 µmol/L of calcium ionophore to induce Weibel-Palade body secretion of ULVWF from the endothelium, resulting in immediate adhe-sion of fluorescently labeled platelets and formation of platelet thrombi anchored to the vessel wall. For each mouse, the process of thrombosis and the resolution of thrombi were monitored and recorded for 20 minutes in addition to prerecording. The Fab H001 or the scFv-HSA chimeric protein was administered via tail vein catheter 10 minutes before (prophylactic) the onset of thrombosis by calcium ionophore stimulation in mesenteric microvascula-ture in ADAMTS13$^{-/-}$ The dynamics of platelet accumula-tion in selected vessel segments was quantitatively analyzed by (1) number of emboli (platelet thrombi larger than 20 µm in diameter), and (2) time to restore normal blood flow: defined as the time required for platelet fluorescence to return to near baseline after the topical application.

Figure 16:
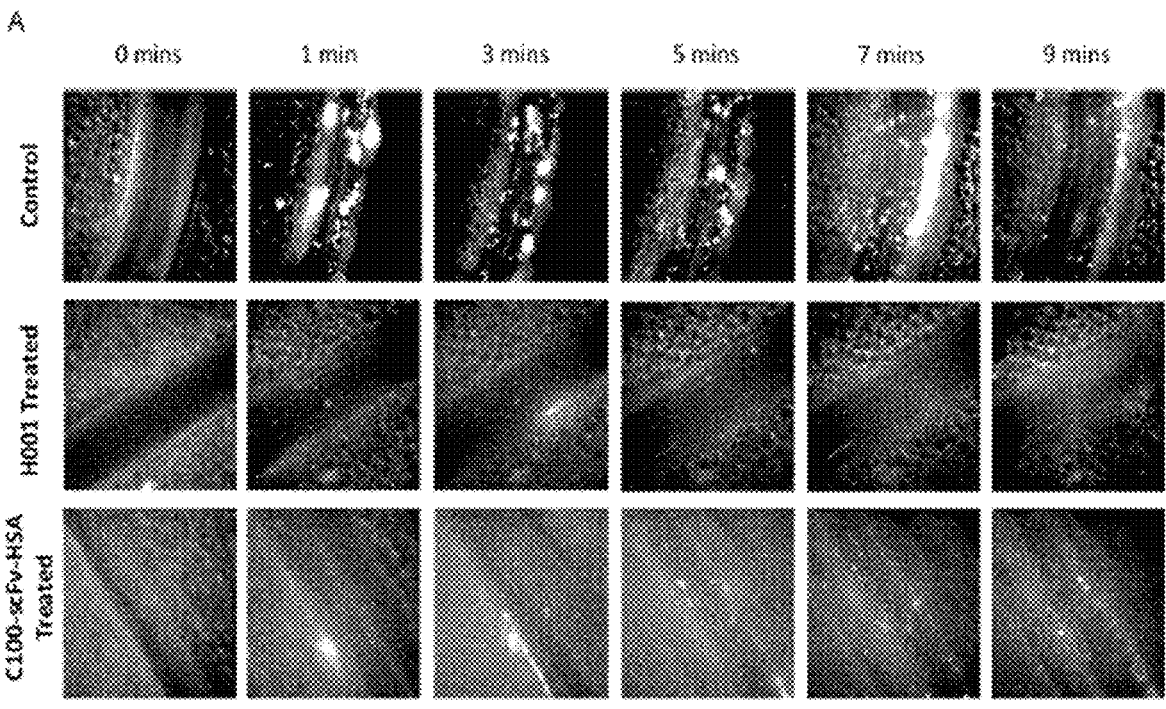
FIG. 16A to B show that prophylactic treatment of ADAMTS13⁻/⁻ mice with the humanized Fab H001 or the humanized C100-scFv fused with human albumin (C100-scFv-HSA) effectively inhibited ionophore-provoked VWF-mediated microvascular thrombosis in a mouse model of TTP.
(FIG. 16C) Histogram showing the time to restore normal blood flow in function of the antibody or the doses used. *P<0.05, ** P<0.01.
Figure 16:
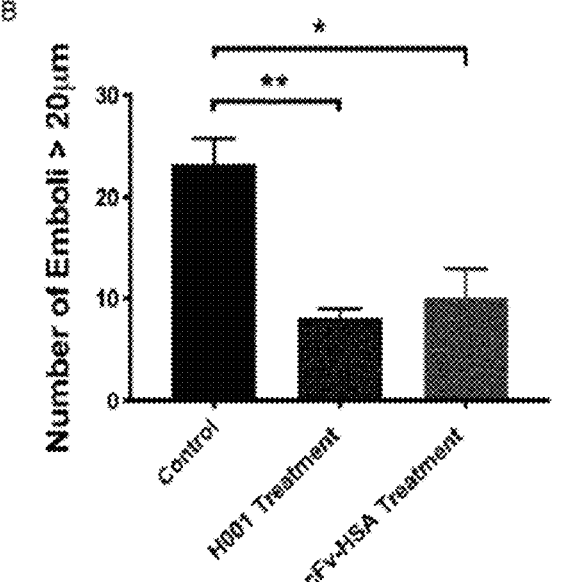
Figure 16:
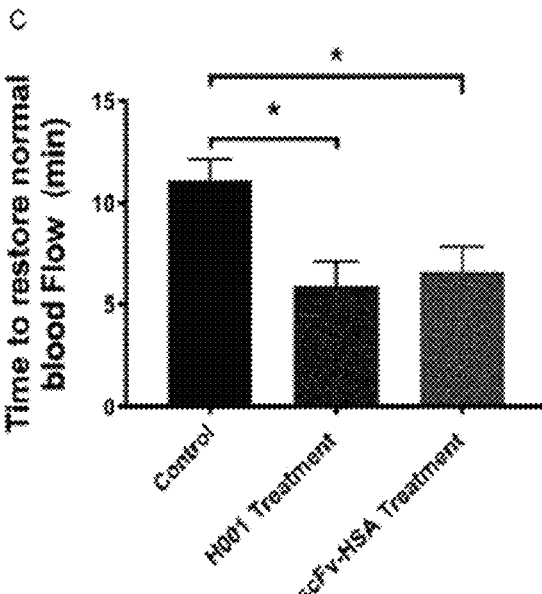

As shown in the FIG. 16, no platelet adhesion to the mesenteric vessel wall was detected under intravital microscopy prior to the application of ionophore in all ADAMTS13$^{-/-}$ mice that treated with saline (control), the Fab H001 antibody, or the scFv-HSA chimeric protein. Immediately after the topical application of calcium ionophore to the mesenteric vessel in control ADAMTS13$^{-/-}$ mice, platelet adhesion was observed onto mesenteric venules, presented as single platelet strings formation attached to endothelial in the direction of blood flow. Within a minute, multiple large thrombi (>20 μm in diameter) formed and some grew up to 50% of the diameter of the ionophore-treated vessels. Platelet string and thrombi were visibly very loose and easily detach from vessel wall and emboli to downstream. Platelet adhesion to vessel wall and embolitic thrombosis in control mice continued up to 10 minutes or more but deceased over the time and ultimately restored the normal blood flow in effected section of the vessel. The thrombotic response in ADAMTS13$^{-/-}$ mice was dramatically inhibited by prophylactic treatment of both the Fab H001 antibody or the scFv-HSA chimeric protein (FIG. 16). Platelet adhesion onto vessel wall and formation of large thrombi were strongly inhibited by both the Fab H001 antibody or the scFv-HSA chimeric protein treatment (FIG. 16). The numbers of large emboli thrombi were significantly less and the time to restore normal blood flow in mesenteric venules as shorter in both in the Fab H001 antibody or the scFv-HSA chimeric protein treated group when compared to control group (FIG. 16). These results demonstrated that prophylactic treatment of ADAMTS13$^{-/-}$ mice with the Fab H001 antibody or the scFv-HSA chimeric protein effectively inhibited ionophore-provoked VWF-mediated microvascular thrombosis, mimicking platelet accumulation on newly released endothelial-bound ULVWF in TTP.

Figure 17:
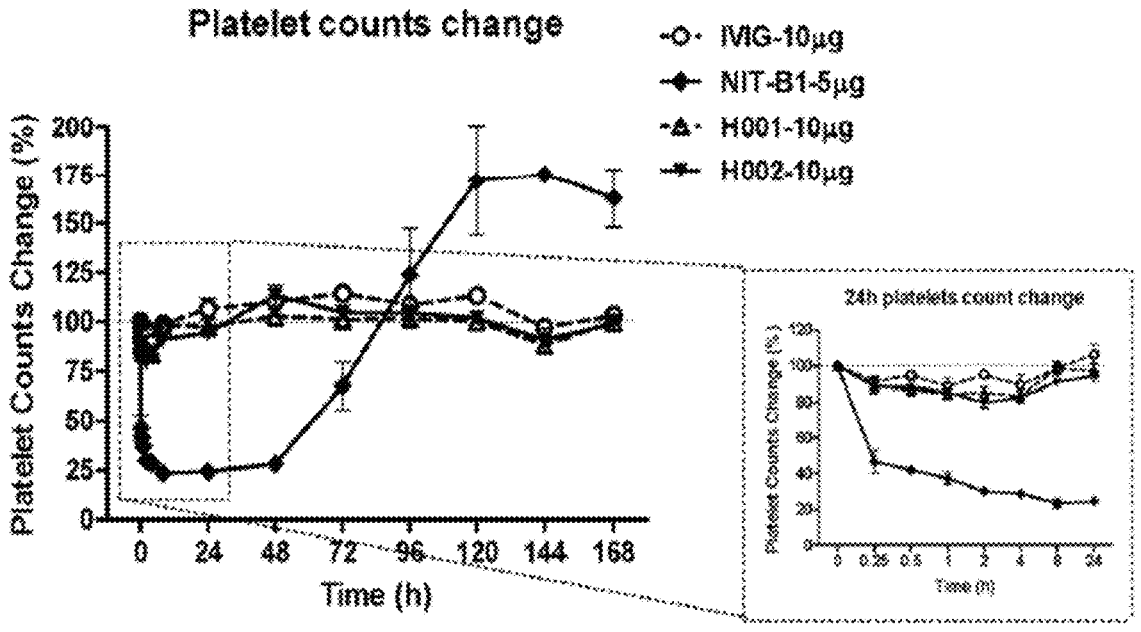
FIG. 17 shows that the humanized Fabs H001 and H002 antibodies did not induce thrombocytopenia. Results are shown as the platelet counts change (in %) in function of time (hours) and antibody treatment: IVIG (o), NIT-B1 (♦), H001 (Δ) or H002 (▼).

Inhibition of thrombocytopenia. C57BL/6 mice were injected intravenously with intravenous immunoglobulins (IVIg), the humanized Fab H001 or H002 antibody (10

μg/mouse, n=3 each group), or the NIT-B1 antibody (5 μg/mouse, n=2). A series of blood samples at different time points (0, 30 min, 1, 2, 4, 8 hours, 1, 2, 3, 4, 5, 6 and 7 days) were collected from mice medial saphenous vein. At each time point, 10 μL blood sample were collected and added into 240 μL 1% PBS-EDTA (pH 7.4) to prevent clotting. For platelets counting, 50 μL blood sample (in PBS-EDTA) was transferred into 10 mL diluent (Isoton II, Coulter Corporation) and the platelets count was determined using a Coulter counter (Beckman Z2, Coulter Corporation). As shown in FIG. 17, the humanized and monovalent H001 or H002 antibodies did not induce a significant loss in platelet count in the first 24 h following their administration which is in clear contrast to the NIT-B1 antibody.

Figure 18:
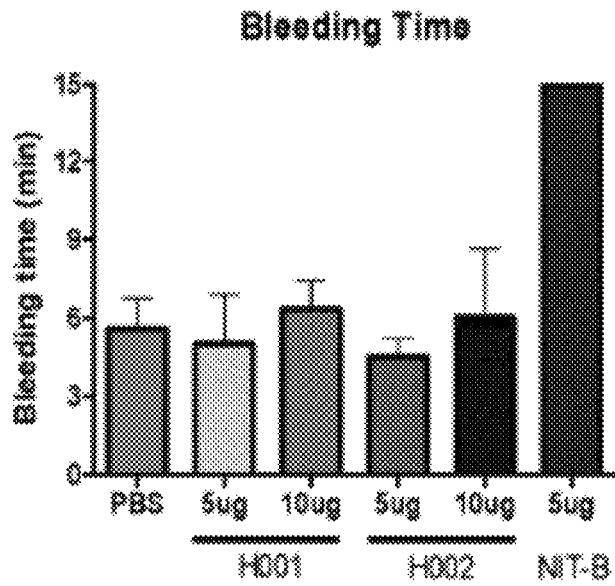
FIG. 18 shows that the humanized Fabs H001 and H002 antibodies did not prolong the bleeding time whereas the murine NIT-B markedly increase the bleeding time. Results are shown as the bleeding time (in minutes) in function of treatment and dose (as indicated below the X axis).

Bleeding time. BALB/c mice were injected intravenously with PBS (n=4), the Fab H001 or H002 antibody (5-10 ug/mouse, n=3) 120 mins before injury. Mice were anesthetized by 2.5% avertine (18 mL/kg body weight, i.p.), and maintained on a 37° C. heating pad. The tip of the tail (2 mm) was cut off with a sharp scalpel and a tissue paper was used to tap wound every 15 seconds. Bleeding time was recorded as the time to cessation of blood flow (bleeding stopped for >10 s). The assay was terminated after 15 minutes if the tail was still bleeding. As shown in FIG. 18, the administration of the H001 or the H002 antibody did not prolong bleeding time.

REFERENCES

Yaghoub Safdari, Safar Farajnia, Mohammad Asgharzadeh & Masoumeh Khalili (2013) Antibody humanization methods—a review and update, Biotechnology and Genetic Engineering Reviews, 29:2, 175-186

While the invention has been described in connection with specific embodiments thereof, it will be understood that the scope of the claims should not be limited by the preferred embodiments set forth in the examples, but should be given the broadest interpretation consistent with the description as a whole.

What is claimed is:

1. A humanized antibody or fragment thereof specifically recognizing platelet glycoprotein I(b)α (GPIbα), wherein a Fc moiety is present or absent, wherein the humanized antibody or fragment thereof:

is capable of preventing platelet activation, aggregation, and/or thrombus growth;

lacks the ability to activate platelets;

lacks the ability to induce thrombocytopenia; and/or at a therapeutic dose, lacks the ability to prolong bleeding time;

wherein the humanized antibody or fragment thereof has a heavy chain and a light chain comprising:

i) the heavy chain variable region having an amino acid sequence of QVQLVESGGGLVKPGGSLRLS-CAASGFTFSSFAMSWIRQAPGKGLEWVSSITSAG TPYYPDSVLGRFTISRDNAKNSLYLQMNSLRAE-DTAVYYCARSRGYEDYFDYW GQGTLVTVSS (SEQ ID NO: 93); and the light chain variable region having an amino acid of sequence DIQMTQSPSSL-SASVGDRVTITCKSSQSLLNSRNOK-NYLAWYQQKPGKAPKLLIY FTSTRESGVPSRFSGSGSGTDFTLTISSLOPEDFA-TYYCQQHYSSPWTFGQGTKVE IK (SEQ ID NO: 95); or ii) the heavy chain variable region having an amino acid sequence of QVQLVESGGGLVKPGGSLRLS-CAASGFTFSSFAMSWIRQAPGKGLEWVSSITSAG TPYYPDSVLGRFTISRDNAKNSLYLQMNSLRAE-DTAVYYCARSRGYEDYFDYW GQGTLVTVSS (SEQ ID NO: 93); and the light chain variable region having an amino acid of sequence DIVMTQSPLSLPVTPGEPASISCKSSQSLLN-SRNQKNYLAWYLOKPGQSPOLLIYF TSTRESGVPDRFSGSGSGTDFTLKISRVEAE-DVGVYYCQQHYSSPWTFGQGTKVE IK (SEQ ID NO: 96); or iii) the heavy chain variable region having an amino acid sequence of QVOLVESGGGVVQPGRSLRLS-CAASGFTFSSFAMSWVRQAPGKGLEWVASITSA GTPYYPDSVLGRFTISRDNSKNTLYLQMNSL-RAEDTAVYYCARSRGYEDYFDY WGQGTLVTVSS (SEQ ID NO: 94); and the light chain variable region having an amino sequence acid of DIVMTQSPLSLPVTPGEPASISCKSSQSLLN-SRNQKNYLAWYLOKPGOSPQLLIYF TSTRESGVPDRFSGSGSGTDFTLKISRVEAE-DVGVYYCQQHYSSPWTFGQGTKVE IK (SEQ ID NO: 96);

and wherein the humanize antibody or fragment thereof comprises:

a first heavy chain CDR having the amino acid sequence of SEQ ID NO: 37;

a second heavy chain CDR having the amino acid sequence of SEQ ID NO: 38;

a third heavy chain CDR having the amino acid sequence of SEQ ID NO: 39;

a first light chain CDR having the amino acid sequence of SEQ ID NO: 65;

a second light chain CDR having the amino acid sequence of SEQ ID NO: 66; and a third light chain CDR having the amino acid sequence of SEQ ID NO: 67.

2. The humanized antibody or fragment thereof of claim 1 being capable of recognizing a human GPIbα, a mouse GPIbα, a dog GPIbα, a rat GPIbα, a rabbit GPIbα and/or a monkey GPIbα.

3. The humanized antibody or fragment thereof of claim 1 being an antibody fragment.

4. The humanized antibody or fragment thereof of claim 3 being a F(ab)₂ fragment.

5. The humanized antibody or fragment thereof of claim 3, wherein the antibody is a monovalent antibody.

6. The humanized antibody or fragment thereof of claim 5 being a Fab antibody fragment.

7. The humanized antibody or fragment thereof of claim 5 being a single chain variable fragment (scFv).

8. The humanized antibody or fragment thereof of claim 1, wherein the heavy chain further comprises a CH1 region of a human IgG₁ antibody, wherein the CH1 region of the human IgG₁ antibody has the amino acid sequence of SEQ ID NO: 40 or 61.

9. The humanized antibody or fragment thereof of claim 8, wherein the heavy chain has the amino acid sequence of SEQ ID NO: 36 or 57.

10. The humanized antibody or fragment thereof of claim 1, wherein the light chain further comprises a kappa chain C region of a human IgG₁ antibody, wherein the kappa chain C region has the amino acid sequence of SEQ ID NO: 75 or 82.

11. The humanized antibody or fragment thereof of claim 10, wherein the light chain has the amino acid sequence of SEQ ID NO: 71 or 78.

12. The humanized antibody or fragment thereof of claim 1 having:

the heavy chain of SEQ ID NO: 36 and the light chain of SEQ ID NO: 71;

the heavy chain of SEQ ID NO: 36 and the light chain of SEQ ID NO: 78; or the heavy chain of SEQ ID NO: 57 and the light chain of SEQ ID NO: 78.

13. A chimeric protein comprising the humanized antibody or fragment thereof of claim 1 and a carrier protein.

14. A pharmaceutical composition comprising (i) the humanized antibody or fragment thereof of claim 1 or the chimeric protein of claim 13 and (ii) a pharmaceutical excipient.

15. A method of preventing or limiting the interaction between glycoprotein I(b)α (GPIbα) present on a platelet and a GPIbα ligand, the method comprising contacting the humanized antibody or fragment thereof of claim 1, the chimeric protein of claim 13 or the pharmaceutical composition of claim 14 with the platelet.

16. The method of claim 15 for preventing or limiting platelet activation.

17. The method of claim 15, wherein the GPIbα ligand is von Willebrand factor (VWF), P-selectin, kininogen, thrombospondin and/or thrombin.

18. The method of claim 15, wherein the contacting occurs under high or low shear rates.

19. The method of any claim 15, wherein the humanized antibody, the chimeric protein or the pharmaceutical composition is contacted with the platelet prior to, at the same time or after the GPIbα ligand is contacted with the platelet.

20. The method of claim 15 for preventing or limiting the interaction in vivo in a subject in need thereof, wherein the subject is at risk of experiencing or has experienced a pathological thrombosis.

21. The method of claim 20 for preventing the formation or the growth of a thrombus, for reducing the size of a thrombus, or for reducing the number of thrombi, or for dissolving an occluded thrombus in the subject in need thereof.

22. The method of claim 21, further comprising determining the presence, the location and/or the size of the thrombus in the subject.

23. The method of claim 20, wherein the subject is at risk of experiencing or has experienced an ischemic stroke, a thrombotic thrombocytopenic purpura, a myocardial infarct, an acute coronary syndrome, atherothrombosis, a peripheral vascular disease, deep vein thrombosis, sepsis, and/or a vascular inflammation.

24. The method of claim 20 for reducing or limiting tumor metastasis in the subject in need thereof.

25. The method of claim 24 further comprising determining the presence, the location and/or the size of the tumor metastasis in the subject.

26. The humanized antibody or fragment thereof of claim 1, lacking a Fc moiety.

* * * * *

SEQUENCE LISTING

```
<160> NUMBER OF SEQ ID NOS: 96

<210> SEQ ID NO 1
<211> LENGTH: 137
<212> TYPE: PRT
<213> ORGANISM: Artificial Sequence
<220> FEATURE:
<223> OTHER INFORMATION: NIT-A1 Heavy chain variable domain with signal
      sequence

<400> SEQUENCE: 1

Met Asn Phe Gly Phe Ser Leu Ile Phe Leu Val Leu Val Leu Lys Gly
1               5                   10                  15

Val Gln Cys Glu Val Lys Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Phe Ala Met Ser Trp Ile Arg Arg Thr Pro Glu Lys Ser Leu
    50                  55                  60

Glu Trp Val Ala Ser Ile Thr Ser Ala Gly Thr Pro Tyr Tyr Val Asp
65                  70                  75                  80

Ser Val Met Gly Arg Phe Thr Ile Ser Arg Asp Tyr Ala Gly Asn Ile
                85                  90                  95
```

```
Leu Tyr Leu Gln Met Ser Ser Leu Arg Ser Glu Asp Thr Ala Met Tyr
            100                 105                 110

Tyr Cys Thr Arg Ser Arg Gly Tyr Glu Asp Tyr Phe Asp Tyr Trp Gly
        115                 120                 125

Gln Gly Thr Thr Leu Thr Val Ser Ser
    130                 135

<210> SEQ ID NO 2
<211> LENGTH: 118
<212> TYPE: PRT
<213> ORGANISM: Artificial Sequence
<220> FEATURE:
<223> OTHER INFORMATION: NIT-A1 Heavy chain variable domain without
      signal sequence

<400> SEQUENCE: 2

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Ile Arg Arg Thr Pro Glu Lys Ser Leu Glu Trp Val
        35                  40                  45

Ala Ser Ile Thr Ser Ala Gly Thr Pro Tyr Tyr Val Asp Ser Val Met
    50                  55                  60

Gly Arg Phe Thr Ile Ser Arg Asp Tyr Ala Gly Asn Ile Leu Tyr Leu
65                  70                  75                  80

Gln Met Ser Ser Leu Arg Ser Glu Asp Thr Ala Met Tyr Tyr Cys Thr
                85                  90                  95

Arg Ser Arg Gly Tyr Glu Asp Tyr Phe Asp Tyr Trp Gly Gln Gly Thr
            100                 105                 110

Thr Leu Thr Val Ser Ser
        115

<210> SEQ ID NO 3
<211> LENGTH: 10
<212> TYPE: PRT
<213> ORGANISM: Artificial Sequence
<220> FEATURE:
<223> OTHER INFORMATION: NIT-A1 Heavy chain CDR1

<400> SEQUENCE: 3

Gly Phe Thr Phe Ser Ser Phe Ala Met Ser
1               5                   10

<210> SEQ ID NO 4
<211> LENGTH: 16
<212> TYPE: PRT
<213> ORGANISM: Artificial Sequence
<220> FEATURE:
<223> OTHER INFORMATION: NIT-A1 Heavy chain CDR2

<400> SEQUENCE: 4

Ser Ile Thr Ser Ala Gly Thr Pro Tyr Tyr Val Asp Ser Val Met Gly
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: NIT-A1 Heavy chain CDR3

<400> SEQUENCE: 5
```

-continued

```
Ser Arg Gly Tyr Glu Asp Tyr Phe Asp Tyr
1               5                   10

<210> SEQ ID NO 6
<211> LENGTH: 137
<212> TYPE: PRT
<213> ORGANISM: Artificial Sequence
<220> FEATURE:
<223> OTHER INFORMATION: NIT-B1 Heavy chain variable domain with signal
      sequence

<400> SEQUENCE: 6

Met Asn Phe Gly Phe Ser Leu Ile Phe Leu Val Leu Val Leu Lys Gly
1               5                   10                  15

Val Gln Cys Glu Val Lys Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45

Ser Ser Phe Ala Met Ser Trp Ile Arg Arg Thr Pro Glu Lys Ser Leu
        50                  55                  60

Glu Trp Val Ala Ser Ile Thr Ser Ala Gly Thr Pro Tyr Tyr Pro Asp
65                  70                  75                  80

Ser Val Leu Gly Arg Phe Thr Ile Ser Arg Asp Tyr Ala Gly Asn Ile
                85                  90                  95

Leu Tyr Leu Leu Met Ser Ser Leu Arg Ser Glu Asp Thr Ala Met Tyr
            100                 105                 110

Tyr Cys Thr Arg Ser Arg Gly Tyr Glu Asp Tyr Phe Asp Tyr Trp Gly
        115                 120                 125

Gln Gly Thr Thr Leu Thr Val Ser Ser
    130                 135

<210> SEQ ID NO 7
<211> LENGTH: 118
<212> TYPE: PRT
<213> ORGANISM: Artificial Sequence
<220> FEATURE:
<223> OTHER INFORMATION: NIT-B1 Heavy chain variable domain without
      signal sequence

<400> SEQUENCE: 7

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Ile Arg Arg Thr Pro Glu Lys Ser Leu Glu Trp Val
        35                  40                  45

Ala Ser Ile Thr Ser Ala Gly Thr Pro Tyr Tyr Pro Asp Ser Val Leu
        50                  55                  60

Gly Arg Phe Thr Ile Ser Arg Asp Tyr Ala Gly Asn Ile Leu Tyr Leu
65                  70                  75                  80

Leu Met Ser Ser Leu Arg Ser Glu Asp Thr Ala Met Tyr Tyr Cys Thr
                85                  90                  95

Arg Ser Arg Gly Tyr Glu Asp Tyr Phe Asp Tyr Trp Gly Gln Gly Thr
            100                 105                 110

Thr Leu Thr Val Ser Ser
        115

<210> SEQ ID NO 8
```

```
<211> LENGTH: 10
<212> TYPE: PRT
<213> ORGANISM: Artificial Sequence
<220> FEATURE:
<223> OTHER INFORMATION: NIT-B1 Heavy chain CDR1

<400> SEQUENCE: 8

Gly Phe Thr Phe Ser Ser Phe Ala Met Ser
1               5                   10

<210> SEQ ID NO 9
<211> LENGTH: 16
<212> TYPE: PRT
<213> ORGANISM: Artificial Sequence
<220> FEATURE:
<223> OTHER INFORMATION: NIT-B1 Heavy chain CDR2

<400> SEQUENCE: 9

Ser Ile Thr Ser Ala Gly Thr Pro Tyr Tyr Pro Asp Ser Val Leu Gly
1               5                   10                  15

<210> SEQ ID NO 10
<211> LENGTH: 10
<212> TYPE: PRT
<213> ORGANISM: Artificial Sequence
<220> FEATURE:
<223> OTHER INFORMATION: NIT-B1 Heavy chain CDR3

<400> SEQUENCE: 10

Ser Arg Gly Tyr Glu Asp Tyr Phe Asp Tyr
1               5                   10

<210> SEQ ID NO 11
<211> LENGTH: 133
<212> TYPE: PRT
<213> ORGANISM: Artificial Sequence
<220> FEATURE:
<223> OTHER INFORMATION: NIT-A1 Light chain variable domain with signal
      sequence

<400> SEQUENCE: 11

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Leu Ser Cys Lys Ser Ser Gln Ser
        35                  40                  45

Leu Leu Asn Ser Arg Asn Gln Lys Asn Tyr Leu Ala Trp Tyr Gln Gln
    50                  55                  60

Lys Pro Gly Gln Ser Pro Lys Leu Leu Ile Tyr Phe Thr Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Ser Pro Trp Thr Phe Gly Gly Gly Thr
        115                 120                 125

Lys Leu Glu Ile Lys
    130

<210> SEQ ID NO 12
<211> LENGTH: 113
<212> TYPE: PRT
```

-continued

```
<213> ORGANISM: Artificial Sequence
<220> FEATURE:
<223> OTHER INFORMATION: NIT-A1 Light chain variable domain without
      signal sequence

<400> SEQUENCE: 12

Asp Ile Val Met Thr Gln Ser Pro Ser Ser Leu Ala Met Ser Val Gly
1               5                   10                  15

Gln Lys Val Thr Leu Ser Cys Lys Ser Ser Gln Ser Leu Leu Asn Ser
            20                  25                  30

Arg Asn Gln Lys Asn Tyr Leu Ala Trp Tyr Gln Gln Lys Pro Gly Gln
        35                  40                  45

Ser Pro Lys Leu Leu Ile Tyr Phe Thr Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ser Pro Trp Thr Phe Gly Gly Gly Thr Lys Leu Glu Ile
            100                 105                 110

Lys

<210> SEQ ID NO 13
<211> LENGTH: 17
<212> TYPE: PRT
<213> ORGANISM: Artificial Sequence
<220> FEATURE:
<223> OTHER INFORMATION: NIT-A1 Light chain CDR1

<400> SEQUENCE: 13

Lys Ser Ser Gln Ser Leu Leu Asn Ser Arg Asn Gln Lys Asn Tyr Leu
1               5                   10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: NIT-A1 Light chain CDR2

<400> SEQUENCE: 14

Phe Thr Ser Thr Arg Glu Ser
1               5

<210> SEQ ID NO 15
<211> LENGTH: 9
<212> TYPE: PRT
<213> ORGANISM: Artificial Sequence
<220> FEATURE:
<223> OTHER INFORMATION: NIT-A1 Light chain CDR3

<400> SEQUENCE: 15

Gln Gln His Tyr Ser Ser Pro Trp Thr
1               5

<210> SEQ ID NO 16
<211> LENGTH: 133
<212> TYPE: PRT
<213> ORGANISM: Artificial Sequence
<220> FEATURE:
<223> OTHER INFORMATION: NIT-B1 Light chain variable domain with signal
      sequence
```

-continued

<400> SEQUENCE: 16

```
Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Leu Ser Cys Lys Ser Ser Gln Ser
        35                  40                  45

Leu Leu Asn Ser Arg Asn Gln Lys Asn Tyr Leu Ala Trp Tyr Gln Gln
        50                  55                  60

Lys Pro Gly Gln Ser Pro Lys Leu Leu Ile Tyr Phe Thr Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Ser Pro Trp Thr Phe Gly Gly Gly Thr
            115                 120                 125

Lys Leu Glu Ile Lys
    130
```

<210> SEQ ID NO 17
<211> LENGTH: 113
<212> TYPE: PRT
<213> ORGANISM: Artificial Sequence
<220> FEATURE:
<223> OTHER INFORMATION: NIT B1 Light chain vairable domain without
      signal sequence

<400> SEQUENCE: 17

```
Asp Ile Val Met Thr Gln Ser Pro Ser Ser Leu Ala Met Ser Val Gly
1               5                   10                  15

Gln Lys Val Thr Leu Ser Cys Lys Ser Ser Gln Ser Leu Leu Asn Ser
            20                  25                  30

Arg Asn Gln Lys Asn Tyr Leu Ala Trp Tyr Gln Gln Lys Pro Gly Gln
        35                  40                  45

Ser Pro Lys Leu Leu Ile Tyr Phe Thr Ser Thr Arg Glu Ser Gly Val
        50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ser Pro Trp Thr Phe Gly Gly Gly Thr Lys Leu Glu Ile
            100                 105                 110

Lys
```

<210> SEQ ID NO 18
<211> LENGTH: 17
<212> TYPE: PRT
<213> ORGANISM: Artificial Sequence
<220> FEATURE:
<223> OTHER INFORMATION: NIT-B1 Light chain CDR1

<400> SEQUENCE: 18

```
Lys Ser Ser Gln Ser Leu Leu Asn Ser Arg Asn Gln Lys Asn Tyr Leu
1               5                   10                  15

Ala
```

```
<210> SEQ ID NO 19
<211> LENGTH: 7
<212> TYPE: PRT
<213> ORGANISM: Artificial Sequence
<220> FEATURE:
<223> OTHER INFORMATION: NIT-B1 Light chain CDR2

<400> SEQUENCE: 19

Phe Thr Ser Thr Arg Glu Ser
1               5

<210> SEQ ID NO 20
<211> LENGTH: 9
<212> TYPE: PRT
<213> ORGANISM: Artificial Sequence
<220> FEATURE:
<223> OTHER INFORMATION: NIT-B1 Light chain CDR3

<400> SEQUENCE: 20

Gln Gln His Tyr Ser Ser Pro Trp Thr
1               5

<210> SEQ ID NO 21
<211> LENGTH: 241
<212> TYPE: PRT
<213> ORGANISM: Artificial Sequence
<220> FEATURE:
<223> OTHER INFORMATION: Chimeric C100 Heavy chain with signal sequence

<400> SEQUENCE: 21

Met Gly Trp Ser Cys Ile Ile Leu Phe Leu Val Ala Thr Ala Thr Gly
1               5                   10                  15

Val His Ser Glu Val Lys Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45

Ser Ser Phe Ala Met Ser Trp Ile Arg Arg Thr Pro Glu Lys Ser Leu
        50                  55                  60

Glu Trp Val Ala Ser Ile Thr Ser Ala Gly Thr Pro Tyr Tyr Pro Asp
65                  70                  75                  80

Ser Val Leu Gly Arg Phe Thr Ile Ser Arg Asp Tyr Ala Gly Asn Ile
                85                  90                  95

Leu Tyr Leu Leu Met Ser Ser Leu Arg Ser Glu Asp Thr Ala Met Tyr
            100                 105                 110

Tyr Cys Thr Arg Ser Arg Gly Tyr Glu Asp Tyr Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
```

-continued

```
225                 230                 235                 240

Asp

<210> SEQ ID NO 22
<211> LENGTH: 222
<212> TYPE: PRT
<213> ORGANISM: Artificial Sequence
<220> FEATURE:
<223> OTHER INFORMATION: Chimeric C100 Heavy chain without signal

<400> SEQUENCE: 22

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Ile Arg Arg Thr Pro Glu Lys Ser Leu Glu Trp Val
            35                  40                  45

Ala Ser Ile Thr Ser Ala Gly Thr Pro Tyr Tyr Pro Asp Ser Val Leu
        50                  55                  60

Gly Arg Phe Thr Ile Ser Arg Asp Tyr Ala Gly Asn Ile Leu Tyr Leu
65                  70                  75                  80

Leu Met Ser Ser Leu Arg Ser Glu Asp Thr Ala Met Tyr Tyr Cys Thr
                85                  90                  95

Arg Ser Arg Gly Tyr Glu Asp Tyr Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp
        210                 215                 220

<210> SEQ ID NO 23
<211> LENGTH: 10
<212> TYPE: PRT
<213> ORGANISM: Artificial Sequence
<220> FEATURE:
<223> OTHER INFORMATION: Chimeric C100 Heavy chain CDR1

<400> SEQUENCE: 23

Gly Phe Thr Phe Ser Ser Phe Ala Met Ser
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Chimeric C100 Heavy chain CDR2

<400> SEQUENCE: 24
```

```
Ser Ile Thr Ser Ala Gly Thr Pro Tyr Tyr Pro Asp Ser Val Leu Gly
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: Chimeric C100 Heavy chain CDR3

<400> SEQUENCE: 25

Ser Arg Gly Tyr Glu Asp Tyr Phe Asp Tyr
1               5                   10

<210> SEQ ID NO 26
<211> LENGTH: 104
<212> TYPE: PRT
<213> ORGANISM: Artificial Sequence
<220> FEATURE:
<223> OTHER INFORMATION: Human IgG1 CH1 region found in SEQ ID NO: 21
      and 22

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 27
<211> LENGTH: 743
<212> TYPE: DNA
<213> ORGANISM: Artificial Sequence
<220> FEATURE:
<223> OTHER INFORMATION: HEK293-6E codon optimized nucleic acid sequence
      encoding SEQ ID NO: 21

<400> SEQUENCE: 27
gaattcccgc cgccaccatg ggctggtcct gcatcatcct cttcctcgtc gccaccgcca      60
ccggcgtcca ctccgaggtc aagctcgtcg agtccggcgg cgacctcgtc aagcccggcg     120
gctccctcaa gctctcctgc gccgcctccg gcttcacctt ctcctccttc gccatgtcct     180
ggatccgccg cacccccgag aagtccctcg agtgggtcgc ctccatcacc tccgccggca     240 cccctacta ccccgactcc gtcctcggcc gcttcaccat ctcccgcgac tacgccggca     300
acatcctcta cctcctcatg tcctccctcc gctccgagga caccgccatg tactactgca     360
cccgctcccg cggctacgag gactacttcg actactgggg ccagggcacc accctcaccg     420
tctcctccgc ctccaccaag ggcccctccg tcttcccccct cgccccctcc tccaagtcca     480
cctccggcgg caccgccgcc ctcggctgcc tcgtcaagga ctacttcccc gagcccgtca     540
ccgtctcctg gaactccggc gccctcacct ccggcgtcca caccttcccc gccgtcctcc     600
```

```
agtcctccgg cctctactcc ctctcctccg tcgtcaccgt cccctcctcc tccctcggca      660
cccagaccta catctgcaac gtcaaccaca agccctccaa caccaaggtc gacaagaagg      720
tcgagcccaa gtcctgcgac tga                                              743
```

```
<210> SEQ ID NO 28
<211> LENGTH: 239
<212> TYPE: PRT
<213> ORGANISM: Artificial Sequence
<220> FEATURE:
<223> OTHER INFORMATION: Chimeric C100 Light chain with signal sequence

<400> SEQUENCE: 28

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Ala Met
                20                  25                  30

Ser Val Gly Gln Lys Val Thr Leu Ser Cys Lys Ser Ser Gln Ser Leu
        35                  40                  45

Leu Asn Ser Arg Asn Gln Lys Asn Tyr Leu Ala Trp Tyr Gln Gln Lys
    50                  55                  60

Pro Gly Gln Ser Pro Lys Leu Leu Ile Tyr Phe Thr Ser Thr Arg Glu
65                  70                  75                  80

Ser Gly Val Pro Asp Arg Phe Ile Gly Ser Gly Ser Gly Thr Asp Phe
                85                  90                  95

Thr Leu Thr Ile Ser Ser Val Gln Ala Glu Asp Leu Ala Asp Tyr Phe
                100                 105                 110

Cys Gln Gln His Tyr Ser Ser Pro Trp Thr Phe Gly Gly Gly Thr Lys
                115                 120                 125

Leu Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235
```

```
<210> SEQ ID NO 29
<211> LENGTH: 220
<212> TYPE: PRT
<213> ORGANISM: Artificial Sequence
<220> FEATURE:
<223> OTHER INFORMATION: Chimeric C100 Light chain without signal
      sequence

<400> SEQUENCE: 29

Asp Ile Val Met Thr Gln Ser Pro Ser Ser Leu Ala Met Ser Val Gly
1               5                   10                  15

Gln Lys Val Thr Leu Ser Cys Lys Ser Ser Gln Ser Leu Leu Asn Ser
                20                  25                  30

Arg Asn Gln Lys Asn Tyr Leu Ala Trp Tyr Gln Gln Lys Pro Gly Gln
```

-continued

```
           35                  40                  45
Ser Pro Lys Leu Leu Ile Tyr Phe Thr Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ser Pro Trp Thr Phe Gly Gly Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 30
<211> LENGTH: 17
<212> TYPE: PRT
<213> ORGANISM: Artificial Sequence
<220> FEATURE:
<223> OTHER INFORMATION: Chimeric C100 Light chain CDR1

<400> SEQUENCE: 30

Lys Ser Ser Gln Ser Leu Leu Asn Ser Arg Asn Gln Lys Asn Tyr Leu
1               5                   10                  15

Ala

<210> SEQ ID NO 31
<211> LENGTH: 7
<212> TYPE: PRT
<213> ORGANISM: Artificial Sequence
<220> FEATURE:
<223> OTHER INFORMATION: Chimeric C100 Light chain CDR2

<400> SEQUENCE: 31

Phe Thr Ser Thr Arg Glu Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Chimeric C100 Light chain CDR3

<400> SEQUENCE: 32

Gln Gln His Tyr Ser Ser Pro Trp Thr
1               5

<210> SEQ ID NO 33
<211> LENGTH: 107
```

```
<212> TYPE: PRT
<213> ORGANISM: Artificial Sequence
<220> FEATURE:
<223> OTHER INFORMATION: Human IgG1 Ig kappa chain C region found in
      SEQ ID NO: 28 and 29

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 737
<212> TYPE: DNA
<213> ORGANISM: Artificial Sequence
<220> FEATURE:
<223> OTHER INFORMATION: HEK293-6E codon optimized nucleic acid sequence
      encoding SEQ ID NO: 28

<400> SEQUENCE: 34
gaattcccgc cgccaccatg ggctggtcct gcatcatcct cttcctcgtc gccaccgcca      60
ccggcgtcca ctccgacatc gtcatgaccc agtcccctc ctccctcgcc atgtccgtcg       120
gccagaaggt caccctctcc tgcaagtcct cccagtccct cctcaactcc cgcaaccaga      180
agaactacct cgcctggtac cagcagaagc ccggccagtc ccccaagctc ctcatctact      240
tcacctccac ccgcgagtcc ggcgtccccg accgcttcat cggctccggc tccggcaccg      300 acttcacccct caccatctcc tccgtccagg ccgaggacct cgccgactac ttctgccagc      360
agcactactc ctcccctgg accttcggcg gcggcaccaa gctcgagatc aagcgcaccg       420
tcgccgcccc ctccgtcttc atcttccccc cctccgacga gcagctcaag tccggcaccg      480
cctccgtcgt ctgcctcctc aacaacttct accccgcga ggccaaggtc cagtggaagg       540
tcgacaacgc cctccagtcc ggcaactccc aggagtccgt caccgagcag gactccaagg      600
actccaccta ctccctctcc tccacccctca ccctctccaa ggccgactac gagaagcaca      660
aggtctacgc ctgcgaggtc acccaccagg gcctctcctc ccccgtcacc aagtccttca      720
accgcggcga gtgctga                                                      737

<210> SEQ ID NO 35
<211> LENGTH: 241
<212> TYPE: PRT
<213> ORGANISM: Artificial Sequence
<220> FEATURE:
<223> OTHER INFORMATION: VH1 heavy chain of humanized C100-Fab with
      leader sequence

<400> SEQUENCE: 35

Met Gly Trp Ser Cys Ile Ile Leu Phe Leu Val Ala Thr Ala Thr Gly
1               5                   10                  15
```

-continued

```
Val His Ser Gln Val Gln Leu Val Glu Ser Gly Gly Gly Leu Val Lys
         20              25              30

Pro Gly Gly Ser Leu Arg Leu Ser Cys Ala Ala Ser Gly Phe Thr Phe
         35              40              45

Ser Ser Phe Ala Met Ser Trp Ile Arg Gln Ala Pro Gly Lys Gly Leu
     50              55              60

Glu Trp Val Ser Ser Ile Thr Ser Ala Gly Thr Pro Tyr Tyr Pro Asp
65              70              75              80

Ser Val Leu Gly Arg Phe Thr Ile Ser Arg Asp Asn Ala Lys Asn Ser
                 85              90              95

Leu Tyr Leu Gln Met Asn Ser Leu Arg Ala Glu Asp Thr Ala Val Tyr
         100             105             110

Tyr Cys Ala Arg Ser Arg Gly Tyr Glu Asp Tyr Phe Asp Tyr Trp Gly
         115             120             125

Gln Gly Thr Leu Val Thr Val Ser Ser Ala Ser Thr Lys Gly Pro Ser
     130             135             140

Val Phe Pro Leu Ala Pro Ser Ser Lys Ser Thr Ser Gly Gly Thr Ala
145             150             155             160

Ala Leu Gly Cys Leu Val Lys Asp Tyr Phe Pro Glu Pro Val Thr Val
                 165             170             175

Ser Trp Asn Ser Gly Ala Leu Thr Ser Gly Val His Thr Phe Pro Ala
             180             185             190

Val Leu Gln Ser Ser Gly Leu Tyr Ser Leu Ser Ser Val Val Thr Val
         195             200             205

Pro Ser Ser Ser Leu Gly Thr Gln Thr Tyr Ile Cys Asn Val Asn His
         210             215             220

Lys Pro Ser Asn Thr Lys Val Asp Lys Lys Val Glu Pro Lys Ser Cys
225             230             235             240

Asp
```

```
<210> SEQ ID NO 36
<211> LENGTH: 222
<212> TYPE: PRT
<213> ORGANISM: Artificial Sequence
<220> FEATURE:
<223> OTHER INFORMATION: VH1 heavy chain of humanized C100-Fab without
      leader sequence

<400> SEQUENCE: 36
```

```
Gln Val Gln Leu Val Glu Ser Gly Gly Gly Leu Val Lys Pro Gly Gly
1               5               10              15

Ser Leu Arg Leu Ser Cys Ala Ala Ser Gly Phe Thr Phe Ser Ser Phe
         20              25              30

Ala Met Ser Trp Ile Arg Gln Ala Pro Gly Lys Gly Leu Glu Trp Val
         35              40              45

Ser Ser Ile Thr Ser Ala Gly Thr Pro Tyr Tyr Pro Asp Ser Val Leu
     50              55              60

Gly Arg Phe Thr Ile Ser Arg Asp Asn Ala Lys Asn Ser Leu Tyr Leu
65              70              75              80

Gln Met Asn Ser Leu Arg Ala Glu Asp Thr Ala Val Tyr Tyr Cys Ala
                 85              90              95

Arg Ser Arg Gly Tyr Glu Asp Tyr Phe Asp Tyr Trp Gly Gln Gly Thr
             100             105             110

Leu Val Thr Val Ser Ser Ala Ser Thr Lys Gly Pro Ser Val Phe Pro
         115             120             125
```

-continued

```
Leu Ala Pro Ser Ser Lys Ser Thr Ser Gly Gly Thr Ala Ala Leu Gly
    130                 135             140

Cys Leu Val Lys Asp Tyr Phe Pro Glu Pro Val Thr Val Ser Trp Asn
145                 150             155                 160

Ser Gly Ala Leu Thr Ser Gly Val His Thr Phe Pro Ala Val Leu Gln
                165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
        195             200             205

Asn Thr Lys Val Asp Lys Lys Val Glu Pro Lys Ser Cys Asp
    210             215             220

<210> SEQ ID NO 37
<211> LENGTH: 10
<212> TYPE: PRT
<213> ORGANISM: Artificial Sequence
<220> FEATURE:
<223> OTHER INFORMATION: VH1 heavy chain of humanized C100-Fab CDR1

<400> SEQUENCE: 37

Gly Phe Thr Phe Ser Ser Phe Ala Met Ser
1               5                   10

<210> SEQ ID NO 38
<211> LENGTH: 16
<212> TYPE: PRT
<213> ORGANISM: Artificial Sequence
<220> FEATURE:
<223> OTHER INFORMATION: VH1 heavy chain of humanized C100-Fab CDR2

<400> SEQUENCE: 38

Ser Ile Thr Ser Ala Gly Thr Pro Tyr Tyr Pro Asp Ser Val Leu Gly
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: VH1 heavy chain of humanized C100-Fab CDR3

<400> SEQUENCE: 39

Ser Arg Gly Tyr Glu Asp Tyr Phe Asp Tyr
1               5                   10

<210> SEQ ID NO 40
<211> LENGTH: 104
<212> TYPE: PRT
<213> ORGANISM: Artificial Sequence
<220> FEATURE:
<223> OTHER INFORMATION: Human IgG1 CH1 region found in SEQ ID NO: 35
     and 36

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20              25                  30

Phe Pro Glu Pro Val Thr Val Ser Trp Asn Ser Gly Ala Leu Thr Ser
            35              40                  45

Gly Val His Thr Phe Pro Ala Val Leu Gln Ser Ser Gly Leu Tyr Ser
```

-continued

```
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100
```

<210> SEQ ID NO 41
<211> LENGTH: 726
<212> TYPE: DNA
<213> ORGANISM: Artificial Sequence
<220> FEATURE:
<223> OTHER INFORMATION: Nucleic acid sequence encoding SEQ ID NO: 35

<400> SEQUENCE: 41

```
atgggctggt cctgcatcat cctcttcctc gtcgccaccg ccaccggcgt ccactcccag     60
gtgcagctgg tggaatcagg ggggggactg gtcaagcccg gagggtcact gagactgtca    120
tgtgccgcat cagggttcac ttttagctcc ttcgcaatgt cctggatccg acaggcacca    180
ggcaagggac tggagtgggt gtctagtatt acctctgctg gaacaccct ctatcctgac    240 agtgtcctgg ccggtttac tatctcaaga gataacgcaa aaaatagcct gtacctgcag    300
atgaactccc tgagggccga agacaccgct gtgtactatt gcgcccgcag cagggggtat    360
gaagattact ttgactactg ggggcagggg actctggtga ctgtctcctc cgcctccacc    420
aagggcccct ccgtcttccc cctcgccccc tcctccaagt ccacctccgg cggcaccgcc    480
gccctcggct gcctcgtcaa ggactacttc cccgagcccg tcaccgtctc ctggaactcc    540
ggcgccctca cctccggcgt ccacaccttc cccgccgtcc tccagtcctc cggcctctac    600
tccctctcct ccgtcgtcac cgtcccctcc tcctccctcg gcacccagac ctacatctgc    660
aacgtcaacc acaagccctc caacaccaag gtcgacaaga aggtcgagcc caagtcctgc    720
gactga                                                               726
```

<210> SEQ ID NO 42
<211> LENGTH: 241
<212> TYPE: PRT
<213> ORGANISM: Artificial Sequence
<220> FEATURE:
<223> OTHER INFORMATION: VH2 heavy chain of humanized C100-Fab with
    leader sequence

<400> SEQUENCE: 42

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Lys
                20                  25                  30

Pro Gly Gly Ser Leu Arg Leu Ser Cys Ala Ala Ser Gly Phe Thr Phe
            35                  40                  45

Ser Ser Phe Ala Met Ser Trp Val Arg Gln Ala Pro Gly Lys Gly Leu
        50                  55                  60

Glu Trp Val Ser Ser Ile Thr Ser Ala Gly Thr Pro Tyr Tyr Pro Asp
65                  70                  75                  80

Ser Val Leu Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110
```

-continued

Tyr Cys Ala Arg Ser Arg Gly Tyr Glu Asp Tyr Phe Asp Tyr Trp Gly
        115                     120                     125

Gln Gly Thr Thr Val Thr Val Ser Arg Ala Ser Thr Lys Gly Pro Ser
    130                     135                     140

Val Phe Pro Leu Ala Pro Ser Ser Lys Ser Thr Ser Gly Gly Thr Ala
145                     150                     155                     160

Ala Leu Gly Cys Leu Val Lys Asp Tyr Phe Pro Glu Pro Val Thr Val
                165                     170                     175

Ser Trp Asn Ser Gly Ala Leu Thr Ser Gly Val His Thr Phe Pro Ala
                180                     185                     190

Val Leu Gln Ser Ser Gly Leu Tyr Ser Leu Ser Ser Val Val Thr Val
                195                     200                     205

Pro Ser Ser Ser Leu Gly Thr Gln Thr Tyr Ile Cys Asn Val Asn His
    210                     215                     220

Lys Pro Ser Asn Thr Lys Val Asp Lys Lys Val Glu Pro Lys Ser Cys
225                     230                     235                     240

Asp

<210> SEQ ID NO 43
<211> LENGTH: 222
<212> TYPE: PRT
<213> ORGANISM: Artificial Sequence
<220> FEATURE:
<223> OTHER INFORMATION: VH2 heavy chain of humanized C100-Fab without
      leader sequence

<400> SEQUENCE: 43

Glu Val Gln Leu Val Glu Ser Gly Gly Gly Leu Val Lys Pro Gly Gly
1                   5                       10                      15

Ser Leu Arg Leu Ser Cys Ala Ala Ser Gly Phe Thr Phe Ser Ser Phe
                20                      25                      30

Ala Met Ser Trp Val Arg Gln Ala Pro Gly Lys Gly Leu Glu Trp Val
            35                      40                      45

Ser Ser Ile Thr Ser Ala Gly Thr Pro Tyr Tyr Pro Asp Ser Val Leu
    50                      55                      60

Gly Arg Phe Thr Ile Ser Arg Asp Asn Ala Lys Asn Ser Leu Tyr Leu
65                      70                      75                      80

Gln Met Asn Ser Leu Arg Ala Glu Asp Thr Ala Val Tyr Tyr Cys Ala
                85                      90                      95

Arg Ser Arg Gly Tyr Glu Asp Tyr Phe Asp Tyr Trp Gly Gln Gly Thr
                100                     105                     110

Thr Val Thr Val Ser Arg Ala Ser Thr Lys Gly Pro Ser Val Phe Pro
        115                     120                     125

Leu Ala Pro Ser Ser Lys Ser Thr Ser Gly Gly Thr Ala Ala Leu Gly
    130                     135                     140

Cys Leu Val Lys Asp Tyr Phe Pro Glu Pro Val Thr Val Ser Trp Asn
145                     150                     155                     160

Ser Gly Ala Leu Thr Ser Gly Val His Thr Phe Pro Ala Val Leu Gln
                165                     170                     175

Ser Ser Gly Leu Tyr Ser Leu Ser Ser Val Val Thr Val Pro Ser Ser
                180                     185                     190

Ser Leu Gly Thr Gln Thr Tyr Ile Cys Asn Val Asn His Lys Pro Ser
                195                     200                     205

Asn Thr Lys Val Asp Lys Lys Val Glu Pro Lys Ser Cys Asp
    210                     215                     220

-continued

```
<210> SEQ ID NO 44
<211> LENGTH: 10
<212> TYPE: PRT
<213> ORGANISM: Artificial Sequence
<220> FEATURE:
<223> OTHER INFORMATION: VH2 heavy chain of humanized C100-Fab CDR1

<400> SEQUENCE: 44

Gly Phe Thr Phe Ser Ser Phe Ala Met Ser
1               5                   10

<210> SEQ ID NO 45
<211> LENGTH: 16
<212> TYPE: PRT
<213> ORGANISM: Artificial Sequence
<220> FEATURE:
<223> OTHER INFORMATION: VH2 heavy chain of humanized C100-Fab CDR2

<400> SEQUENCE: 45

Ser Ile Thr Ser Ala Gly Thr Pro Tyr Tyr Pro Asp Ser Val Leu Gly
1               5                   10                  15

<210> SEQ ID NO 46
<211> LENGTH: 10
<212> TYPE: PRT
<213> ORGANISM: Artificial Sequence
<220> FEATURE:
<223> OTHER INFORMATION: VH2 heavy chain of humanized C100-Fab CDR3

<400> SEQUENCE: 46

Ser Arg Gly Tyr Glu Asp Tyr Phe Asp Tyr
1               5                   10

<210> SEQ ID NO 47
<211> LENGTH: 104
<212> TYPE: PRT
<213> ORGANISM: Artificial Sequence
<220> FEATURE:
<223> OTHER INFORMATION: Human IgG1 CH1 region found in SEQ ID NO: 42
      and 43

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 48
<211> LENGTH: 726
<212> TYPE: DNA
<213> ORGANISM: Artificial Sequence
<220> FEATURE:
<223> OTHER INFORMATION: Nucleic acid sequence encoding SEQ ID NO: 42
```

```
<400> SEQUENCE: 48
atgggctggt cctgcatcat cctcttcctc gtcgccaccg ccaccggcgt ccactccgag    60
gtgcagctgg tcgaatctgg aggaggactg gtcaagcctg ggggaagcct gagactgagt   120
tgtgccgcaa gtgggtttac atttagctcc ttcgcaatgt cctgggtgcg acaggcacca   180
ggcaagggac tggagtgggt ctctagtatc acctctgctg gaacacccta ctatcctgac   240
agtgtgctgg gccggtttac tatctcaaga gataacgcaa aaatagcct gtacctgcag    300 atgaactccc tgagggccga agacaccgct gtctactatt gcgcccgcag ccgagggtat   360
gaggattact ttgattattg ggggcagggc acaactgtca ctgtctccag agcctccacc   420
aagggcccct ccgtcttccc cctcgccccc tcctccaagt ccacctccgg cggcaccgcc   480
gccctcggct gcctcgtcaa ggactacttc cccgagcccg tcaccgtctc ctggaactcc   540
ggcgccctca cctccggcgt ccacaccttc cccgccgtcc tccagtcctc cggcctctac   600
tccctctcct ccgtcgtcac cgtcccctcc tcctccctcg caccagac ctacatctgc     660 aacgtcaacc acaagccctc caacaccaag gtcgacaaga aggtcgagcc caagtcctgc   720
gactga                                                             726

<210> SEQ ID NO 49
<211> LENGTH: 241
<212> TYPE: PRT
<213> ORGANISM: Artificial Sequence
<220> FEATURE:
<223> OTHER INFORMATION: VH3 heavy chain of humanized C100-Fab with
      leader sequence

<400> SEQUENCE: 49

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ala Met Ser Trp Val Arg Gln Ala Pro Gly Lys Gly Leu
    50                  55                  60

Glu Trp Val Ser Ser Ile Thr Ser Ala Gly Thr Pro Tyr Tyr Pro Asp
65                  70                  75                  80

Ser Val Leu Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Lys Ser Arg Gly Tyr Glu Asp Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
```

-continued

```
          210              215              220

Lys Pro Ser Asn Thr Lys Val Asp Lys Val Glu Pro Lys Ser Cys
225              230              235              240

Asp

<210> SEQ ID NO 50
<211> LENGTH: 222
<212> TYPE: PRT
<213> ORGANISM: Artificial Sequence
<220> FEATURE:
<223> OTHER INFORMATION: VH3 heavy chain of humanized C100-Fab without
      leader sequence

<400> SEQUENCE: 50

Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Ser Phe
            20              25              30

Ala Met Ser Trp Val Arg Gln Ala Pro Gly Lys Gly Leu Glu Trp Val
        35              40              45

Ser Ser Ile Thr Ser Ala Gly Thr Pro Tyr Tyr Pro Asp Ser Val Leu
    50              55              60

Gly Arg Phe Thr Ile Ser Arg Asp Asn Ser Lys Asn Thr Leu Tyr Leu
65              70              75              80

Gln Met Asn Ser Leu Arg Ala Glu Asp Thr Ala Val Tyr Tyr Cys Ala
            85              90              95

Lys Ser Arg Gly Tyr Glu Asp Tyr Phe Asp Tyr Trp Gly Gln Gly Thr
            100             105             110

Leu Val Thr Val Ser Ser Ala Ser Thr Lys Gly Pro Ser Val Phe Pro
        115             120             125

Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
        195             200             205

Asn Thr Lys Val Asp Lys Lys Val Glu Pro Lys Ser Cys Asp
    210             215             220

<210> SEQ ID NO 51
<211> LENGTH: 10
<212> TYPE: PRT
<213> ORGANISM: Artificial Sequence
<220> FEATURE:
<223> OTHER INFORMATION: VH3 heavy chain of humanized C100-Fab CDR1

<400> SEQUENCE: 51

Gly Phe Thr Phe Ser Ser Phe Ala Met Ser
1               5               10

<210> SEQ ID NO 52
<211> LENGTH: 16
<212> TYPE: PRT
<213> ORGANISM: Artificial Sequence
<220> FEATURE:
```

-continued

<223> OTHER INFORMATION: VH3 heavy chain of humanized C100-Fab CDR2

<400> SEQUENCE: 52

```
Ser Ile Thr Ser Ala Gly Thr Pro Tyr Tyr Pro Asp Ser Val Leu Gly
1               5                   10                  15
```

<210> SEQ ID NO 53
<211> LENGTH: 10
<212> TYPE: PRT
<213> ORGANISM: Artificial Sequence
<220> FEATURE:
<223> OTHER INFORMATION: VH3 heavy chain of humanized C100-Fab CDR3

<400> SEQUENCE: 53

```
Ser Arg Gly Tyr Glu Asp Tyr Phe Asp Tyr
1               5                   10
```

<210> SEQ ID NO 54
<211> LENGTH: 104
<212> TYPE: PRT
<213> ORGANISM: Artificial Sequence
<220> FEATURE:
<223> OTHER INFORMATION: Human IgG1 CH1 region found in SEQ ID NO: 49
      and 50

<400> SEQUENCE: 54

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100
```

<210> SEQ ID NO 55
<211> LENGTH: 726
<212> TYPE: DNA
<213> ORGANISM: Artificial Sequence
<220> FEATURE:
<223> OTHER INFORMATION: Nucleic acid sequence encoding SEQ ID NO: 49

<400> SEQUENCE: 55

```
atgggctggt cctgcatcat cctcttcctc gtcgccaccg ccaccggcgt ccactccgag      60
gtgcagctgg tggagagcgg ggggggactg gtgcagcctg cgggagcct gagactgtca     120 tgcgcagcaa gcggattcac ttttagctcc ttcgcaatga ctgggtgag gcaggcacca     180 ggcaagggac tggagtgggt ctctagtatc acctccgctg gaacacccta ctatcctgac     240
tctgtgctgg gccggtttac tatctcaaga gataacagca agaacaccct gtacctgcag     300
atgaacagtc tgcgggccga agacacagct gtctactatt gcgccaaatc caggggctac     360
gaagattact ttgattattg ggggcaggga actctggtga ccgtctcctc cgcctccacc     420
aagggcccct ccgtcttccc cctcgccccc tcctccaagt ccacctccgg cggcaccgcc     480
gccctcggct gcctcgtcaa ggactacttc cccgagcccg tcaccgtctc ctggaactcc     540
```

-continued

```
ggcgccctca cctccggcgt ccacaccttc cccgccgtcc tccagtcctc cggcctctac    600
tccctctcct ccgtcgtcac cgtcccctcc tcctccctcg caccagac ctacatctgc       660 aacgtcaacc acaagccctc caacaccaag gtcgacaaga aggtcgagcc caagtcctgc      720
gactga                                                               726
```

<210> SEQ ID NO 56
<211> LENGTH: 241
<212> TYPE: PRT
<213> ORGANISM: Artificial Sequence
<220> FEATURE:
<223> OTHER INFORMATION: VH4 heavy chain of humanized C100-Fab with
      leader sequence

<400> SEQUENCE: 56

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Phe Ala Met Ser Trp Val Arg Gln Ala Pro Gly Lys Gly Leu
        50                  55                  60

Glu Trp Val Ala Ser Ile Thr Ser Ala Gly Thr Pro Tyr Tyr Pro Asp
65                  70                  75                  80

Ser Val Leu Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Ser Arg Gly Tyr Glu Asp Tyr Phe Asp Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Lys Val Glu Pro Lys Ser Cys
225                 230                 235                 240

Asp
```

<210> SEQ ID NO 57
<211> LENGTH: 222
<212> TYPE: PRT
<213> ORGANISM: Artificial Sequence
<220> FEATURE:
<223> OTHER INFORMATION: VH4 heavy chain of humanized C100-Fab without
      leader sequence

<400> SEQUENCE: 57

```
Gln Val Gln Leu Val Glu Ser Gly Gly Gly Val Val Gln Pro Gly Arg
```

-continued

```
1                5                10               15

Ser Leu Arg Leu Ser Cys Ala Ala Ser Gly Phe Thr Phe Ser Ser Phe
         20                25                30

Ala Met Ser Trp Val Arg Gln Ala Pro Gly Lys Gly Leu Glu Trp Val
         35                40                45

Ala Ser Ile Thr Ser Ala Gly Thr Pro Tyr Tyr Pro Asp Ser Val Leu
    50                55                60

Gly Arg Phe Thr Ile Ser Arg Asp Asn Ser Lys Asn Thr Leu Tyr Leu
65                70                75                80

Gln Met Asn Ser Leu Arg Ala Glu Asp Thr Ala Val Tyr Tyr Cys Ala
         85                90                95

Arg Ser Arg Gly Tyr Glu Asp Tyr Phe Asp Tyr Trp Gly Gln Gly Thr
         100               105               110

Leu Val Thr Val Ser Ser Ala Ser Thr Lys Gly Pro Ser Val Phe Pro
         115               120               125

Leu Ala Pro Ser Ser Lys Ser Thr Ser Gly Gly Thr Ala Ala Leu Gly
    130               135               140

Cys Leu Val Lys Asp Tyr Phe Pro Glu Pro Val Thr Val Ser Trp Asn
145               150               155               160

Ser Gly Ala Leu Thr Ser Gly Val His Thr Phe Pro Ala Val Leu Gln
         165               170               175

Ser Ser Gly Leu Tyr Ser Leu Ser Ser Val Val Thr Val Pro Ser Ser
         180               185               190

Ser Leu Gly Thr Gln Thr Tyr Ile Cys Asn Val Asn His Lys Pro Ser
         195               200               205

Asn Thr Lys Val Asp Lys Lys Val Glu Pro Lys Ser Cys Asp
    210               215               220
```

```
<210> SEQ ID NO 58
<211> LENGTH: 10
<212> TYPE: PRT
<213> ORGANISM: Artificial Sequence
<220> FEATURE:
<223> OTHER INFORMATION: VH4 heavy chain of humanized C100-Fab CDR1

<400> SEQUENCE: 58

Gly Phe Thr Phe Ser Ser Phe Ala Met Ser
1               5                10
```

```
<210> SEQ ID NO 59
<211> LENGTH: 16
<212> TYPE: PRT
<213> ORGANISM: Artificial Sequence
<220> FEATURE:
<223> OTHER INFORMATION: VH4 heavy chain of humanized C100-Fab CDR2

<400> SEQUENCE: 59

Ser Ile Thr Ser Ala Gly Thr Pro Tyr Tyr Pro Asp Ser Val Leu Gly
1               5                10               15
```

```
<210> SEQ ID NO 60
<211> LENGTH: 10
<212> TYPE: PRT
<213> ORGANISM: Artificial Sequence
<220> FEATURE:
<223> OTHER INFORMATION: VH4 heavy chain of humanized C100-Fab CDR3

<400> SEQUENCE: 60

Ser Arg Gly Tyr Glu Asp Tyr Phe Asp Tyr
1               5                10
```

-continued

```
<210> SEQ ID NO 61
<211> LENGTH: 104
<212> TYPE: PRT
<213> ORGANISM: Artificial Sequence
<220> FEATURE:
<223> OTHER INFORMATION: Human IgG1 CH1 region found in SEQ ID NO: 56
      and 57

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 62
<211> LENGTH: 726
<212> TYPE: DNA
<213> ORGANISM: Artificial Sequence
<220> FEATURE:
<223> OTHER INFORMATION: Nucleic acid sequence encoding SEQ ID NO: 56

<400> SEQUENCE: 62
atgggctggt cctgcatcat cctcttcctc gtcgccaccg ccaccggcgt ccactcccag      60
gtgcagctgg tcgagagcgg aggaggggtg gtccagcccg gaaggtcact gagactgagt     120
tgtgccgcaa gcggattcac tttcagctcc ttcgctatga gctgggtgcg acaggcacca     180
ggcaagggac tggagtgggt cgcatctatc accagtgccg gaacaccctc ctatcctgac     240
agcgtgctgg gccggtttac tatctcaaga gataacagca gaacaccct gtacctgcag      300 atgaactccc tgagggccga gacacagct gtctactatt gcgcccgctc tcggggatac      360
gaggattatt ttgattattg gggacagggg acactggtca ccgtcagcag cgcctccacc     420
aagggcccct ccgtcttccc cctcgccccc tcctccaagt ccacctccgg cggcaccgcc     480
gccctcggct gcctcgtcaa ggactacttc cccgagcccg tcaccgtctc ctggaactcc     540
ggcgccctca cctccggcgt ccacaccttc cccgccgtcc tccagtcctc cggcctctac     600
tccctctcct ccgtcgtcac cgtcccctcc tcctccctcg gcacccagac ctacatctgc     660
aacgtcaacc acaagccctc caacaccaag gtcgacaaga aggtcgagcc caagtcctgc     720
gactga                                                               726

<210> SEQ ID NO 63
<211> LENGTH: 239
<212> TYPE: PRT
<213> ORGANISM: Artificial Sequence
<220> FEATURE:
<223> OTHER INFORMATION: VL1 light chain of humanized C100-Fab with
      leader sequence

<400> SEQUENCE: 63
```

-continued

```
Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
                20                  25                  30

Ser Leu Gly Glu Arg Ala Thr Ile Asn Cys Lys Ser Ser Gln Ser Leu
        35                  40                  45

Leu Asn Ser Arg Asn Gln Lys Asn Tyr Leu Ala Trp Tyr Gln Gln Lys
    50                  55                  60

Pro Gly Gln Pro Pro Lys Leu Leu Ile Tyr Phe Thr Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
            100                 105                 110

Cys Gln Gln His Tyr Ser Ser Pro Trp Thr Phe Gly Gly Gly Thr Lys
            115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 64
<211> LENGTH: 220
<212> TYPE: PRT
<213> ORGANISM: Artificial Sequence
<220> FEATURE:
<223> OTHER INFORMATION: VL1 light chain of humanized C100-Fab without
      leader sequence

<400> SEQUENCE: 64
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Asn Gln Lys Asn Tyr Leu Ala Trp Tyr Gln Gln Lys Pro Gly Gln
        35                  40                  45

Pro Pro Lys Leu Leu Ile Tyr Phe Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Ser Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
```

-continued

```
          115                 120                 125
Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 65
<211> LENGTH: 17
<212> TYPE: PRT
<213> ORGANISM: Artificial Sequence
<220> FEATURE:
<223> OTHER INFORMATION: VL1 light chain of humanized C100-Fab CDR1

<400> SEQUENCE: 65

Lys Ser Ser Gln Ser Leu Leu Asn Ser Arg Asn Gln Lys Asn Tyr Leu
1               5                   10                  15

Ala

<210> SEQ ID NO 66
<211> LENGTH: 7
<212> TYPE: PRT
<213> ORGANISM: Artificial Sequence
<220> FEATURE:
<223> OTHER INFORMATION: VL1 light chain of humanized C100-Fab CDR2

<400> SEQUENCE: 66

Phe Thr Ser Thr Arg Glu Ser
1               5

<210> SEQ ID NO 67
<211> LENGTH: 9
<212> TYPE: PRT
<213> ORGANISM: Artificial Sequence
<220> FEATURE:
<223> OTHER INFORMATION: VL1 light chain of humanized C100-Fab CDR3

<400> SEQUENCE: 67

Gln Gln His Tyr Ser Ser Pro Trp Thr
1               5

<210> SEQ ID NO 68
<211> LENGTH: 107
<212> TYPE: PRT
<213> ORGANISM: Artificial Sequence
<220> FEATURE:
<223> OTHER INFORMATION: Human IgG1 Ig kappa chain C region found in
      SEQ ID NO: 63 and 64

<400> SEQUENCE: 68

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
```

-continued

```
          35                    40                    45
Ser Gly Asn Ser Gln Glu Ser Val Thr Glu Gln Asp Ser Lys Asp Ser
    50                    55                    60

Thr Tyr Ser Leu Ser Ser Thr Leu Thr Leu Ser Lys Ala Asp Tyr Glu
65                    70                    75                    80

Lys His Lys Val Tyr Ala Cys Glu Val Thr His Gln Gly Leu Ser Ser
                  85                    90                    95

Pro Val Thr Lys Ser Phe Asn Arg Gly Glu Cys
                 100                   105
```

```
<210> SEQ ID NO 69
<211> LENGTH: 720
<212> TYPE: DNA
<213> ORGANISM: Artificial Sequence
<220> FEATURE:
<223> OTHER INFORMATION: Nucleic acid sequence encoding SEQ ID NO: 63

<400> SEQUENCE: 69
atgggctggt cctgcatcat cctcttcctc gtcgccaccg ccaccggcgt ccactccgac        60
attgtgatga cacagagccc tgacagcctg gccgtgagcc tgggggaaag agcaactatc       120
aactgcaaaa gcagccagag cctgctgaac agtaggaatc agaagaacta cctggcctgg       180
tatcagcaga gccaggcca gcccctaaa ctgctgatct acttcaccag cacacgagag         240
tccggagtgc cagacagatt ctctggcagt gggtcaggaa cagatttac tctgaccatt        300 agctccctgc aggccgaaga cgtggctgtc tactattgtc agcagcatta ctcatcaccc       360
tggaccttcg gggggggcac taaactggaa atcaaacgca ccgtcgccgc cccctccgtc       420
ttcatcttcc cccctccga cgagcagctc aagtccggca ccgcctccgt cgtctgcctc        480
ctcaacaact ctacccccg cgaggccaag gtccagtgga aggtcgacaa cgccctccag        540
tccggcaact cccaggagtc cgtcaccgag caggactcca aggactccac ctactccctc       600
tcctccaccc tcaccctctc caaggccgac tacgagaagc acaaggtcta cgcctgcgag       660
gtcacccacc agggcctctc ctcccccgtc accaagtcct tcaaccgcgg cgagtgctga       720
```

```
<210> SEQ ID NO 70
<211> LENGTH: 239
<212> TYPE: PRT
<213> ORGANISM: Artificial Sequence
<220> FEATURE:
<223> OTHER INFORMATION: VL2 light chain of humanized C100-Fab with
      leader sequence

<400> SEQUENCE: 70

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Lys Ser Ser Gln Ser Leu
        35                  40                  45

Leu Asn Ser Arg Asn Gln Lys Asn Tyr Leu Ala Trp Tyr Gln Gln Lys
    50                  55                  60

Pro Gly Lys Ala Pro Lys Leu Leu Ile Tyr Phe Thr Ser Thr Arg Glu
65                  70                  75                  80

Ser Gly Val Pro Ser Arg Phe Ser Gly Ser Gly Ser Gly Thr Asp Phe
                85                  90                  95

Thr Leu Thr Ile Ser Ser Leu Gln Pro Glu Asp Phe Ala Thr Tyr Tyr
            100                 105                 110
```

-continued

```
Cys Gln Gln His Tyr Ser Ser Pro Trp Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 71
<211> LENGTH: 220
<212> TYPE: PRT
<213> ORGANISM: Artificial Sequence
<220> FEATURE:
<223> OTHER INFORMATION: VL2 light chain of humanized C100-Fab without
      leader sequence

<400> SEQUENCE: 71
```

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Asn Gln Lys Asn Tyr Leu Ala Trp Tyr Gln Gln Lys Pro Gly Lys
        35                  40                  45

Ala Pro Lys Leu Leu Ile Tyr Phe Thr Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Ser Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

-continued

<210> SEQ ID NO 72
<211> LENGTH: 17
<212> TYPE: PRT
<213> ORGANISM: Artificial Sequence
<220> FEATURE:
<223> OTHER INFORMATION: VL2 light chain of humanized C100-Fab CDR1

<400> SEQUENCE: 72

Lys Ser Ser Gln Ser Leu Leu Asn Ser Arg Asn Gln Lys Asn Tyr Leu
1               5                   10                  15

Ala

<210> SEQ ID NO 73
<211> LENGTH: 7
<212> TYPE: PRT
<213> ORGANISM: Artificial Sequence
<220> FEATURE:
<223> OTHER INFORMATION: VL2 light chain of humanized C100-Fab CDR2

<400> SEQUENCE: 73

Phe Thr Ser Thr Arg Glu Ser
1               5

<210> SEQ ID NO 74
<211> LENGTH: 9
<212> TYPE: PRT
<213> ORGANISM: Artificial Sequence
<220> FEATURE:
<223> OTHER INFORMATION: VL2 light chain of humanized C100-Fab CDR3

<400> SEQUENCE: 74

Gln Gln His Tyr Ser Ser Pro Trp Thr
1               5

<210> SEQ ID NO 75
<211> LENGTH: 107
<212> TYPE: PRT
<213> ORGANISM: Artificial Sequence
<220> FEATURE:
<223> OTHER INFORMATION: Human IgG1 Ig kappa chain C region found in
      SEQ ID NO: 70 and 71

<400> SEQUENCE: 75

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 76
<211> LENGTH: 720
<212> TYPE: DNA
<213> ORGANISM: Artificial Sequence
<220> FEATURE:
<223> OTHER INFORMATION: Nucleic acid sequence encoding SEQ ID NO: 70

<400> SEQUENCE: 76
atgggctggt cctgcatcat cctcttcctc gtcgccaccg ccaccggcgt ccactccgac      60
atccagatga cccagagccc aagtagcctg agcgccagcg tcggagatag agtgaccatt     120
acctgcaaga gtagccagtc cctgctgaac agcaggaatc agaaaaacta cctggcctgg     180
tatcagcaga gcccggcaa agctcctaag ctgctgatct acttcaccag cacacgggag     240 tccgggtgc catctagatt ctctggcagt gggtcaggaa cagactttac tctgaccatt     300
agctccctgc agcccgaaga ttttgccacc tactattgtc agcagcatta ttcatcacct     360
tggaccttcg gcagggaac aaaagtggaa atcaaacgca ccgtcgccgc cccctccgtc     420
ttcatcttcc cccctccga cgagcagctc aagtccggca ccgcctccgt cgtctgcctc     480
ctcaacaact ctacccccg cgaggccaag gtccagtgga aggtcgacaa cgccctccag     540
tccggcaact cccaggagtc cgtcaccgag caggactcca aggactccac ctactccctc     600
tcctccaccc tcaccctctc caaggccgac tacgagaagc acaaggtcta cgcctgcgag     660
gtcacccacc agggcctctc ctcccccgtc accaagtcct tcaaccgcgg cgagtgctga     720

<210> SEQ ID NO 77
<211> LENGTH: 239
<212> TYPE: PRT
<213> ORGANISM: Artificial Sequence
<220> FEATURE:
<223> OTHER INFORMATION: VL3 light chain of humanized C100-Fab with
      leader sequence

<400> SEQUENCE: 77

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
                20                  25                  30

Thr Pro Gly Glu Pro Ala Ser Ile Ser Cys Lys Ser Ser Gln Ser Leu
            35                  40                  45

Leu Asn Ser Arg Asn Gln Lys Asn Tyr Leu Ala Trp Tyr Leu Gln Lys
        50                  55                  60

Pro Gly Gln Ser Pro Gln Leu Leu Ile Tyr Phe Thr Ser Thr Arg Glu
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Gln Gln His Tyr Ser Ser Pro Trp Thr Phe Gly Gln Gly Thr Lys
        115                 120                 125

Val Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 78
<211> LENGTH: 220
<212> TYPE: PRT
<213> ORGANISM: Artificial Sequence
<220> FEATURE:
<223> OTHER INFORMATION: VL3 light chain of humanized C100-Fab without
      leader sequence

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Arg Asn Gln Lys Asn Tyr Leu Ala Trp Tyr Leu Gln Lys Pro Gly Gln
        35                  40                  45

Ser Pro Gln Leu Leu Ile Tyr Phe Thr Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

His Tyr Ser Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 79
<211> LENGTH: 17
<212> TYPE: PRT
<213> ORGANISM: Artificial Sequence
<220> FEATURE:
<223> OTHER INFORMATION: VL3 light chain of humanized C100-Fab CDR1

<400> SEQUENCE: 79

Lys Ser Ser Gln Ser Leu Leu Asn Ser Arg Asn Gln Lys Asn Tyr Leu
1               5                   10                  15

Ala

<210> SEQ ID NO 80
<211> LENGTH: 7
<212> TYPE: PRT
<213> ORGANISM: Artificial Sequence
<220> FEATURE:
<223> OTHER INFORMATION: VL3 light chain of humanized C100-Fab CDR2

<400> SEQUENCE: 80

Phe Thr Ser Thr Arg Glu Ser
1               5

<210> SEQ ID NO 81
<211> LENGTH: 9
<212> TYPE: PRT
<213> ORGANISM: Artificial Sequence
<220> FEATURE:
<223> OTHER INFORMATION: VL3 light chain of humanized C100-Fab CDR3

<400> SEQUENCE: 81

Gln Gln His Tyr Ser Ser Pro Trp Thr
1               5

<210> SEQ ID NO 82
<211> LENGTH: 107
<212> TYPE: PRT
<213> ORGANISM: Artificial Sequence
<220> FEATURE:
<223> OTHER INFORMATION: Human IgG1 Ig kappa chain C region found in
      SEQ ID NO: 77 and 78

<400> SEQUENCE: 82

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 83
<211> LENGTH: 720
<212> TYPE: DNA
<213> ORGANISM: Artificial Sequence
<220> FEATURE:
<223> OTHER INFORMATION: Nucleic acid sequence encoding SEQ ID NO: 77

<400> SEQUENCE: 83
atgggctggt cctgcatcat cctcttcctc gtcgccaccg ccaccggcgt ccactccgac      60
attgtgatga cccagagccc cctgagcctg ccagtgaccc ccggagagcc tgctagtatt     120
tcctgtaagt ccagccagtc cctgctgaac agcaggaatc agaagaacta cctggcctgg     180
tatctgcaga aacccggcca gtcccctcag ctgctgatct acttcaccag tacacgggag     240
tcaggagtgc cagacagatt cagcggatcc ggatctggaa ctgattttac cctgaagatt     300
agtcgggtcg aggctgaaga cgtgggcgtc tactattgcc agcagcatta ctcatcacct     360
tggaccttcg gacagggaac aaaaagtgga atcaaacgca ccgtcgccgc ccctccgtc      420 ttcatcttcc cccctccgga cgagcagctc aagtccggca ccgcctccgt cgtctgcctc     480
ctcaacaact ctaccccccg cgaggccaag gtccagtgga aggtcgacaa cgccctccag     540

-continued

```
tccggcaact cccaggagtc cgtcaccgag caggactcca aggactccac ctactccctc      600
tcctccaccc tcaccctctc caaggccgac tacgagaagc acaaggtcta cgcctgcgag      660
gtcacccacc agggcctctc ctcccccgtc accaagtcct tcaaccgcgg cgagtgctga      720
```

<210> SEQ ID NO 84
<211> LENGTH: 239
<212> TYPE: PRT
<213> ORGANISM: Artificial Sequence
<220> FEATURE:
<223> OTHER INFORMATION: VL4 light chain of humanized C100-Fab with
      leader sequence

<400> SEQUENCE: 84

```
Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Leu Gly Gln Pro Ala Ser Ile Ser Cys Lys Ser Ser Gln Ser Leu
        35                  40                  45

Leu Asn Ser Arg Asn Gln Lys Asn Tyr Leu Ala Trp Phe Gln Gln Arg
    50                  55                  60

Pro Gly Gln Ser Pro Arg Arg Leu Ile Tyr Phe Thr Ser Thr Arg Glu
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Gln Gln His Tyr Ser Ser Pro Trp Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 85
<211> LENGTH: 220
<212> TYPE: PRT
<213> ORGANISM: Artificial Sequence
<220> FEATURE:
<223> OTHER INFORMATION: VL4 light chain of humanized C100-Fab without
      leader sequence

<400> SEQUENCE: 85

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asn Ser
            20                  25                  30
```

```
Arg Asn Gln Lys Asn Tyr Leu Ala Trp Phe Gln Gln Arg Pro Gly Gln
        35                  40                  45

Ser Pro Arg Arg Leu Ile Tyr Phe Thr Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

His Tyr Ser Ser Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 86
<211> LENGTH: 17
<212> TYPE: PRT
<213> ORGANISM: Artificial Sequence
<220> FEATURE:
<223> OTHER INFORMATION: VL4 light chain of humanized C100-Fab CDR1

<400> SEQUENCE: 86

Lys Ser Ser Gln Ser Leu Leu Asn Ser Arg Asn Gln Lys Asn Tyr Leu
1               5                   10                  15

Ala

<210> SEQ ID NO 87
<211> LENGTH: 7
<212> TYPE: PRT
<213> ORGANISM: Artificial Sequence
<220> FEATURE:
<223> OTHER INFORMATION: VL4 light chain of humanized C100-Fab CDR2

<400> SEQUENCE: 87

Phe Thr Ser Thr Arg Glu Ser
1               5

<210> SEQ ID NO 88
<211> LENGTH: 9
<212> TYPE: PRT
<213> ORGANISM: Artificial Sequence
<220> FEATURE:
<223> OTHER INFORMATION: VL4 light chain of humanized C100-Fab CDR3

<400> SEQUENCE: 88

Gln Gln His Tyr Ser Ser Pro Trp Thr
1               5

<210> SEQ ID NO 89
```

```
<211> LENGTH: 107
<212> TYPE: PRT
<213> ORGANISM: Artificial Sequence
<220> FEATURE:
<223> OTHER INFORMATION: Human IgG1 Ig kappa chain C region found in
     SEQ ID NO: 56 and 57

<400> SEQUENCE: 89

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 90
<211> LENGTH: 720
<212> TYPE: DNA
<213> ORGANISM: Artificial Sequence
<220> FEATURE:
<223> OTHER INFORMATION: Nucleic acid sequence encoding SEQ ID NO: 56

<400> SEQUENCE: 90
atgggctggt cctgcatcat cctcttcctc gtcgccaccg ccaccggcgt ccactccgac      60
gtcgtgatga cccagagccc cctgagcctg cccgtgaccc tgggacagcc tgcctcaatc     120
tcctgtaaaa gtagccagag cctgctgaac agccgaaatc agaagaacta cctggcctgg     180
ttccagcaga gaccaggaca gtcccctcga agactgatct attttaccag tacaagggag     240
tcaggagtgc cagaccgctt cagcggatcc ggatctggaa ctgattttac cctgaaaatt     300
agtcgggtcg aggctgaaga cgtgggcgtc tactattgtc agcagcacta ttcatcacct     360
tggaccttcg gcagggaac aaaactggaa atcaaacgca ccgtcgccgc ccctccgtc       420 ttcatcttcc ccccctccga cgagcagctc aagtccggca ccgcctccgt cgtctgcctc     480
ctcaacaact ctaccccccg cgaggccaag gtccagtgga aggtcgacaa cgccctccag     540
tccggcaact cccaggagtc cgtcaccgag caggactcca aggactccac ctactccctc     600
tcctccaccc tcaccctctc caaggccgac tacgagaagc acaaggtcta cgcctgcgag     660
gtcacccacc agggcctctc ctccccgtc accaagtcct tcaaccgcgg cgagtgctga     720

<210> SEQ ID NO 91
<211> LENGTH: 19
<212> TYPE: PRT
<213> ORGANISM: Artificial Sequence
<220> FEATURE:
<223> OTHER INFORMATION: Leader sequence

<400> SEQUENCE: 91

Met Gly Trp Ser Cys Ile Ile Leu Phe Leu Val Ala Thr Ala Thr Gly
1               5                   10                  15

Val His Ser
```

<210> SEQ ID NO 92
<211> LENGTH: 5
<212> TYPE: PRT
<213> ORGANISM: Artificial Sequence
<220> FEATURE:
<223> OTHER INFORMATION: GS linker

<400> SEQUENCE: 92

Gly Gly Gly Gly Ser
1               5

<210> SEQ ID NO 93
<211> LENGTH: 118
<212> TYPE: PRT
<213> ORGANISM: Artificial Sequence
<220> FEATURE:
<223> OTHER INFORMATION: Variable region in VH1

<400> SEQUENCE: 93

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Ile Arg Gln Ala Pro Gly Lys Gly Leu Glu Trp Val
        35                  40                  45

Ser Ser Ile Thr Ser Ala Gly Thr Pro Tyr Tyr Pro Asp Ser Val Leu
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Arg Gly Tyr Glu Asp Tyr Phe Asp Tyr Trp Gly Gln Gly Thr
            100                 105                 110

Leu Val Thr Val Ser Ser
        115

<210> SEQ ID NO 94
<211> LENGTH: 118
<212> TYPE: PRT
<213> ORGANISM: Artificial Sequence
<220> FEATURE:
<223> OTHER INFORMATION: Variable region in VH4

<400> SEQUENCE: 94

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ala Ser Ile Thr Ser Ala Gly Thr Pro Tyr Tyr Pro Asp Ser Val Leu
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Arg Gly Tyr Glu Asp Tyr Phe Asp Tyr Trp Gly Gln Gly Thr
            100                 105                 110

Leu Val Thr Val Ser Ser

115

```
<210> SEQ ID NO 95
<211> LENGTH: 113
<212> TYPE: PRT
<213> ORGANISM: Artificial Sequence
<220> FEATURE:
<223> OTHER INFORMATION: Variable region in VL2

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Asn Gln Lys Asn Tyr Leu Ala Trp Tyr Gln Gln Lys Pro Gly Lys
        35                  40                  45

Ala Pro Lys Leu Leu Ile Tyr Phe Thr Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Ser Ser Pro Trp Thr Phe Gly Gln Gly Thr Lys Val Glu Ile
                100                 105                 110

Lys

<210> SEQ ID NO 96
<211> LENGTH: 113
<212> TYPE: PRT
<213> ORGANISM: Artificial Sequence
<220> FEATURE:
<223> OTHER INFORMATION: Variable region in VL3

<400> SEQUENCE: 96

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Arg Asn Gln Lys Asn Tyr Leu Ala Trp Tyr Leu Gln Lys Pro Gly Gln
        35                  40                  45

Ser Pro Gln Leu Leu Ile Tyr Phe Thr Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

His Tyr Ser Ser Pro Trp Thr Phe Gly Gln Gly Thr Lys Val Glu Ile
                100                 105                 110

Lys
```